United States Patent [19]
Lewy et al.

[11] Patent Number: 6,069,164
[45] Date of Patent: *May 30, 2000

[54] METHODS FOR TREATING CIRCADIAN RHYTHM PHASE DISTURBANCES

[75] Inventors: Alfred J. Lewy; Robert L. Sack, both of Portland, Oreg.

[73] Assignee: Oregon Health Sciences University, Portland, Oreg.

[ * ] Notice: This patent is subject to a terminal disclaimer.

[21] Appl. No.: 08/778,842

[22] Filed: Jan. 6, 1997

Related U.S. Application Data

[60] Division of application No. 08/110,878, Aug. 24, 1993, Pat. No. 5,591,768, which is a continuation-in-part of application No. 07/842,723, Feb. 25, 1992, Pat. No. 5,242,941, which is a continuation of application No. 07/621,866, Dec. 4, 1990, abandoned.

[51] Int. Cl.$^7$ .......................... A61K 31/40; A61K 31/405
[52] U.S. Cl. .......................... 514/415; 514/416; 514/418; 514/419; 548/491; 548/494; 548/495; 548/496
[58] Field of Search .................................... 514/415, 416, 514/418, 419; 548/491, 494, 495, 496

[56] References Cited

U.S. PATENT DOCUMENTS

| | | | |
|---|---|---|---|
| 4,600,723 | 7/1986 | Short et al. | 514/416 |
| 4,665,086 | 5/1987 | Short et al. | 514/416 |
| 4,687,763 | 8/1987 | Wurtman | 514/53 |
| 5,163,426 | 11/1992 | Czeisler et al. | 128/395 |
| 5,167,228 | 12/1992 | Czeisler et al. | 128/395 |
| 5,176,133 | 1/1993 | Czeisler et al. | 128/395 |
| 5,242,941 | 9/1993 | Lewy et al. | 514/416 |
| 5,420,152 | 5/1995 | Lewy et al. | 514/419 |
| 5,591,768 | 1/1997 | Lewy et al. | 514/415 |

FOREIGN PATENT DOCUMENTS

| | | |
|---|---|---|
| 126630 | 11/1984 | European Pat. Off. . |
| 578620 | 1/1994 | European Pat. Off. . |
| WO9307870 | 4/1993 | WIPO . |

OTHER PUBLICATIONS

Arendt et al., 1984, "The effects of chronic, small doses of melatonin given in the late afternoon on fatigue in man: A preliminary study," *Neurosci. Lett.* 45:317–325.
Arendt et al., 1985, "Some effects of melatonin and the control of its secretion in humans," *CIBA Found. Symp.* 117:266–283.
Arendt et al., 1987, "Some effects of jet–lag and their alleviation by melatonin," *Ergonomics* 30:1379–1393.
Armstrong, 1989, "Melatonin anc circadian control in mammals," *Experientia* 45:932–938.
Armstrong, 1991, "Treatment of sleep disorders by melatonin administration," *Adv. In Pineal Res.* 6:263–274.
Blood et al., 1993, "Serengeti® vermilion sunglasses inhibit the suppressant effect of bright light on melatonin secretion," *Sleep Res.* 22:394 (Abst.).
Cagnacci et al., 1992, "Melatonin: A Major Regulator of the Circadian Rhythm of Core Temperature," *J. Clin. Endocrinol. Metab.* 75(2):447–452.
Claustrat et al., 1992, "Melatonin and jet–lag: confirmatory result using a simplified protocol," *Biol. Psychiatry* 32:705–711.
Gwinner, 1978, "The effects of pinealectomy on circadian locomotor activity rhythms in European starlings, *Sturnus vulgaris,*" *J. Comp. Physiol.* 126:123–129.
Lewy and Markey, 1978, "Analysis of Melatonin in Human Plasma by Gas Chromatography Negative Chemical Ionization Mass Spectrometry," *Science* 201:741–743.
Lewy et al., 1992, "Melatonin shifts human circadian rhythms according to a phase–response curve," *Chronobiol. Int'l.* 9:380–392.
Mallo et al., 1988, "Effects of a four–day nocturnal melatonin treatment on the 24 h plasma melatonin, cortisol and prolactin profiles in humans," *Acta Endocrinol.* 119:474–480.
Nickelsen et al., 1991, "The effects of 6–,9– and 11–hour time shifts on circadian rhythms: adaptation of sleep parameters and hormonal patterns following the intake of melatonin or placebo," *Adv. Pineal Res.* 5:303–306.
Parry et al., 1987, "Treatment of a Patient With Seasonal Premenstrual Syndrome," *Am. J. Psychiatry* 144(6):762–766.
Petrie et al., 1989, "Effect of melatonin on jet lag after long hauls," *Br. Med. J.* 298:705–707.
Rosenthal et al, 1988, "Atenolol in seasonal affective disorder: A test of the melatonin hypothesis," *Amer. J. Psychiatry* 145:52–56.
Samel et al., 1991, "Influence of melatonin treatment on human circadian rhythmicity before and after simulated 9–hr time shift," *J. Biol. Rhythms* 6:235–248.
Skene et al., 1989, "Melatonin, jet–lag and the sleep–wake cycle," *Sleep '88* (J. Horne, ed.) pp. 39–41.
Underwood, 1986, "Circadian Rhythms in Lizards: Phase Response Curve for Melatonin," *J. Pineal Res.* 3:187–196.
Wirz–Justice et al., 1990, "Morning or night–time melatonin in ineffective in seasonal affective disorder," *J. Psychiatr. Res.* 24:129–137.
Zimmerman et al., 1990, "Melatonin and the ovulatory luteinizing hormone surge," *Fertil. Steril.* 54:612–618.

*Primary Examiner*—Peter G. O'Sullivan
*Attorney, Agent, or Firm*—McDonnell Boehnen Hulbert & Berghoff

[57] ABSTRACT

A method for treating circadian rhythm phase disorders is described. The invention provides methods to specifically advance or delay the phase of certain circadian rhythms in humans. The disclosed methods relate to the administration of melatonin at times determined with relation to the time of dim light endogenous melatonin onset. Embodiments capable of alleviating the effects of jet lag, winter depression and shift-work sleep disturbance are provided.

4 Claims, 40 Drawing Sheets

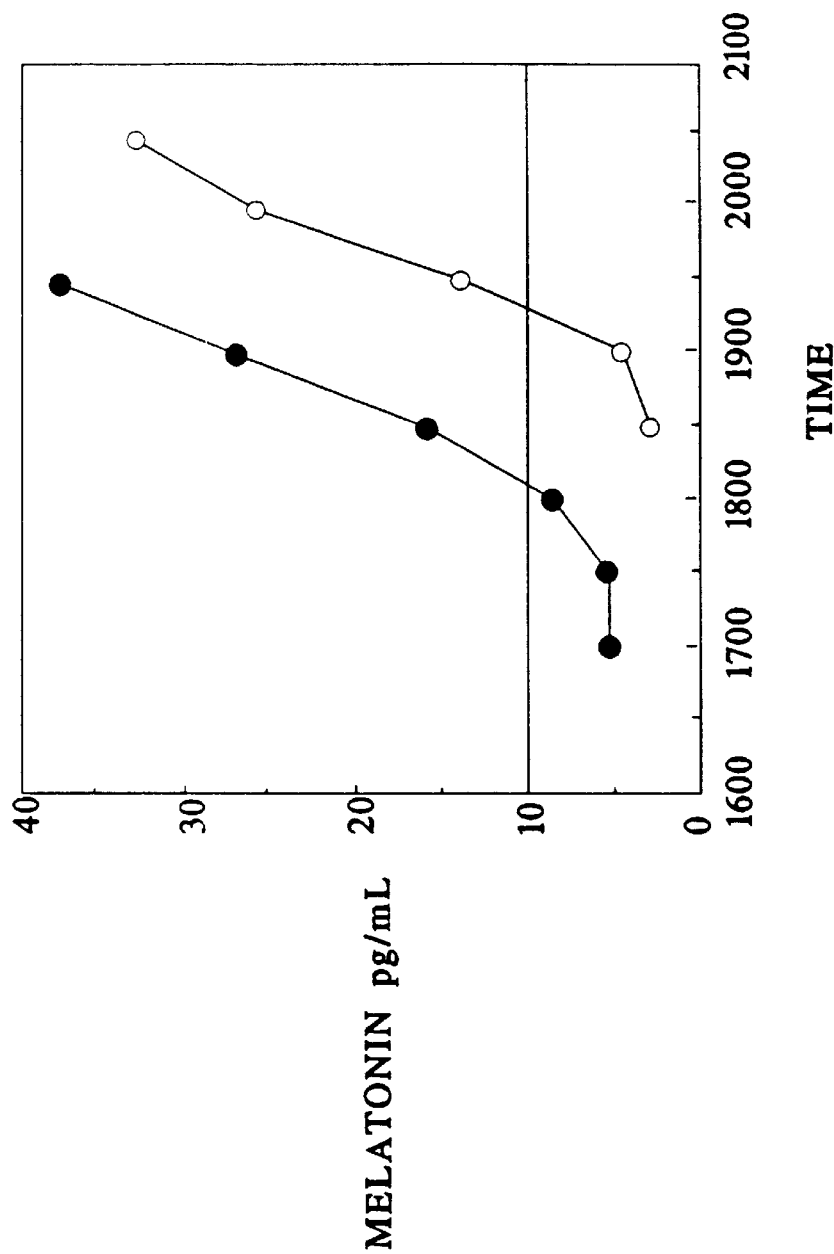

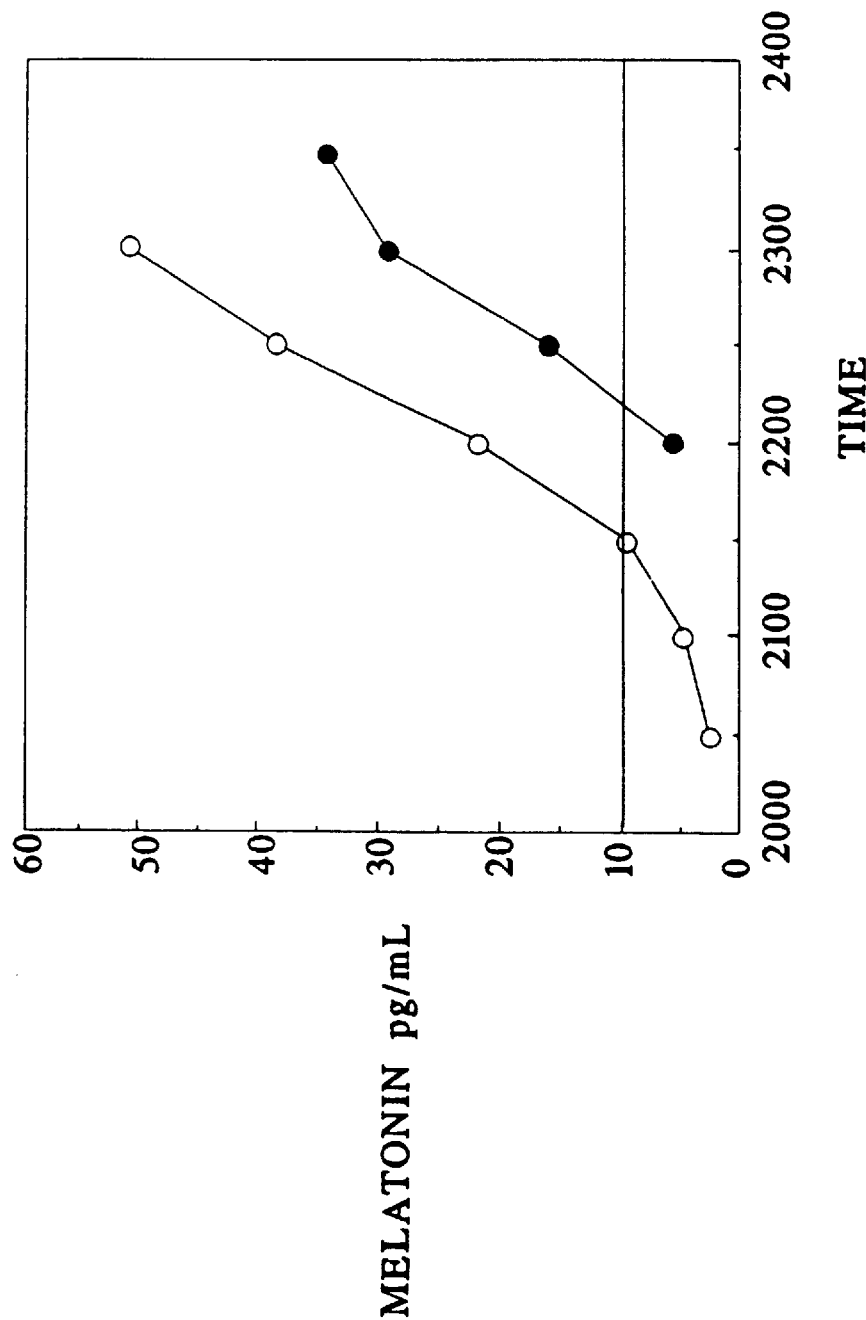

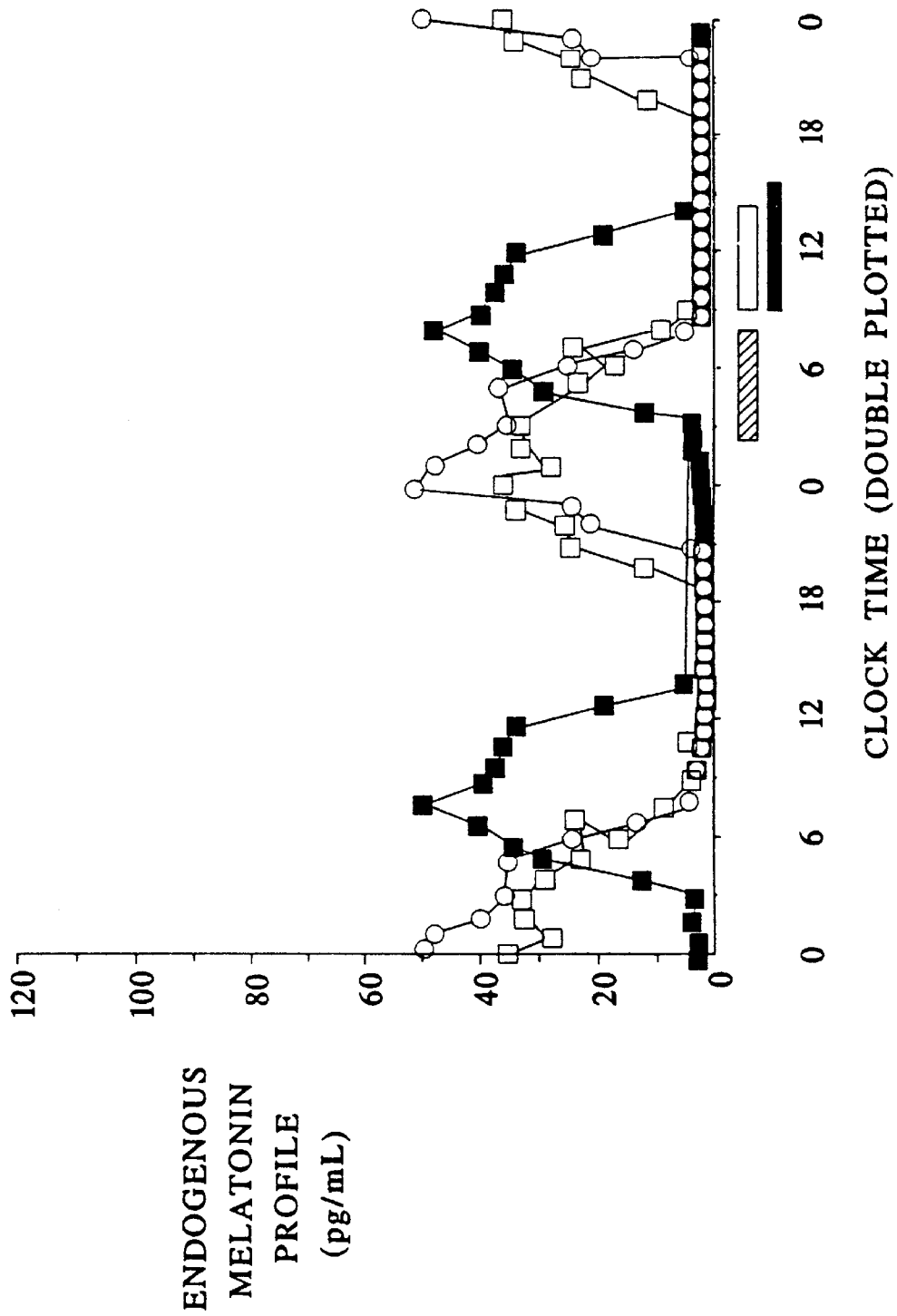

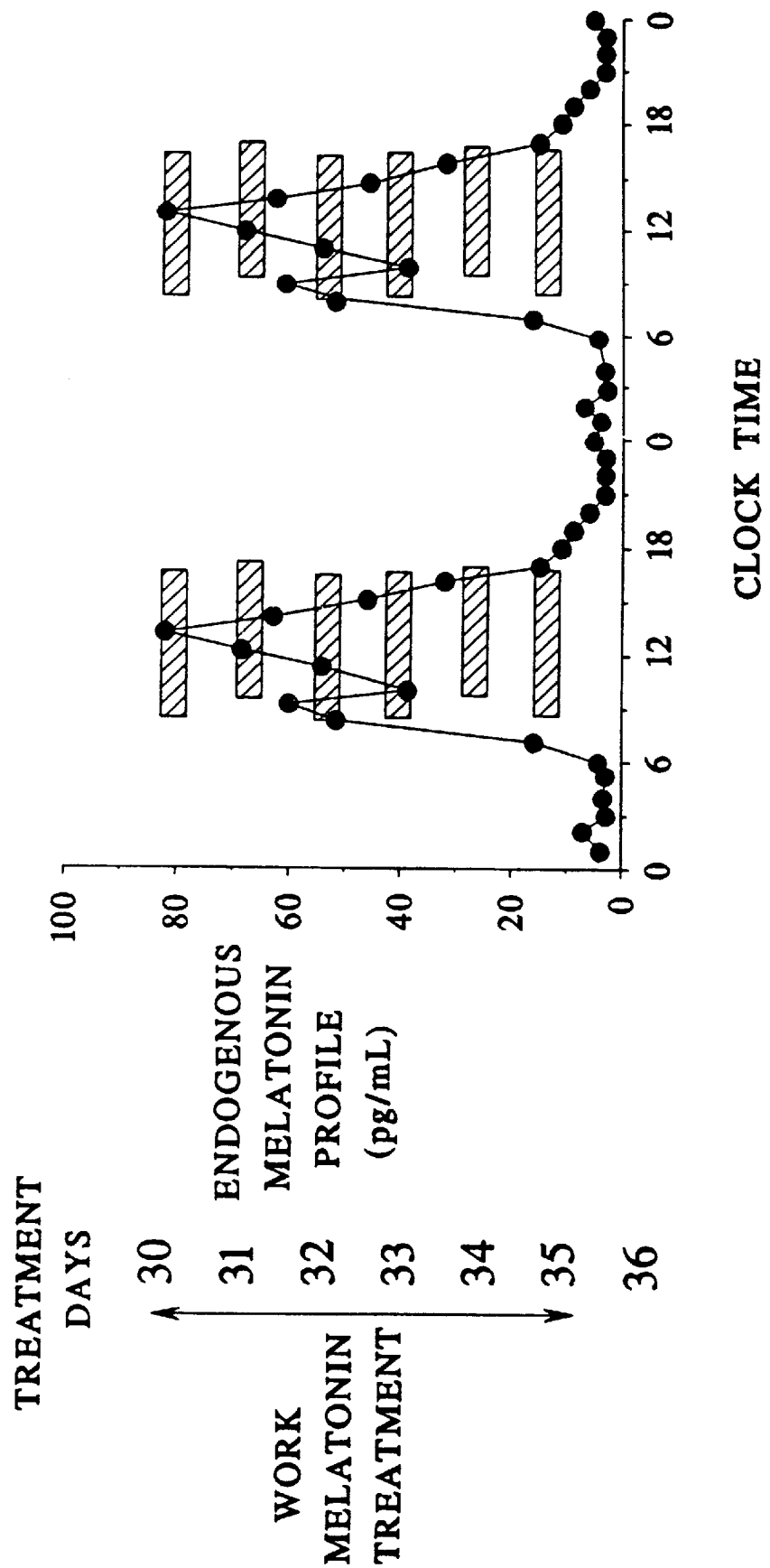

METHODS FOR TREATING CIRCADIAN RHYTHM PHASE DISTURBANCES

This is a divisional of application Ser. No. 08/110,878, filed Aug. 24, 1993, now U.S. Pat. No. 5,591,768, which is a continuation-in-part of Ser. No. 07/842,723, filed Feb. 25, 1992, now U.S. Pat. No. 5,242,941, issued Sep. 7, 1993, which is a continuation of Ser. No. 07/621,866, filed Dec. 4, 1990, now abandoned.

BACKGROUND OF THE INVENTION

1. Field of The Invention

The field of the invention disclosed in this application relates to circadian rhythms in humans, and particularly to the synchronization of such human circadian rhythms with the external environment. Specifically, this invention describes methods for achieving a chronobiologic (circadian phase-shifting) effect in humans. The invention provides methods to specifically advance or delay the phase of certain circadian rhythms in humans. Specific embodiments of the invention comprise methods for alleviating the effects of transmeridional travel (i.e., jet lag); methods for alleviating circadian phase disturbance-based psychopathological disorders (such as winter depression or seasonal affective disorder); and methods for achieving synchrony between a human's wake/sleep cycle or other circadian rhythms and the human's occupational and other human activity schedules. Such re-synchrony enabled by the methods of this invention is achieved by the administration of effective amounts of melatonin at specific and predictable times based upon an individual human's circadian rhythm phase response curve (PRC).

2. Background of The Related Art

The phenomenon of circadian rhythms in biology is well known, and circadian rhythms are exhibited by all eukaryotic plants and animals, including man. Biological rhythms are periodic fluctuations in biological properties over time; these include circadian as well as seasonal variations. Circadian, or approximately 24-hour, rhythms include the production of biological molecules such as hormones, the regulation of body temperature, and behaviors such as wakefulness, sleep and periods of activity.

In nature, circadian rhythms are closely tied to environmental cues that impose a 24-hour pattern on many of these fluctuations. Experimental inquiry has established that when these cues are absent, most circadian rhythms have a periodicity of approximately 25 hours. Circadian rhythms that are not regulated by environmental cues are said to be free-running. The regulation of circadian rhythms by signals from the environment is said to involve entrainment of the circadian rhythm. The environmental signals that affect entrainment have been termed zeitgebers, an example of which is the light-dark cycle.

It is thought in this art that the control of circadian rhythms in mammals is mediated by a portion of the brain called the superchiasmatic nuclei (SCN). Circadian rhythms are primarily entrained by the light and dark cycle: light signals are conveyed by the retina to the SCN, and the pineal gland produces melatonin (N-acetyl-5-methoxytryptamine), which is regulated by the SCN.

Disruption of circadian rhythms can result in a number of pathophysiological states in humans; the most common of these is jet lag. The use of melatonin to ameliorate the effects of jet lag has been described in the prior art.

U.S. Pat. Nos. 4,665,086 and 4,600,723 teach the use of melatonin to alleviate the symptoms of jet lag. These patents teach the use of 1–10 mg of melatonin, taken at destination bedtime, and again upon premature awakening in the middle of the night. In view of the fact that such large dosages of melatonin are known to exert a soporific (sleep-inducing) effect, and further that external zeitgebers such as the light/dark cycle also act to re-entrain the circadian rhythm of a human's sleep/wake cycle following transmeridional flight, it is not clear whether melatonin is capable of directly causing any change in the circadian rhythm of endogenous melatonin production when it is administered according to the teachings of these patents.

Gwinner and Benzinger, 1978, J. Comp. Physiol. 126: 123–129 teach that daily injections of melatonin can entrain the activity/rest cycle in birds.

Arendt et al., 1984, Neurosci. Lett. 45: 317–325 and Arendt et al., 1985, CIBA Found. Symp. 117: 266–283 disclose that melatonin in high doses increases tiredness and the tendency to sleep in humans.

Underwood, 1986, J. Pineal Res. 3: 187–196 discloses a PRC for melatonin in the lizard *Sceloporus occidentalis*.

Arendt et al., 1987, Ergonomics 30: 1379–1393 disclose the administration of melatonin to alleviate jet lag by oral administration of exogenous melatonin 4 to 6 hours prior to the human's normal bedtime and upon awakening in the middle of the night.

Mallo et al., 1988, Acta Endocrinol. 119: 474–480 teach that the administration of 8 mg of melatonin to humans, one hour before bedtime over a course of four days, results in a slight phase in the melatonin rhythm advance three days after cessation of the melatonin treatment but not in other circadian rhythms.

Armstrong et al., 1989, Experientia 45: 932–938 disclose that in rats the effects of exogenous melatonin administration on the circadian rhythm of the sleep/wake cycle depends on the time of administration relative to the sleep/wake cycle, and that the effect was greatest when exogenous melatonin was administered a few hours before the effective start of the nocturnal activity cycle. However, these authors were unable to demonstrate phase-delay shifts or graded changes in magnitude of phase-advance shifts, nor did and they relate the timing of exogenous melatonin administration to the time of the endogenous melatonin onset.

Petrie et al., 1989, Br. Med. J. 298 705–707 teach the administration of 5 mg of melatonin to humans on a schedule of three days before flight, during flight, and once a day for three days after arrival to alleviate jet lag caused by flights from Auckland, New Zealand to London and back.

Skene et al., 1989, Sleep '88 (J. Horne, ed.), pp. 39–41 teach the use of melatonin to treat jet lag.

Samel et al., 1991, J. Biol. Rhythms 6: 235–248 teach the use of melatonin for the treatment of jet lag using an administration schedule of melatonin administration at 1800 hr local time for 3 days before the time shift, and at 1400 hr local time for 4 days afterwards.

Nickelsen et al., 1991, Adv. Pineal Res. 5: 303–306 teach the administration of 5 mg melatonin at destination bedtime for the treatment of jet lag resulting from 6, 9 and 11 hour time-shifts.

Claustrat et al., 1992, Biol. Psychiatry 32: 705–711 teach the use of melatonin to affect circadian rhythms.

Entrainment and regulation of the ciradian rhythms have been demonstrated in a number of animal species. The ability to effect an actual change in phase of the circadian rhythm would be useful for the alleviation of a number of circadian-rhythm related disorders.

Lewy and Sack, U.S. patent Ser. No. 5,242,941, issued Sep. 7, 1993 to the present inventors, was the first disclosure of a phase-response curve for melatonin in humans. This reference shows that the appropriate time to administer melatonin to induce a change in phase of a variety of human circadian rhythms is related to the time of dim light melatonin onset (DLMO). Contrary to the rather simplistic view held by the prior art (i.e., that melatonin was simply associated with darkness, which came to be thought of as being equivalent to sleep in diurnal animals), this patent disclosure established that the circadian rhythm of endogenous melatonin production was tightly coupled to the endogenous circadian pacemaker that regulates the timing of a variety of other human circadian rhythms (such as core body temperature, cortisol and sleep propensity), and that affecting the phase of the human melatonin circadian rhythm by administration of exogenous melatonin could produce both phase advances and phase delays in human circadian rhythms. A particularly novel teaching of this patent disclosure was that the magnitude and direction (i.e., phase advance or phase delay) of the desired circadian rhythm phase shift was dependent on the time of melatonin administration that resulted in the desired circadian rhythm phase-shifting effect. Again contrary to the established teachings of the prior art, this patent prescribed administration of non-soporific dosages of melatonin at times that (usually) were not equivalent to destination bedtime, based on the human melatonin phase response curve (PRC). The teachings of this patent are hereby expressly incorporated by reference.

The human melatonin PRC clearly shows that melatonin acts like darkness on the circadian rhythm of the wake/sleep cycle in humans. Sleep alone has been found to have little if any chronobiologic effect in humans; however it is possible that sleep may potentiate the phase-shifting effects of melatonin and darkness. Melatonin is produced in humans only during nighttime darkness and not during daytime darkness, suggesting that melatonin may act by helping the endogenous circadian pacemaker to discriminate between the nighttime dark period and sporadic episodes of daytime darkness (including daytime sleep). Melatonin in combination with dim light thus might be a more effective darkness zeitgeber than darkness alone in the absence of melatonin.

The human melatonin PRC described in U.S. patent Ser. No. 5,242,941 suggested that exogenous melatonin would be most effective when administered during the light period, to compete with light as a "substitute for darkness". The present invention is based on our further findings that the critical variable in determining the proper time for melatonin administration is the relationship between the time of melatonin administration and the DLMO time of an individual human. This finding has provided the basis for the methods of the instant invention, which methods enable treatment of a variety of circadian rhythm phase disturbances in humans by administration of exogenous melatonin at the times described hereinbelow.

SUMMARY OF THE INVENTION

This invention relates to methods for achieving a chronobiologic (phase-shifting) effect in a human. This effect is achieved by affecting a human's circadian rhythm by administering exogenous melatonin to the human at an appropriate time relative to the human's dim light endogenous melatonin onset time.

The circadian rhythm of melatonin production in a human is entrained principally by the (bright) light-dark cycle and reflects a variety of other biological properties which vary with a circadian rhythm. The methods of the invention entail the phase-shifting of the circadian rhythm by administration of exogenous melatonin. More specifically, the method of the invention involves the administration of a particular dosage of melatonin to the human. The present invention contemplates the administration of various doses of melatonin which promote quantitative shifts in an individual's endogenous circadian pacemaker. The administration of sufficient doses of melatonin is capable of shifting the pacemaker, as well as the melatonin PRC by an appropriate degree. A linear dose effect has been found as described hereinbelow at melatonin dosages from about 0.125 mg to about 0.5 mg melatonin. Thus, in a preferred embodiment, melatonin is administered in dosages preferably from about 0.05 to 5 mg, more preferably from about 0.1 to 2 mg, and most preferably from about 0.1 to 1 mg. In a preferred embodiment, the total dose of melatonin is given in one dose.

The present invention also contemplates the use of melatonin precursors, agonists, antagonists, and compounds which mimic melatonin activity, in place of melatonin (N-acetyl-5-hydroxytryptamine) itself.

Further, the method of the invention relates to the timing of the administration of the dosage of melatonin to the human. The timing of this dosage in the human as described results in a specific phase shift in the human's circadian rhythm of endogenous melatonin production. The method described in the invention can be used to advance or delay the phase of the circadian rhythm of melatonin production in the human. In this way, the present invention is able to alleviate circadian rhythm disorders of both the phase-delay and the phase-advance types.

The present inventors have discovered that the time of administration of exogenous melatonin relative to the time of endogenous melatonin onset is critical to the production of the appropriate phase-shifting effect. The time of exogenous melatonin administration is kept constant relative to the human's DLMO time, which changes during a course of exogenous melatonin treatment as provided by the methods of the invention. Thus, the actual clock-time of melatonin administration also changes during the course of melatonin treatment using the methods of this invention. The time of endogenous melatonin onset, termed the dim light melatonin onset (DLMO) time, will vary in each individual human; however, the DLMO occurs at about 9 o'clock PM (circadian time (CT) 14) for most diurnal humans. Since the actual times of exogenous melatonin administration as provided by the methods of the instant invention are dependent on the time of an individual human's dim light melatonin onset (DLMO) time (which will vary for each individual), circadian time will be used to most effectively represent almost all times discussed in this specification.

The present invention is based on the melatonin phase-response curve (PRC; see U.S. patent Ser. No. 5,242,941 and Example 2 below). The human melatonin PRC, shown in FIG. 1, indicates the presence of a time interval for each individual during which administration of exogenous melatonin results in clear and unequivocal phase-advance responses. Within this interval, the time of administration of melatonin is related to the magnitude of the resulting phase advance shift of the PRC. The human melatonin PRC also indicates the presence of a time interval for each individual during which administration of exogenous melatonin results in clear and unequivocal phase-delay responses. Within this interval, the time of administration of melatonin is related to the magnitude of the resulting phase delay shift of the PRC. The present invention directs the administration of melatonin to achieve phase advances between about CT 3 to about CT 18, and to achieve a phase delay between about CT 12 to about CT 6. The predicted phase advance or phase delay is more likely if the melatonin administration time occurs within these two intervals, respectively. The methods of the invention also take into account the additional fact that the zones for phase advance and phase delay overlap (i.e., between about CT 2 and CT 6 and also between about CT 12 and CT 19), as shown in FIG. 1.

The invention also relies on the identification of more precise intervals of melatonin administration times wherein the intervals of phase advance and phase delay responses do not overlap. For a phase advance, this unequivocal melatonin administration interval ranges from about CT 7 to about CT 11. For a phase delay, the melatonin administration interval is from about CT 20 to about CT 2.

The methods of the present invention thus provide for the administration of exogenous melatonin to effect a phase advance or a phase delay in the endogenous melatonin PRC. Preferred times of melatonin administration to effect a phase advance are about CT 3 to about CT 18, more preferably about CT 7 to about CT 11, most preferably about CT 7 to about CT 8. Preferred times of melatonin administration to effect a phase delay are about CT 12 to about CT 6, more preferably about CT 20 to about CT 2, and most preferably at about CT 0.

It will be understood by those with skill in this art that the methods of this invention thus prescribe exogenous melatonin administration times which will change relative to clock time during the course of exogenous melatonin treatment to effect a circadian rhythm phase shift. One novel and important aspect of the instant invention is that exogenous melatonin administration times are predicted relative to an internal circadian rhythm marker, the DLMO time, rather than external markers such as clock time (e.g., "destination bedtime"). This aspect enables the instant invention to provide methods for achieving circadian rhythm phase-shifting effects that result in the effective treatment of a variety of circadian rhythm phase disturbances. In preferred embodiments, such circadian rhythm phase disturbances include jet lag, winter depression and shift-work and other human activity schedule-related disorders and de-synchronies with external zeitgebers.

Also contemplated as components of the methods of the instant invention are embodiments wherein melatonin administration is accompanied, either at administration times coincident with melatonin administration times or at appropriate times other than melatonin administration times, by exposure of a human to bright light, either artificial or naturally-occurring, or by limiting such exposure, that is, by prescribing the use of dark or red-colored goggles or other means to prevent a human from exposure to a light stimulus. Appropriate combinations of exogenous melatonin administration, dim light or bright light treatments are provided by this invention, as described more fully below.

Specific preferred embodiments of the present invention will become evident from the following more detailed description of certain preferred embodiments and the claims.

BRIEF DESCRIPTION OF THE DRAWINGS

FIGS. 9A and 9B illustrates the phase shifts achieved using the melatonin administration protocols of Example 5 to alleviate jet lag; wherein open circles indicate DLMOs in the subject when administered 0.5 mg melatonin and filled circles indicate DLMOs in the subject when administered 5 mg melatonin

FIGS. 16A through 16F shows melatonin profiles and sleep time of six night shift workers obtained using the methods described in Example 7;

FIG. 19A through 19D illustrates plasma melatonin and sleep times for shift worker BD; wherein crosshatched bars indicate sleep times and duration; the subjects underwent a two week hiatus between experiments resulting in the data shown in FIGS. 19A and 19B and the experiments resulting in the data shown in FIGS. 19C and 19D

DETAILED DESCRIPTION OF THE PREFERRED EMBODIMENTS

The amount of melatonin administered to a human subject should be sufficient to achieve the desired circadian rhythm phase-shifting effect. In a preferred embodiment of this invention, a dosage of about 0.1 mg to about 1 mg, most preferably about 0.25 mg–0.5 mg, of exogenous melatonin is used to effect the desired change in phase of the circadian rhythm of endogenous melatonin production. In a preferred embodiment, the total dose of melatonin is given in one administered dose.

Pharmaceutical quality melatonin is commercially available. Since melatonin appears to be absorbed across almost all tissues, many routes of administration are possible. These include but are not limited to submucosal, sublingual, intranasal, ocular, cul-de-sac rectal, transdermal, buccal, intravenous, intramuscular, and subcutaneous methods of administration. A variety of administration means, including but not limited to capsules, tablets, suppositories, repositories, injections, transdermal or transbuccal patches, or any reservoir capable of containing and dispensing melatonin, are also useful. In a preferred embodiment of this invention, melatonin is administered orally.

It may also be advantageous to administer melatonin in formulations wherein the melatonin is continuously released physiologically for a set time (e.g., sustained-release formulations), or in formulations wherein the physiological release of melatonin is delayed (e.g., delayed release formulations), or in combinations thereof. The present invention encompasses the use of such melatonin formulations in the methods of the instant invention.

In a preferred embodiment of this invention, a phase advance or phase delay in the circadian rhythm of endogenous melatonin production is effected by the administration of an amount of exogenous melatonin sufficient to achieve the phase advance or delay based upon the actual phase response curve of the individual, or the predicted phase response curve of the individual, or on their actual or estimated DLMO time. A phase advance in the circadian rhythm of endogenous melatonin production is effected by the administration of an effective dose of melatonin between about CT 3 to about CT 18, more preferably between about CT 7 to about CT 11, most preferably from about CT 7 to about CT 8. A phase delay in the circadian rhythm of endogenous melatonin production is effected by the administration of an amount of exogenous melatonin sufficient to achieve the phase delay at administration times from about CT 12 to about CT 6, more preferably from about CT 20 to about CT 2, most preferably at about CT 0.

Figure 1:
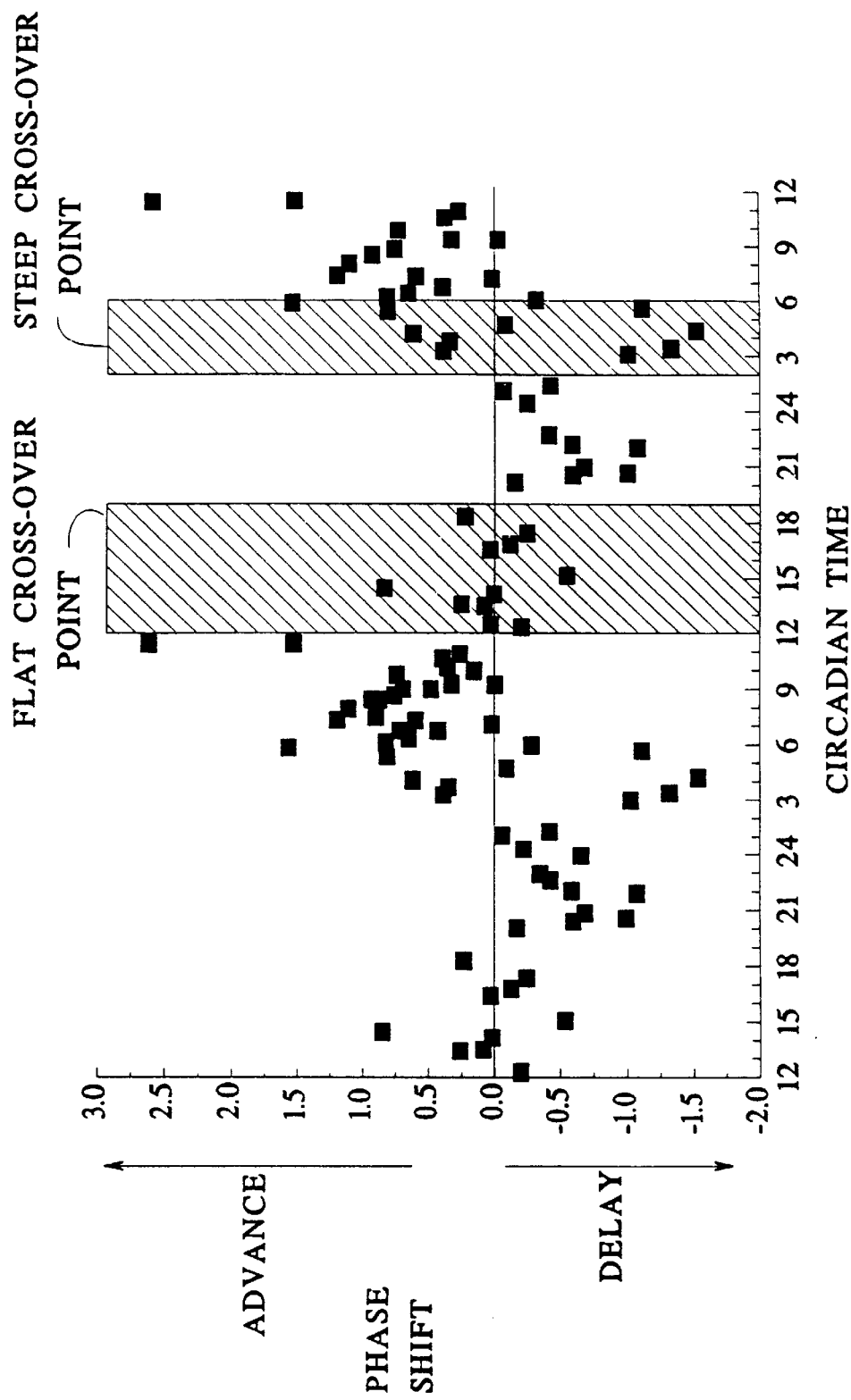
FIG. 1 illustrates a double-plotted human phase response curve, wherein the right-hand plot also represents the flat cross-over point between CT 12 and CT 19 and the steep cross-over point between CT 2 and CT 6.

In a newly-appreciated aspect of the human melatonin PRC, there are found overlapping and non-overlapping areas between the advance and delay zones (as seen in FIG. 1); this characteristic results in "narrow" and "broad" intervals in which the effect of the timing of melatonin administration on the production of either a phase advance or phase delay is less critical in the latter versus in the former. There are also regions of reduced responsiveness towards exogenous melatonin, termed "dead zones", between the phase advance and phase delay portions of the PRC (see FIG. 1). The cross-over point in the "narrow" dead zone between advance and delay phase-shifting regions of the melatonin PRC separates phase shifts of the greatest magnitude, whereas the cross-over point in the "broad" dead zone between advance and delay phase-shifting regions of the melatonin PRC separates phase shifts of lesser magnitude. Consequently, it is possible to prescribe melatonin administration times based on either the broad overlapping zones or narrow exclusive zones. It is also possible to view the decision on which set of administration times to prescribe as being a conservative approach, in which one wants above all else to avoid shifting a person in the wrong direction. The conservative times of melatonin administration are about CT 7 to about CT 14 for phase advances and about CT 22 to about CT 2 for phase delays. Use of this conservative approach may require a user to be willing to settle for a smaller phase shift. Using a more aggressive approach, on the other hand, exogenous melatonin administration times closer to the steep cross-over point in the melatonin PRC can be chosen, resulting in the possibility of achieving larger phase shifts. However, this aggressive approach also carries the risk that a phase shift will be effected in the direction opposite to the desired direction, and may be an inappropriate strategy for many applications of the methods disclosed herein (see Examples below).

At least for phase advances, the beginning of the exogenous melatonin stimulus pulse should be used as the reference phase for administration time. As compared with the human PRC disclosed in U.S. Ser. No. 5,242,941, the current embodiment of the human melatonin phase response curve is shifted about one hour earlier, because most of the administration times therein disclosed were taken to be the average of the times of administration of a split dose of melatonin.

The easiest way to estimate circadian times are relative to "sleep offset", which is equal to the time of awakening for humans awakening to sunshine or other bright light. For humans who awaken before dawn, sleep offset is the time of their dawn exposure to sunlight, or more accurately a short time thereafter, since even sunlight is fairly dim light right around dawn.

This time is taken to be equal to CT 0. For most humans, the average time of dim light melatonin onset (DLMO) is 14 hours later, or at CT 14. For conversion back to clock time, CT 14 is on average 9 p.m., for the average person who awakens at 7 a.m.

A modification of the method of Lewy and Markey (1978, Science 201: 741–3) may be used to determine the time of onset of the patient's endogenous melatonin production. The preferred use of this method is taught in Example 1.

Determination of circadian time is done optimally using the DLMO time. However, in some individuals (who have very low melatonin production, encompassing less than 10% of the population) determination of the entire melatonin curve may be preferable, or alternatively, an algorithm can be applied to correct the circadian time of the DLMO. Determination of the entire melatonin profile may be preferred in some individuals for other reasons known to those with skill in the art as well.

Other markers for circadian time are also useful, for example sleep onset (bedtime) or sleep offset (wake time), see above and in some cases these markers are more convenient than the DLMO time. There are also other physiological markers that may be used, such as the core body temperature minimum or the rising limb of the cortisol circadian rhythm. These markers are more or less tightly coupled with each other, whereas other markers such as the sleep rhythm (which may be influenced by social cues and other homeostatic factors) are somewhat less tightly coupled (although the sleep propensity rhythm is tightly coupled).

The present invention may be used in, but is not limited to, the following situations to achieve chronobiologic effects and/or to alleviate circadian rhythm phase disorders: jet lag; shift work; people who have a maladaptation to work and off-work schedules; astronauts in orbit around the Earth, on missions in space to the Earth's moon or to the planets or out of the known solar system, or in training for such missions; submariners, or persons confined for research, exploration or industrial purposes below the seas; miners, explorers, spelunkers, researchers or those confined beneath the Earth; psychiatric patients; insomniacs; the comatose, or those who need to be maintained in a state of unconsciousness for medical, psychiatric or other reasons; medical residents, nurses, firemen, policemen or those whose duties require alertness and wakefulness at evening or nighttime hours, or those deprived of sleep for various periods because of their duties or responsibilities; the infantry, or other members of the armed forces whose duties require extreme levels of alertness and wakefulness, and who may be sleep deprived in the performance of these duties; the blind or sight-impaired, or all those whose ability to distinguish differences in light and dark may be permanently or temporarily impaired; residents of the far North or Antarctica, or all those who live in a climate or climates that possess abnormal amounts of light or darkness; those suffering from seasonal affective disorder, winter depression, or other forms of depression; the aged; the sick, or those who require dosages of medication at appropriate times in the circadian cycle; and animal breeders, for use in controlling circadian time. Five types of insomnia can also be helped by melatonin administration. One, termed pure insomnia, is not particularly related to a circadian phase disturbance. Two are known to be circadian rhythm-related insomnias: advanced sleep phase syndrome (ASPS) and delayed sleep phase syndrome (DSPS). There are also two types of mixed insomnias, termed pure insomnia plus ASPS and pure insomnia plus DSPS.

The present invention provides methods useful in the treatment of jet lag, winter depression, maladaptation to work/off-work schedules or any of the other above-listed conditions, under direct medical supervision, wherein melatonin administration times are chosen pursuant to a determination of the actual DLMO time for an individual. Other such instances include patients whose PRC must be specifically determined, or where the use of melatonin precursors, analogs agonists or antagonists require a more precise determination of dose and timing of exogenous melatonin administration. Examples of such instances include individuals whose response to melatonin treatment, or absorption or metabolism of melatonin or melatonin agonists, antagonists or precursors may vary from the normal response, thereby necessitating medical supervision.

In another embodiment of the invention, melatonin administration can be performed directly by an individual without medical supervision. For such uses, times of exogenous melatonin administration can be prescribed, for example in a table, instructing the individual to take melatonin at specific times based upon normal bedtime and waking time and the magnitude and direction of the desired phase shift. For example, the use of the methods herein described to alleviate the effects of jet lag can advantageously be enabled by an article of manufacture comprising melatonin in a consumer-accessible formulation, accompanied by charts or tables setting out proper times of exogenous melatonin administration based on the number of time zones crossed in travel and the direction of travel, either based on characteristically "normal" human DLMO times or with reference to any other indicia of an individual's actual DLMO time. In other such specific embodiments of the invention, melatonin may be administered in time-release formulations that are geared to release melatonin in conjunction with the number and direction of time zones crossed, releasing the melatonin at the proper times. Such articles of manufacture and melatonin formulations are expressly within the scope of the instant invention.

Preferred embodiment of the methods of this invention encompass melatonin administration times based upon an individual's PRC and DLMO time. Administration times are prescribed relative to the DLMO time, which will change with re-adjustment of an individual's melatonin PRC (accompanied by re-synchronization of the individual's circadian rhythms with the external environment). According to the methods of this invention, the magnitude and direction of the desired circadian rhythm phase shift are dependent on melatonin administration times and the pattern and direction of the change in the clock time of such administration times with adaptation of the melatonin circadian rhythm.

One example of the teachings of the instant invention embodying the aspects of the timing of exogenous melatonin administration and the change in the clock time of melatonin administration times that accompanies the shift in the melatonin PRC is shown in Table I. The Table illustrates the predicted times of exogenous melatonin administration for alleviating jet lag. As can be seen from the Table, the time of melatonin administration depends on both the magnitude and the direction of the desired phase shift. Also shown in the Table is the change in melatonin administration times during the course of melatonin treatment, wherein the melatonin administration time remains constant relative to the DLMO time (which changes in response to the melatonin PRC shift). This Table is based on our finding that the appropriate shift (conservatively estimated) in exogenous melatonin administration times in jet lag alleviation protocols is at least about one hour per (dose).

Generally speaking, the timing of exogenous melatonin administration can be safely estimated as described above, or specifically determined by diagnostic testing. In practice, these approaches can be employed seriatim, i.e., one can start by using sleep onset or offset (i.e., awakening) time as a marker for circadian time. In cases where this estimate proves to be unsatisfactory, a more reliable physiological marker, such as the DLMO time, can be determined. Alternatively, the nighttime melatonin profile can be obtained by testing blood, urine, saliva or other body fluid for the presence of melatonin or physiological or metabolized products thereof. The easiest way to estimate an individual's circadian time is relative to the time of sleep offset (awakening) corresponding to "bright lights on", as described above.

It is contemplated that in some cases, it may be necessary to empirically determine a rather highly defined PRC for an individual in order to know exactly when to administer medication optimally. For most people, however, general rubrics can be used based on average characteristics or on the average correlation between observable circadian rhythm markers (such as wakefulness and sleep) and melatonin and other more occult human circadian rhythms. An example of the utility of such generalized methods is the jet lag-related table of proper administration times described above (Table I).

Melatonin administration times are optimally adjusted on a daily basis for methods used to accomplish large (i.e., greater than a total of 1 hour) shifts in the melatonin PRC. This can be advantageously and conveniently achieved using a melatonin delivery system that is formulated to release melatonin on schedule, i.e., so that the melatonin can be released to act at a time that changes daily, although the time of administration of the melatonin formulation does not change. For convenience, a delayed-release melatonin preparation would be optimal, particularly if the formulation resulted in increased physiological melatonin levels of short duration. Such advantageous controlled-release melatonin preparations would not only be capable of sustaining physiological melatonin levels at a desired level for desired period of time, but would also enable such physiological availability to commence and cease at fairly precise times. For example, as described more fully hereinbelow, an optimal delayed-release melatonin formulation could be used in the treatment of either shift workers or air travellers, whereby physiological melatonin levels would be increased at a slightly different time each day, so that an individual would only need remember to take the formulation at the same time of day.

It is also possible to formulate melatonin delivery systems that can produce a sustained physiological level (i.e., sustained-release formulations) over a period of time corresponding to a selected interval of the individual's circadian rhythms. This form of therapy could be used to shift the PRC without necessitating repeat administration of melatonin by the individual. In some individuals, a broader pulse width of melatonin covering the widest possible zone, for either the conservative or aggressive approach of treatment, to produce the appropriate phase shift would be desirable.

Melatonin can also be administered in combination with scheduling bright light administration, ordinary-intensity light exposure, or exposure to dim-light or darkness (or even sleep). In one embodiment of this aspect of the invention, melatonin administration using the methods disclosed herein is accompanied by having an individual wear dark or red goggles at the time of melatonin administration, to provide for the additive effects of the combination of melatonin treatment plus darkness. In another embodiment of this aspect, the individual wears dark goggles at times including times other than the time of melatonin administration to avoid the occurrence of a conflicting external zeitgeber in opposition to the phase shift promoted by the exogenous melatonin administration protocol.

Similarly, bright light exposure can be used along with the exogenous melatonin administration methods provided herein. One aspect of the usefulness of this embodiment is for the bright light-mediated suppression of endogenous melatonin production when such endogenous melatonin production occurs at the "wrong" time, i.e., at a time relative to the PRC which would be antagonistic to the desired phase shift.

Inappropriate endogenous melatonin production can also be suppressed pharmacologically using a number of pharmaceutical agents, including but not limited to noradrenergic and serotonergic re-uptake blockers, alpha-1- noradrenergic agonists, monoamine oxidase inhibitors, beta-adrenergic blockers and benzodiazepines. It may also be desirable to suppress part of the endogenous melatonin profile, for example, by causing receptor super-sensitivity; by removing endogenous melatonin from stimulating the undesirable part of the melatonin PRC; or to eliminate potentiating effects of a competing melatonin or darkness (sleep) signal. One example of this embodiment (described in more detail below in Example 6) is the use of atenolol plus a very low dose of melatonin (0.125 mg) in the treatment of winter depression. Atenolol is given at about CT 14 and low-dose melatonin at CT 8. Atenolol blocks endogenous melatonin production during the delay zone (which promotes a phase advance), and it also induces super-sensitivity to the melatonin administered at CT 8. It is also noted that patients taking such drugs for other clinical reasons can be expected to have circadian rhythm side effects, so that it is advantageous to work a compensatory adjustment in their melatonin levels to avoid unwanted phase shifts.

Certain other drugs (tricyclic antidepressants and alpha-2-adrenergic antagonists, for example) can raise endogenous melatonin levels, particularly at night. This side effect will also affect an individual patient's "biological clock" in ways predicted by the melatonin PRC.

Melatonin precursors such as tryptophan, 5-hydroxytryptophan, serotonin and N-acetylserotonin may also affect endogenous melatonin levels and circadian rhythms, including the melatonin PRC, either via their conversion to melatonin, or by the direct action of these compounds on melatonin receptors in the SCN. Such influences are predictable using the melatonin PRC, adjusted to account for absorption time, metabolic conversion rates, etc.

Phase-shifting effects of melatonin analog/agonists can also in like manner be predicted by the melatonin PRC. The phase-shifting effects of melatonin antagonists, on the other hand, are somewhat more complex, because these effects depend on whether a particular antagonist acts directly on melatonin receptors in the SCN or whether such antagonists act to block endogenous melatonin activity. However, in either case their effects can be predicted by the melatonin PRC, once the effects of absorption time, etc., are taken into account.

It will be understood by those with skill in the art that, as a consequence of the existence of the melatonin PRC (first disclosed in U.S. patent Ser. No. 5,242,941, issued Sep. 7, 1993 and incorporated herein by reference), any administration of exogenous melatonin will potentially cause a melatonin PRC phase shift (unless said administration time falls within one of the "dead zones" of relative insensitivity of the PRC to the effects of exogenous melatonin). Melatonin administration performed in ignorance of such effects on an individual's PRC runs the risk of causing inappropriate melatonin PRC phase shifts, which may act contra to the physiological effect intended to be produced by said melatonin administration. Thus, it is evident from the present disclosure and the teachings of U.S. Pat. No. 5,242,941 that an individual's melatonin PRC must be understood and taken into account whenever exogenous melatonin is administered to a human.

These considerations become especially important in the treatment of certain circadian rhythm-related pathological disorders. For example, because of the simultaneous existence (co-morbidity) of insomnia not related to phase disturbances and phase-related sleep problems, melatonin pulses may have to be carefully crafted to stimulate a certain zone of the melatonin PRC and to avoid stimulation of other zones, as well as to take advantage of any soporific side effects associated with administration of pharmacological dosages of melatonin. For example, in the treatment of delayed sleep phase syndrome, a physiological dose should begin at about CT 7–8, then increase to a pharmacological dose just before bedtime (about CT 14–16) and end before any delay responses begin, at about CT 17–19. For pure insomnia (no phase disturbance) any dose of melatonin that would promote sleep would also be potentially able to cause a phase shift (although the low phase-shifting doses do not necessarily cause sedation) and therefore these phase shifts must be avoided. There are two ways to do this: one way is to give melatonin exclusively at the dead zone, that is between about CT 14–18. The other way is to give melatonin sufficiently early to cause a phase advance that will balance out any phase delay caused by its administration during sleep.

For some individuals, optimal phase advancing would be accomplished by having the exogenous melatonin pulse continuous with the offset of endogenous melatonin, and optimal phase delaying would be accomplished by having the exogenous melatonin pulse continuous with the onset of endogenous melatonin. The possible combinations of melatonin dosages and administration times are flexible enough to allow individually-tailored treatments as needed, but all treatments have in common the feature of being tied to intervention based upon the melatonin PRC.

Melatonin Administration Under Medical Supervision

A certain portion of the human population falls outside of what is considered the "normal" human characteristics of drug absorption, or ability of circadian rhythms to adapt or respond to melatonin treatment. These individuals may require a more accurate determination of their individual PRC before attempting intervention. Other individuals who may be suffering from pathological or clinical circadian rhythm phase disorders may also benefit from a more accurate detemination of DLMO before intervention. In a controlled setting, under medical supervision, a more precise and specific intervention of the melatonin PRC can be accomplished using the methods of the present invention to effect predictable phase advances or delays.

Under medical supervision, a subject can have their DLMO time determined carefully by sampling physiological levels of melatonin in blood, saliva or other biological fluids. The concentration of melatonin can be determined analytically using methods including but not limited to gas chromatography-mass spectrometry (GC-MS), radioimmunoassay (RIA) or enzyme-linked immunosorbent assay (ELISA) methods. The advantage of medical supervision is to more accurately and exactly determine an individual's DLMO time and establish their melatonin PRC. This information then enables specific and precise intervention by exogenous melatonin administration for adjusting the DLMO time in a predictable manner.

Melatonin Administration By The Individual
A. Kit for determining DLMO.

Alternatively, for many individuals a less precise determination of their DLMO time will enable them to use the methods provided by this invention to effect a desired circadian rhythm phase shift based on an estimate of their DLMO time. A convenient means for allowing an individual to adjust the DLMO in a predictable manner and without medical supervision would involve the use of a simple home assay kit. This assay kit would allow the individual to determine his own DLMO time by sampling biological fluids at short intervals during the course of part of a normal day.

1. Dip Stick for Saliva

In one embodiment, the amount of melatonin or melatonin metabolite in the individual's saliva could be assayed simply by applying a saliva sample to an applicator stick designed to react with melatonin or melatonin metabolite in a concentration dependent fashion. The individual could compare the assay sticks contacted with saliva over a period of time, and use an interpreting means (such as a color comparison strip) to determine the approximate DLMO time. Once an individual had determined his DLMO time, tables or other instruction means based on the DLMO time and providing a schedule of exogenous melatonin administration times for achieving a desired phase shift could be used to inform the individual when and how much melatonin to take to achieve the desired phase shift.

2. Blood drop test

In another embodiment, an individual could use a drop of blood to assay for the physiological concentration of melatonin or melatonin metabolite, similar to methods currently in use for determining blood levels of sugar or cholesterol. This assay means would result in a qualitatively similar but quantitatively more accurate determination of the individual's DLMO time compared with the previously-described dip stick method, and would be useful for applications of the methods of the invention wherein more accurate estimates of the DLMO time are required.

B. Fixed Dose Melatonin Formulations

In the simplest formulations, melatonin is provided as fixed dose pharmaceutical compositions. Such compositions and means for making such compositions are well known in the art. Fixed dose formulations provide a predictable phase shift in a "normal" individual when administered using the methods of the invention herein disclosed. Clock time for melatonin administration depends on the magnitude and direction of the desired shift, and the DLMO time of the individual.

1. Based on an individual's actual DLMO time

An accurately-determined DLMO time for an individual can be determined by medical assay, or by the home assay methods disclosed above. The administration times appropriate for obtaining the desired shift result are then predicted by the melatonin PRC. The times and dosages of exogenous melatonin administration provided by the present invention may be used to achieve the desired phase shift.

2. Based on an individual's estimated DLMO time

In many instances, the magnitude of the desired phase shift, or the magnitude of an individual's desire for the phase shift (i.e., whether phase shifting is medically-necessary e.g., in winter depression patients) or simply a matter of convenience (e.g., jet lag)), may permit the administration of melatonin based upon an estimated DLMO time. This can be done by using the position of an individual's typical wake time and sleep times as being about CT 0 and CT 16, respectively. Using exogenous melatonin administration schedules based on such rough estimates of the DLMO time allow very general intervention and adjustment of the DLMO. Such interventions are best accomplished using lower doses of melatonin administered over a wider period of time, to encompass most of the estimated advance or delay portion of the PRC without overlapping with the region of the PRC specifying a phase shifting effect opposite to the desired effect. Methods using estimated DLMO times are particularly applicable for alleviating circadian rhythm phase disturbances caused by transmeridional travel, shift work and other manmade circadian rhythm desynchronizations of human circadian rhythms.

C. Timed Release Melatonin Formulations

Melatonin formulations can be designed to administer the dose of melatonin slowly over a period of time at a fixed rate, quickly at a specific time after the taking of the formulation, or at any other combination of release times and rates. Such formulations can be made by those with skill in the pharmaceutical arts.

1. That shift release time over the period of administration.

A novel feature of the present invention is the use of melatonin administration times that remain constant relative to the DLMO time, and change relative to clock time as the melatonin PRC undergoes a phase shift. However, this feature necessitates that melatonin be taken at different times during the administration protocol, and this feature may make the methods undesirably inconvenient in practice. In order to facilitate ease of use, formulations of melatonin can be designed which can be taken at the same time each day, but which will release melatonin at different times and rates. These formulations can be selected so that the timing of physiological activity of administered melatonin coincides with the times predicted by the melatonin PRC for achieving a desired phase-shifting effect, even though the clock time at which the individual takes melatonin does not change during the course of treatment. In one embodiment, such melatonin formulations could be dispensed in a kit much like birth control pills are currently dispensed, with specific formulations being administered in sequence to achieve the daily shift of administration time without requiring the individual to vary daily administration times.

2. That are of fixed time of release but can vary in dosage

The linear relationship between phase shift and melatonin dose has been demonstrated (see Example 6). This suggests that formulations of melatonin that release varying doses of melatonin may be useful; methods for making such formulations are known in the art. The use of different dose formulations can also be used in combination over the period of administration. Such an administration format would allow shifting of circadian rhythms, including the melatonin PRC in individuals having unique requirements, for example, due to work schedule, disease, personal reaction to melatonin, life style, or other factors.

3. That shift release time and released dosage

Melatonin formulations that release different doses at different release times may also be useful. Such formulations would permit the melatonin dose and time of physiological action to be varied, while still being convenient to use. Use of such formulations would enable administration of sustained, low levels of melatonin to achieve the desired phase shift, while avoiding the soporific side-effects of large doses of melatonin during desired hours of alertness. Similarly, sustained low-level release of melatonin during desired hours of alertness can be followed by release of higher levels of melatonin during desired sleep times to enhance the phase-shifting effect.

D. Simplified Administration Schedule

Depending on the desired result, the schedule of administration of melatonin, the dose, type of formulation, and period of administration are all variables that can be altered to suit individual requirements. These variables can also be simplified for the type of administration desired, so that the average person can use kits providing appropriate melatonin formulations and instructions on their use to effect the desired melatonin phase shifts.

The simplest form of instruction would be a look-up, cross-indexed table referenced to the DLMO time, that would allow an individual to pick the amount of phase shift desired and the correct melatonin dose and administration times to effect the desired phase shift.

1. Jet Lag

For example, jet lag can be efficiently and effectively treated using the teachings of the invention. An individual can use either his estimated DLMO time or a kit-derived estimate of his DLMO time (or even a medically-supervised DLMO time determination) to identify his DLMO time at a time prior to travel. This information can then be used as the baseline DLMO time for intervention. The direction of travel will determine whether a phase advance or a phase delay is desired, and the number of time zones travelled will determine the magnitude of phase shift required to ameliorate the effects of jet lag on the individual. Melatonin can then be administered using human melatonin PRC-derived schedules, exemplified by Table I, to achieve the desired phase shift. The choice of formulation taken can be varied, so that the exact methods of melatonin administration will conform to individual needs. Integrated kits providing melatonin formulations and administration protocols can be provided to alleviate jet lag caused by transmeridional flight travelling to and returning from any destination.

2. Winter Depression

A small shift in an individual's DLMO time (about 0.5 hour) has been found to be capable of vastly improving psychological ratings of winter depression in patients suffering from this disorder (see Example 6 below). These results indicate that simple formulations of melatonin capable of effecting such small phase shifts in DLMO time would be useful to individuals suffering from winter depression. Since only a small melatonin phase shift is required, individuals could use estimated DLMO times to determine the appropriate time of exogenous melatonin administration. However, preferred embodiments of this method would also encompass accurate, medically-supervised determinations of the DLMO time, as the inappropriate administration of melatonin to winter depressives has been found to exacerbate the symptoms of winter depression in some such patients. Melatonin formulations, doses, times and duration of administration can be tailored to the needs of individual patients.

3. Maladjustment to Work Schedule

In individuals who must adjust their work schedule to fit reversals from normal environmental zeitgebers (such as night-shift workers), melatonin administration can effect a phase shift resulting in adjustment to the new sleep cycle. Melatonin administration protocols can be used based on estimated DLMO times in such individuals, but more accurate determinations of DLMO times are preferred. Melatonin formulations for treatment of these individuals can be tailored for convenience to result in the desired phase shift without causing unwanted soporific side effects.

The following Examples describe certain specific embodiments of the invention. However, many additional embodiments not described herein nevertheless fall within the spirit and scope of the present invention and claims.

EXAMPLE 1

Detection of Melatonin Levels in Human Plasma using Gas Chromatography-Mass Spectrometry Prior to collection of human blood, subjects were kept in dim light for about 5 hours (usually between 6 PM and 11 PM). An intravenous line or heparin lock was inserted in a forearm vein and 5 ml of blood were drawn every 30 minutes between 7 PM and 11 PM. The blood samples are centrifuged for 5 minutes at 1000 g and 4° C., and the plasma aspirated into a silanized glass or plastic tube. Samples are assayed immediately or frozen for later analysis. To a 1 ml aliquot of such plasma was added 15–40 picograms of N-acetyl-5-methoxy($\alpha,\alpha,\beta,\beta$-D$_4$)tryptamine as a chromatographic control. An equal volume of normal saline is added and the mixture gently shaken with 10 volumes of petroleum ether. The organic phase is removed, and melatonin and the added N-acetyl-5-methoxy($\alpha,\alpha,\beta,\beta$-D$_4$)tryptamine control extracted from the aqueous phase with 10 volumes of chloroform. The aqueous phase is then discarded, and the chloroform evaporated to dryness.

The dried extract containing melatonin and the added N-acetyl-5-methoxy ($\alpha,\alpha,\beta,\beta$-D$_4$)tryptamine control is dissolved in 0.4 ml of anhydrous acetonitrile. The melatonin contained in the plasma samples and the added N-acetyl-5-methoxy($\alpha,\alpha,\beta,\beta$-D$_4$)tryptamine control are then derivatized by the addition of 25 µl of pentafluoropropionic acid anhydride and 0.5 ml of a solution of 5% trimethylamine in anhydrous benzene and reacted at 100° C. for 10 minutes. The reaction products were washed sequentially with 1 ml water and 1 ml 5% ammonium hydroxide. The mixture is centrifuged briefly at 13,000 g and the organic phase withdrawn and evaporated to dryness under nitrogen. The dried extract is partitioned between 0.5 ml acetonitrile and 1 ml hexane by vigorous mixing followed by centrifugation. The hexane layer is removed and the acetonitrile evaporated to dryness under nitrogen. This partitioning step is performed two times for each sample. The dried extract is re-partitioned for storage. The derivatives are stable and can be stored at −20° C. for several weeks.

The amount of melatonin present in each sample is determined by analysis using a gas chromatograph-mass spectrometer (GC-MS). Before injection onto the GC column, the dried derivatives are dissolved in 15 µl of ethyl acetate. Approximately half this volume was applied to a 30 m×25 µm fused silica capillary column (0.15 micron film thickness with a 1 m retention gap (DB-225, J&W Scientific, Folsom Calif.). The oven is programmed from 60° C. to 240° C. (at 25.5° C./min) with helium as carrier gas (10 psi head pressure) and methane used as make-up gas (ionizer, 0.6 torr). Derivatized melatonin and the added N-acetyl-5-methoxy ($\alpha,\alpha,\beta,\beta$-D$_4$)tryptamie derivatized control are found to elute from the column after 10–14 minutes. Mass spectrographic analysis of the column eluant is then performed. Mass spectra are recorded using a Finnigan 4000-GC-CI analyzer and INCOS data system. A Finnigan PPIMCI electron multiplier with 3 kV conversion was used, signal referenced to ground. The relative signals of melatonin and the added N-acetyl-5-methoxy($\alpha,\alpha,\beta,\beta$-D$_4$) tryptamine control are detected at mle (mass/charge) ratios of 320 and 323, respectively. The amount of melatonin present in any unknown sample can be determined by comparison of the ratio of the intensities of these signals to a standard curve, prepared as described using known amounts of melatonin and added N-acetyl-5-methoxy($\alpha,\alpha,\beta,\beta$-D$_4$)tryptamine control.

EXAMPLE 2

Phase Advance in the Human Melatonin Phase Response Curve

The effect of exogenous melatonin administration on circadian rhythms of sighted people was tested. Eight normal subjects were treated in a two-week protocol. During the first week, the subjects were given a placebo at 1700 and 1900 hours and their dim light melatonin onsets (DLMOs) were measured as described in Example 1. During the second week, subjects were given placebo at 1700 and 1900 hours for two days, and then melatonin was administered in two doses of 0.25 mg at 1700 and 1900 hours for 4 days and the subjects' DLMO determined.

Figure 2:
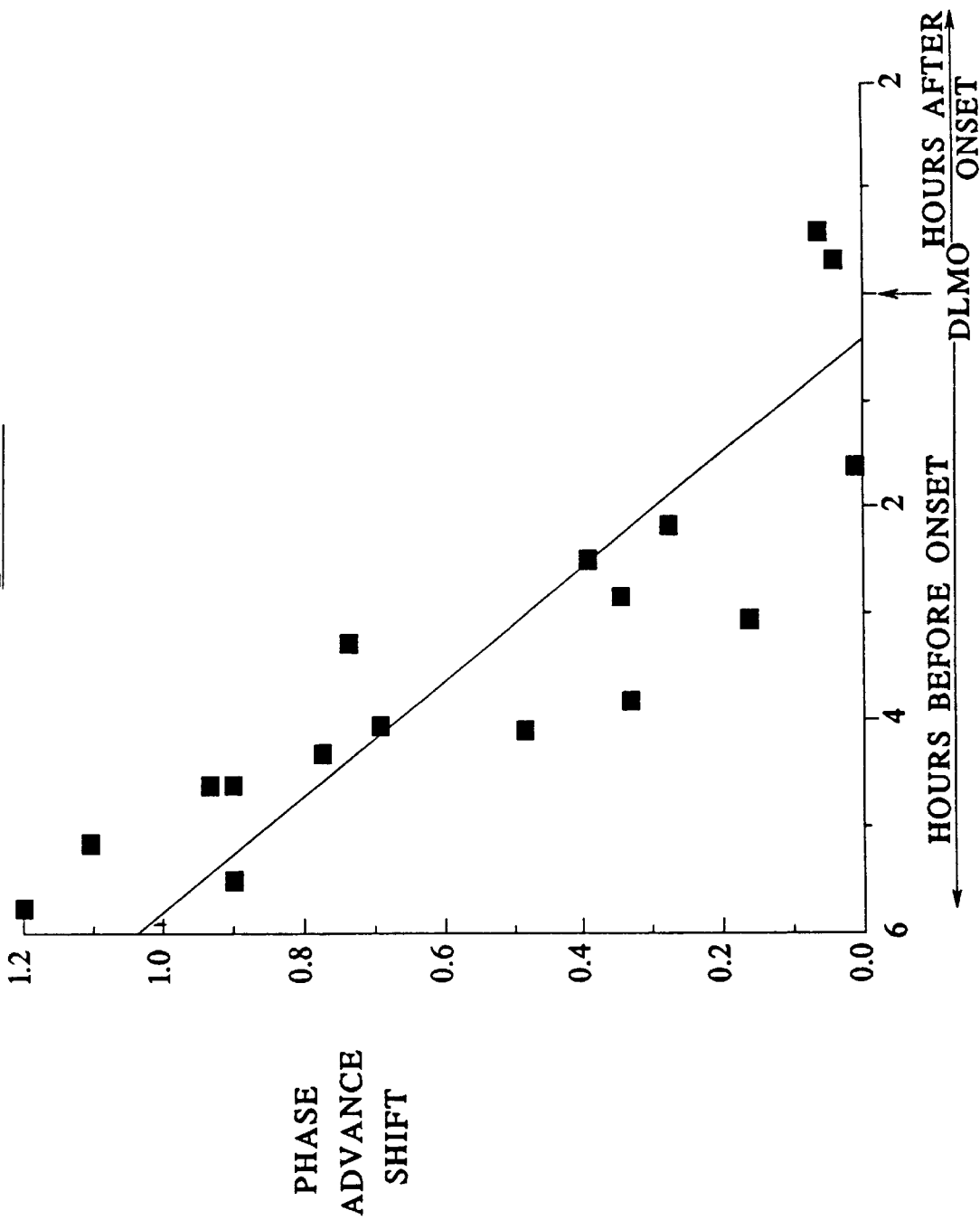
FIG. 2 illustrates the results of the experiment described in Example 2.

Seventeen trials were conducted on the eight subjects. The results of this study are shown in FIG. 2. The Figure defines the human melatonin phase response curve, showing the relationship between the degree of phase shift obtained and the interval between the time of administration of exogenous melatonin and the endogenous DLMO (this interval is also known as the phase angle). The earlier the exogenous melatonin is administered the greater is the magnitude of the phase advance; that is, there is a positive correlation between the extent of phase advance achieved by exogenous melatonin administration and the time interval between the time of exogenous melatonin administration and the time of endogenous melatonin onset. These results confirm that exogenous melatonin administration can effect a phase advance in humans, and that the timing of exogenous melatonin administration relative to the onset of endogenous melatonin is critically important for phase shifting circadian rhythms.

EXAMPLE 3

Relationship between Exogenous Melatonin Administration Time and DLMO Time

Figure 3:
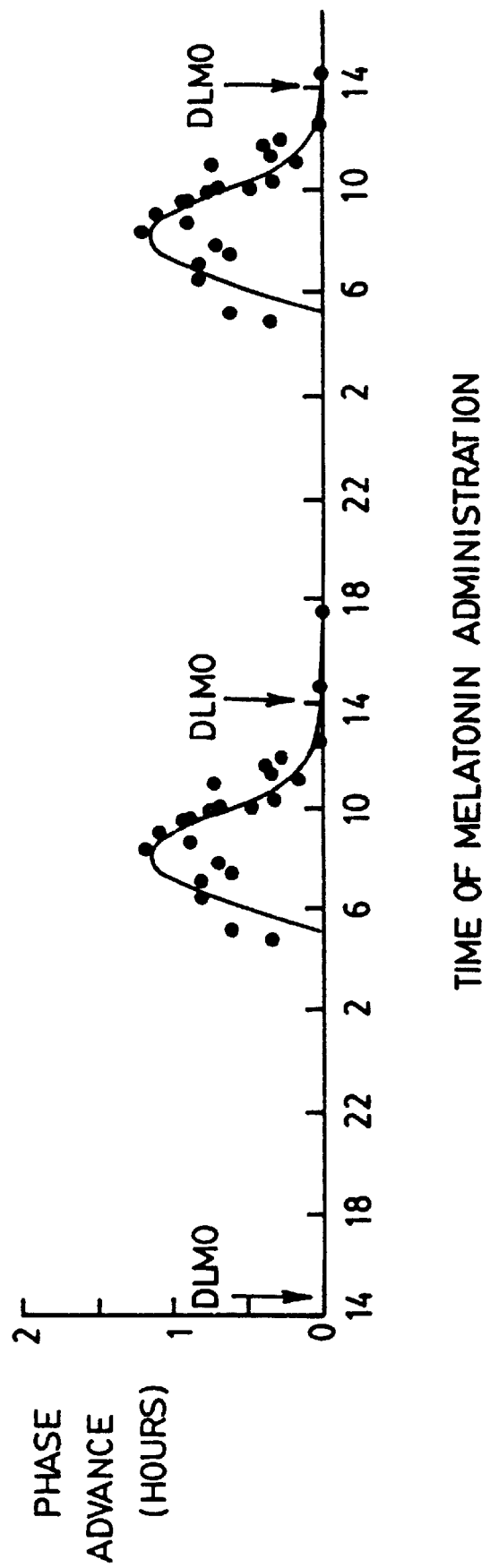
FIGS. 3 and 4 disclose the experimental results of Example 3.
Figure 4:
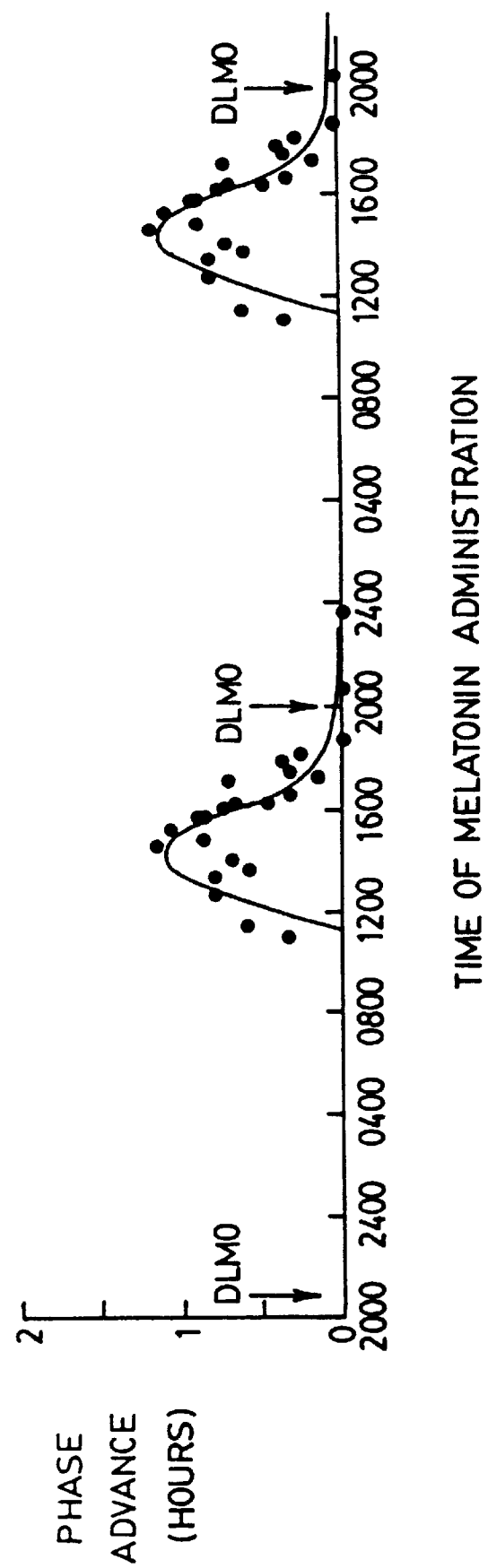

The effect of exogenous melatonin treatment administered at earlier times relative to the endogenous melatonin rhythm was tested in sighted people. Twenty-four trials, including those described in Example 2 were conducted in the eight normal subjects who were treated in a two-week protocol similar to the one used in Example 2. During the first week, placebo was administered and the time, extent and amount of dim light melatonin onset (DLMO) was determined. Subsequently in the second week, melatonin was administered at various times prior to the time of endogenous melatonin onset, and the subjects' endogenous melatonin onset was determined. The results of this study are shown in FIGS. 3 and 4. FIG. 3 expresses the results in terms of circadian time (assuming the DLMO occurs at circadian time (CT) 14);, and FIG. 4 expresses the same results in terms of military time (assuming that DLMO is at 2000 hours (8 PM)). These results show that the maximum degree of phase advance in the onset of endogenous melatonin occurred after administration of exogenous melatonin at CT 8, or 6 hours prior to the normal time of melatonin onset in the subjects (CT 14). This corresponds to a time of about 8–10 hours before normal bedtime in these subjects. The observed phase advance declines rapidly when exogenous melatonin is administered prior to CT 8. Between CT 8 and CT 14, the decline in the degree of phase advance is linear and proportional to the phase angle between time of administration and time of endogenous onset. Minimal effect, if any, on the circadian rhythm of endogenous melatonin onset is seen when the time of administration of exogenous melatonin coincides with the normal time of onset of endogenous melatonin (CT 14).

EXAMPLE 4

Phase Delay in the Human Melatonin Phase Response Curve

Figure 5:
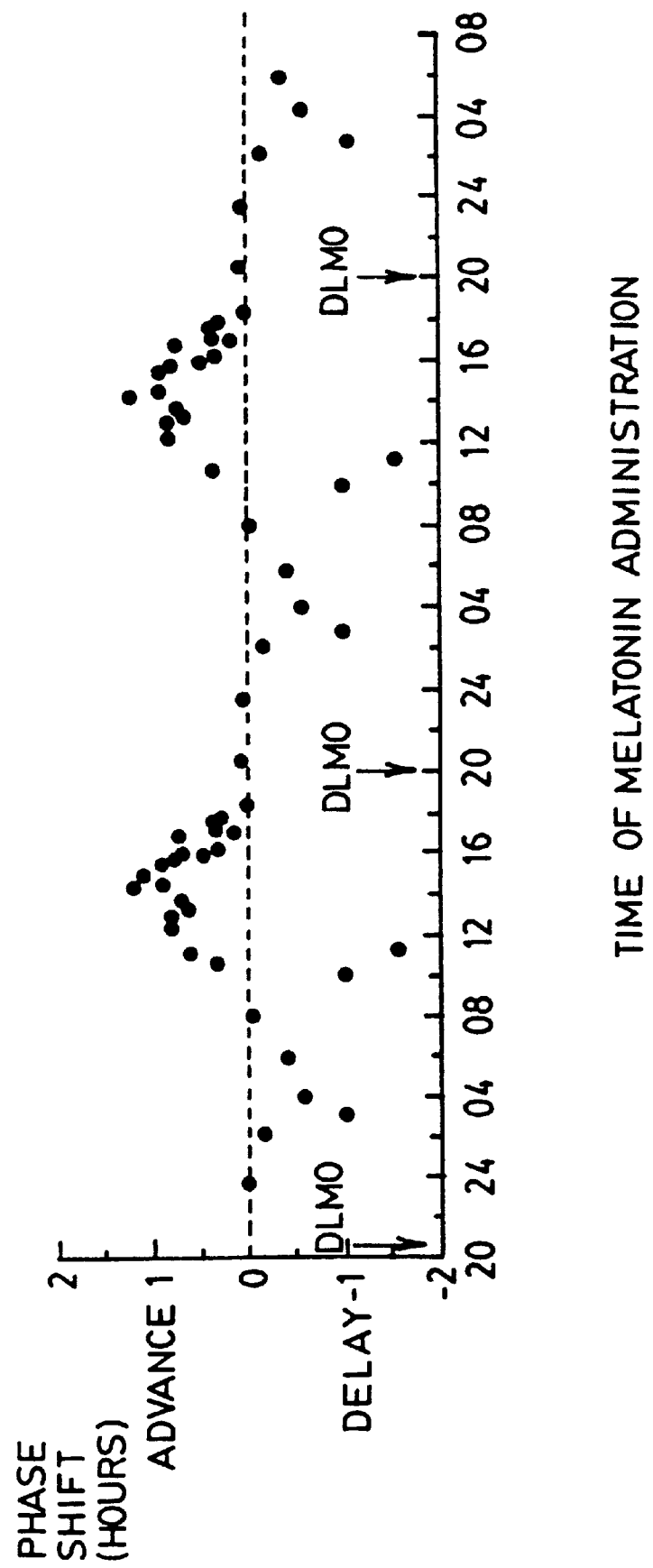
FIGS. 5 and 6 disclose the experimental results of Example 4.
Figure 6:
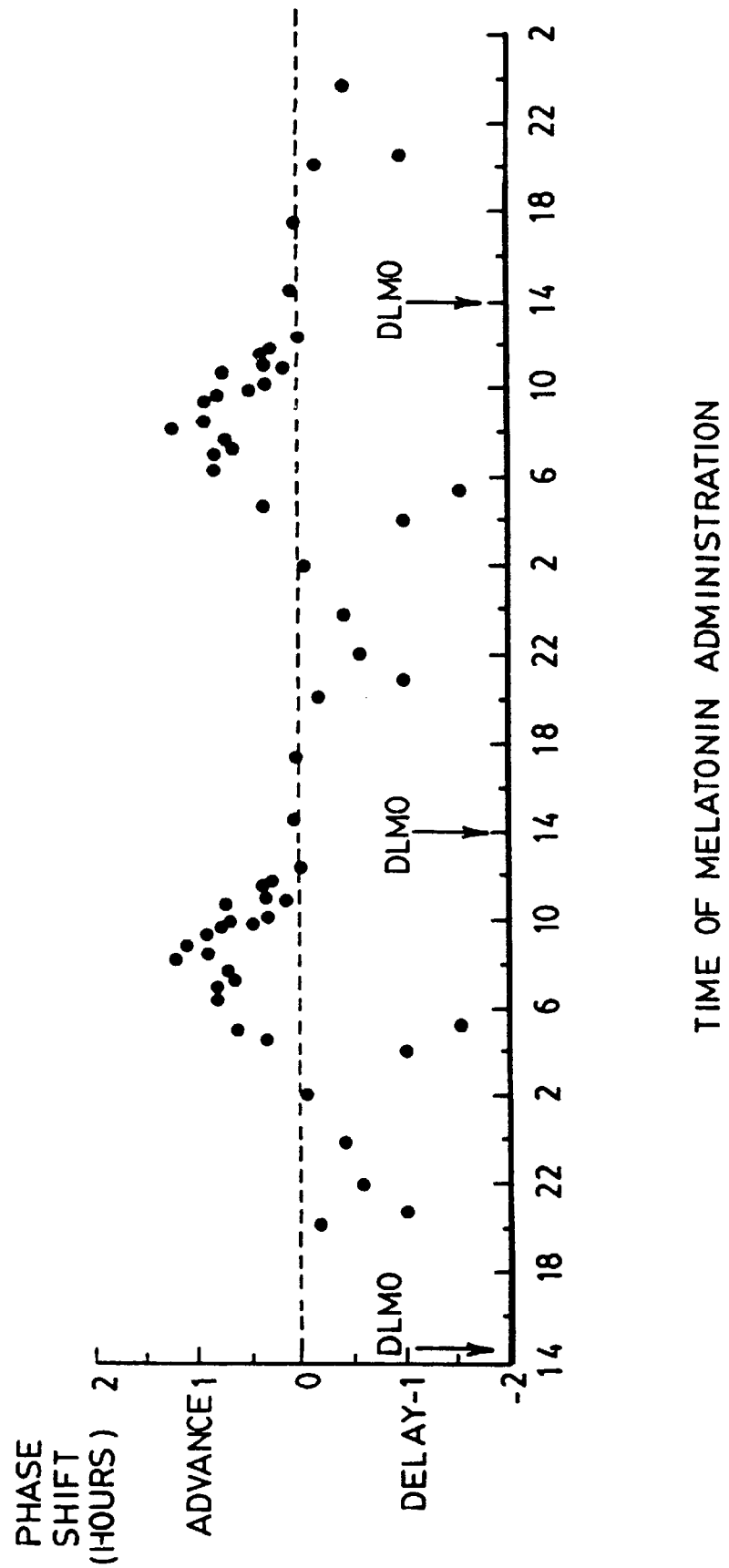

Experiments to investigate the use of exogenous melatonin to effect a phase delay were also performed. These experiments followed the protocol explained in Example 2; however, the time of administration of melatonin was different. A total of 6 trials (of the 30) were performed in the delay zone. The results of this experiment are shown in FIGS. 5 and 6. In this regime, exogenous melatonin was administered about 11–19 hours before normal bedtime. It was found that administration of exogenous melatonin from about 9 hours to about 17 hours before the endogenous melatonin onset resulted in the greatest degree of phase delay in the onset of endogenous melatonin production.

EXAMPLE 5

Melatonin Administration for Alleviating Jet Lag

A series of experiments were performed to illustrate the usefulness of the instant invention for alleviating jet lag in six subjects caused by transmeridional flight across three time zones in both the easterly and westerly directions. The six subjects were flown from Portland, Oreg., to Maui, Hi., remained there for 6 days and then were flown back to Portland. For each subject, the experiment was performed on two occasions, randomly ordered: once to illustrate the instant method, and a second time for comparison with methods of melatonin administration to alleviate jet lag known in the prior art.

During the experiment, the circadian rhythm of endogenous dim light melatonin onset (DLMO), a very accurate marker for body clock time, was determined physiologically by taking blood samples of the subjects every 30 minutes in dim light (<50 lux) in the evening on selected days. In addition, subjective impressions of chronobiological well-being were solicited from the subjects after concluding the experiment.

Figure 7:
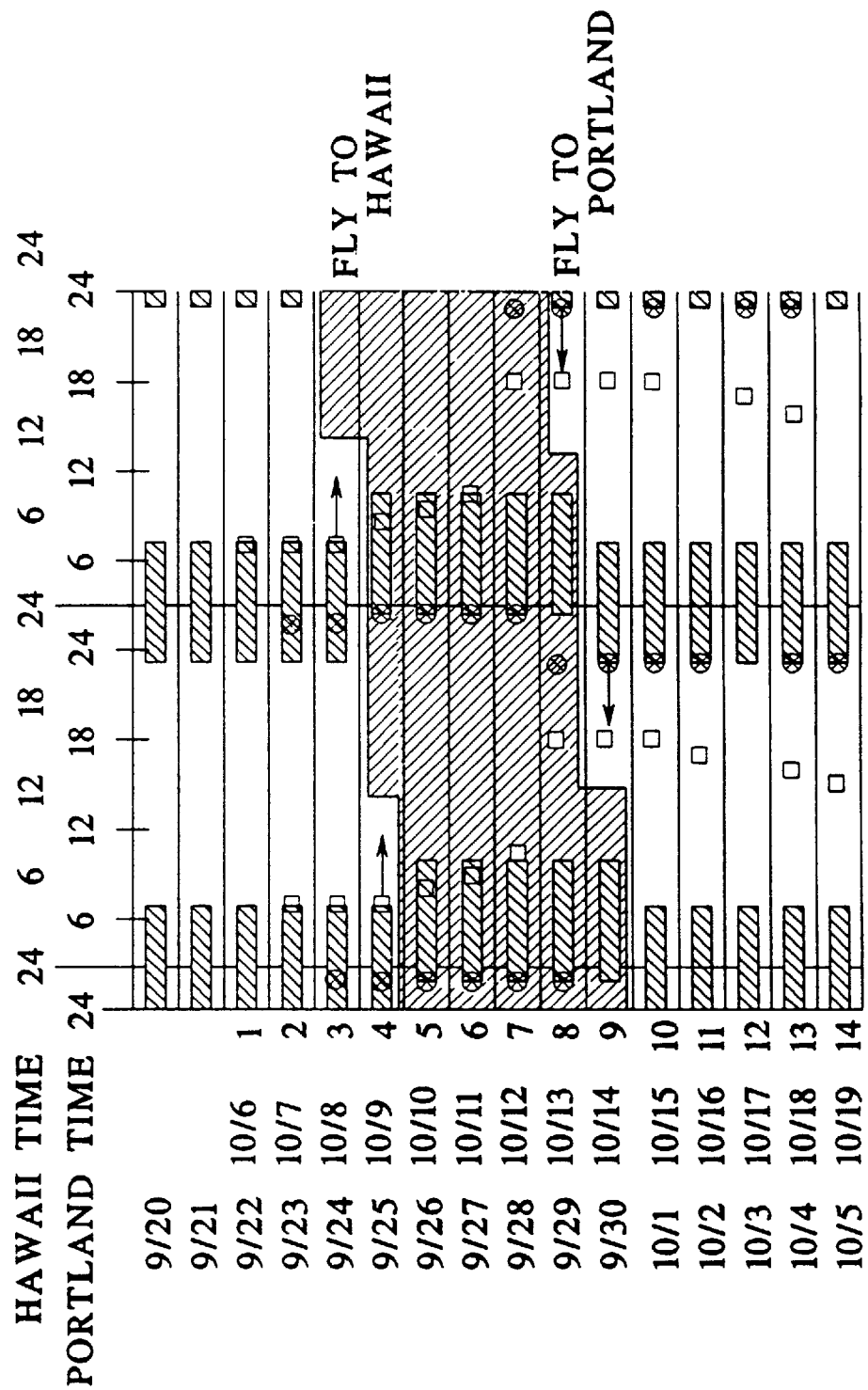
FIG. 7 illustrates a double plot of melatonin administration times for the protocol used to alleviate the effects of jet lag caused by airline travel between Portland, Oreg. and Maui, Hi. as described in Example 5; wherein the open squares indicate 0.5 mg melatonin administration times and the crossed circles indicate 5 mg melatonin administration times

FIG. 7 shows the experimental protocol for travel. The dark shaded bars denote scheduled sleep time. The lightly shaded area represents the time spent in Hawaii. The black boxes indicate administration times of 5 mg melatonin according to the teachings of the prior art, while white boxes indicate administration times of 0.5 mg melatonin according to the teachings of the instant invention. The time of 5 mg melatonin administration using the prior art teachings was the same at each administration (i.e., destination bedtime), while the time of 0.5 mg melatonin administration using the instant invention differed from the prior art administration times in two distinct ways. First, the time of administration was not linked to destination bedtime for travel across three time zones (although it should be recognized that the time established by the instant invention as the appropriate time for melatonin administration may coincide with destination bedtime at some destinations). Second, the time of melatonin administration changed over the course of the experiment, as the circadian rhythms, including the melatonin PRC, were expected to adjust to local time.

The subjects were given melatonin in the appropriate dosages for each experiment before and after travel, as well as on the day of travel from Portland to Hawaii and back for a total of six (6) days for each direction of travel. Under each experimental protocol, subjects were not aware of what dose of melatonin was being administered to them. In addition, when subjects were given melatonin according to a given protocol (i.e., the prior art administration times or the instant invention administration times), they were also given placebo capsules at the times when the alterative protocol called for melatonin administration, and subjects were not aware of when they were receiving melatonin and when they were receiving placebo.

The time of administration of 0.5 mg melatonin required to have the desired chronobiological effect was predicted from the endogenous PRC of the individual, and depended on the number of time zones crossed in the experiment. Table I illustrates the predicted time of initial melatonin administration depending on the direction of travel and the number of time zones crossed between place of origin and destination. In addition, the clock time of melatonin administration changed over the course of the experiment, as the circadian rhythms, including the melatonin PRC, were predicted to become adjusted to the local conditions. The subjects were given melatonin in the appropriate dosages before and after travel, as well as on the day of travel, for a total of six days for each direction of travel.

Figure 8:
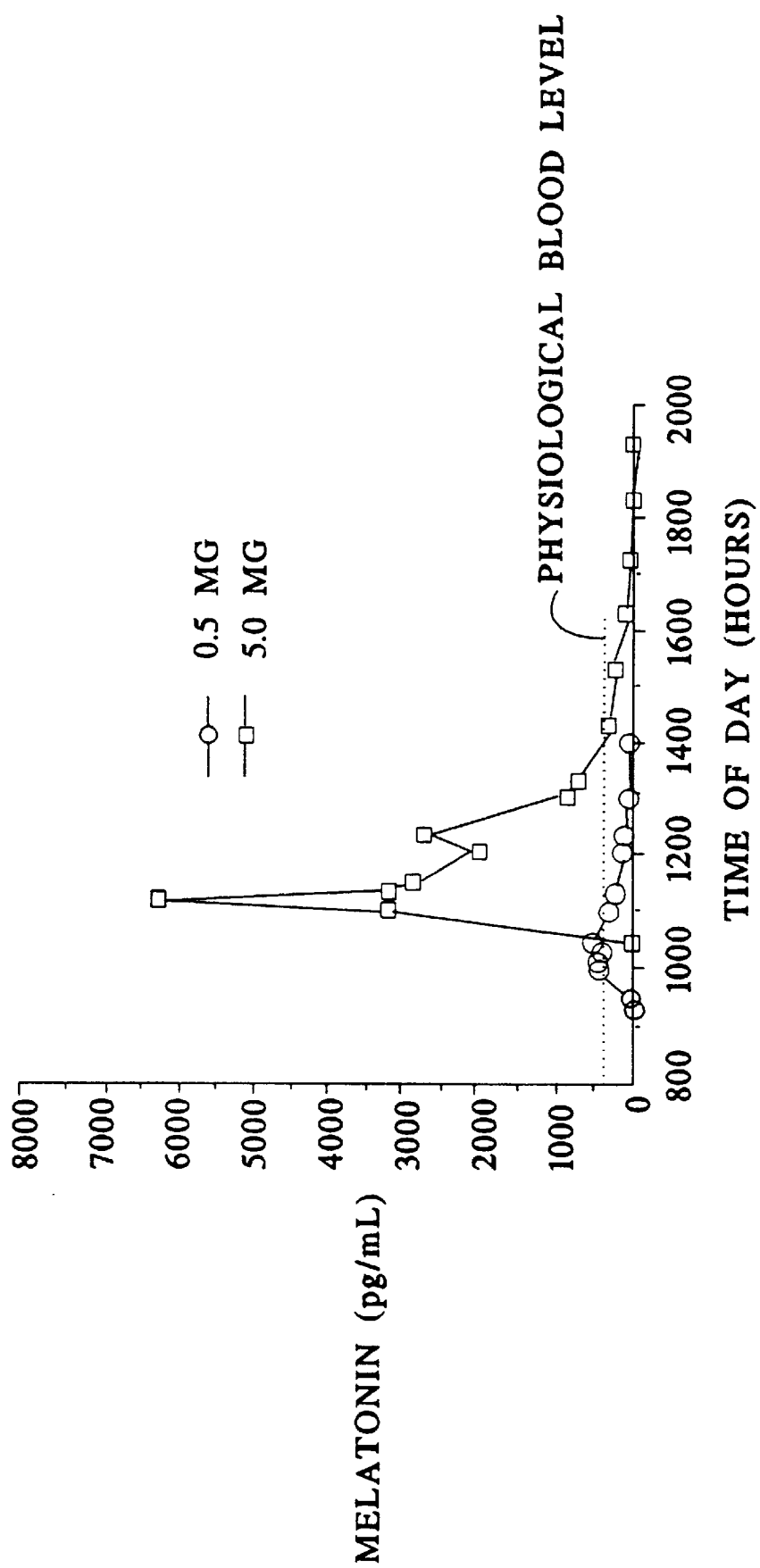
FIG. 8 illustrates the pharmacokinetic appearance of exogenous melatonin in blood after oral administration.

Melatonin was administered at two different dosages: 5 mg doses were used as prescribed by the prior art, and 0.5 mg doses were given using the administration protocol of instant invention. FIG. 8 shows the pharmacokinetic profile of melatonin in a subject's bloodstream obtained consequent to melatonin administration for both dosages. Melatonin levels in blood samples were analyzed using conventional techniques of radioimmunoassay (RIA). As shown in FIG. 8, administration of 0.5 mg of melatonin raised melatonin blood levels to approximately the maximum normal physiological blood level. In contrast, administration of 5 mg of melatonin raised melatonin levels to more than twelve (12) times the maximum normal physiological blood level.

FIG. 9A and 9B shows the results of DLMO phase-shifting achieved using the two melatonin administration protocols with 2 representative individuals during melatonin-induced phase delay in Hawaii. In travelling to Hawaii, the subject travels 3 time zones west, so that the endogenous circadian rhythm is ahead of the environmental light-dark cycle at the Hawaiian destination. This means that the subject became tired and sleepy approximately 3 hours before it was locally appropriate for going to sleep. In order to effectively alleviate the circadian rhythm disruption of jet lag, the subject's DLMO time had to be delayed by 3 hours in order for the subject to stay alert in the evening and to become sleepy at the locally appropriate time. The desired effect of melatonin administration was thus to effectuate a phase delay in DLMO.

While in Hawaii, subjects were kept in dim light after 4 PM for DLMO determinations, to avoid the confounding effects of late afternoon sunlight or other bright light that would suppress the DLMO and artifactually delay it. As a consequence, re-alignment of the circadian rhythm of DLMO with the local light/dark cycle was not completely achieved during the trip to Hawaii. It appeared that complete readjustment was not possible in the absence of the late afternoon sun zeitgeber. Thus, the critical day in Hawaii for comparing the effects of the 2 protocols on the melatonin circadian rhythm was determined to be the third (last) post-travel day of melatonin administration.

Melatonin is administered in the morning according to the schedule predicted by the melatonin PRC (Table I) to effect a phase delay. As can be seen in FIG. 9A, melatonin administration using this protocol resulted in a DLMO time that was correctly phase-shifted 1 hour later. These results are in contrast to the DLMO time produced using the method that teaches taking melatonin at destination bedtime. These results indicated that the instant invention is more efficacious in effectuating the appropriate phase delay than is melatonin administration at destination bedtime.

FIG. 9B, also shows the results of the phase-shifting experiment with these subjects in Portland after the return trip. In travelling to Portland, the subjects travelled 3 time zones east, so that the endogenous circadian rhythm was behind the environmental light-dark cycle at the Portland destination. This meant that the subjects did not become sleepy until 3 hours after the locally-appropriate time and had difficulty awakening at the locally appropriate time. Thus, to be efficacious the melatonin administration protocol had to accomplish a phase advance of the DLMO time.

In contrast to the subject's experiences in Hawaii, for the return trip to Portland, access to morning sunlight was found to help all of the subjects to re-adjust by the last day of melatonin administration. The appropriate day in Portland, therefore, for comparing the effects of the present invention was the day after the second post-travel day of melatonin administration. Melatonin was administered in the afternoon according to the teachings of the instant invention as directed by the melatonin PRC, to cause a phase advance. FIG. 9B shows that the DLMO time was approximately 1 hour earlier using the instant invention than the DLMO time produced by the melatonin administration protocol at destination bedtime. These results indicated that the instant invention is more efficacious in effectuating the appropriate phase advance is melatonin administration at a different and fixed time of day (i.e., destination bedtime).

The cumulative results of the experimental data acquired in these experiments are shown in Table II. The Table presents a comparison between the experimental results obtained using melatonin administration times according to the instant invention and those prescribed by the prior art. When mean DLMO times were compared, there was about a 1 hour difference in the degree of melatonin circadian rhythm phase shift produced, with the instant invention proving to be more efficacious in producing both phase delays and phase advances, depending on the time of melatonin administration. These results were consistent with the predictions of the melatonin PRC (disclosed in U.S. patent Ser. No. 5,232,941, incorporated by reference). Specifically, for the trip to Hawaii the instant invention produced a later DLMO time more rapidly than the methods known in the prior art in 5 of the subjects; the results with the sixth subject were also better, albeit marginally. For the trip back to Portland, the instant invention worked significantly better in 5 of the subjects (defined as achieving an earlier DLMO time than the prior art method), while the prior art method worked marginally better for I subject.

Statistical analyses were performed and these results are shown in Table III. In 10 of 12 comparisons for the entire data set, the methods of the instant invention produced better results (defined as a greater degree of phase advance or phase delay) as assessed by $\chi^2$ analysis (statistical significance=$p<0.025$). Specifically, on the trip to Hawaii, the instant invention shifted the DLMO time to a time later than the prior art methods by almost 1 hour on average. This was statistically significant at the $p<0.02$ level (using a 2 tailed paired t test). On the trip back to Portland, the instant invention advanced the DLMO time to a time earlier than melatonin administration at destination bedtime by almost 1 hour on average; these results were statistically significant at the $p<0.05$ level in a 1-tailed paired t test.

During the study, one of the subjects (#6) had a hematocrit (a measure of the number of red blood cells) that precluded taking blood samples for determining plasma melatonin levels for her second trip to and from Hawaii; saliva samples were taken instead and analyzed as an alterative using gas chromatography-mass spectrometry (GC-MS). To avoid inappropriate comparisons between these data and the remaining samples in the data set, statistical analyses were also performed after deleting the data corresponding to this subject from the data set.

When the DLMO data for the trip to Hawaii obtained from subject #6 were removed from the data set, the differences between degree of melatonin-induced circadian rhythm phase shift achieved using the administration methods of the instant invention versus administration at detination bedtime remained significant at the $p<0.01$ level on a 2-tailed paired t test. When the DLMO data for the return trip to Portland obtained from subject #6 were removed from the data set, the differences between the instant method and the prior art methods were found to be no longer statistically significant. However, even when the data from subject #6 were deleted from the data set as a whole, nine of the ten comparisons of the 2 melatonin administration protocols favored the method of the instant invention by $\chi^2$ analysis, achieving a statistical significance of $p<0.025$.

Subjective impressions of the study participants were also elicited, and these subjective assessments were, by and large, consistent with the more objective (and more reliable) physiological data. These experiments demonstrate the efficacy of the methods of the instant invention in relieving the circadian rhythm phase-shifting effects of transmeridional flight (i.e., jet lag). The instant method is capable of achieving an appropriate adjustment of the DLMO circadian rhythm and in alleviating the physiological symptoms of jet lag.

The results demonstrate that physiological doses of melatonin given at times according to the melatonin PRC of endogenous melatonin production, and adjusting the administration times on a daily basis in accordance to the predicted shifts of the melatonin PRC, is more efficacious than melatonin administration schemes based on fixed administration times (destination sedation) of high dosages of exogenous melatonin.

EXAMPLE 6

Melatonin Administration to Treat Winter Depression

A series of experiments were performed to illustrate the usefulness of the instant invention for alleviating winter depression (seasonal affective disorder) in 10 subjects.

Exogenous melatonin was administered to subjects orally in capsule form at a specific time in relation to the individual's dim light melatonin onset (DLMO) time. This treatment was continued for one week. The following week, the time of administration of the melatonin dose was advanced one hour, in order to take into account the shift in the DLMO time predicted by the human phase response curve (PRC) due to the prior week's treatment. The time of administration for this study was centered at CT 8. The subjects were given two capsules a day, a placebo capsule in the morning and a melatonin-containing capsule in the afternoon, at the appropriate test time (i.e., CT 8 (3 PM) on week 1 and CT 8 (2 PM) on week 2).

This study was performed in a double-blind fashion. Physiological melatonin levels were determined in each subject at the beginning of the study and at the end of the two-week period. Blood samples were taken every thirty minutes in the evening while the subjects were in dim light in order to determine each individual's DLMO. Physiological melatonin blood levels were determined using GC-MS, as described above in Example 1.

Subjects were medically and psychologically screened for participation in the study, and the subjects studied were uniformly in generally good physical condition, met the DSM-III-R criteria for moderate to severe major depressive disorder (without psychotic episodes) or bipolar disorder (depressed or not otherwise specified (NOS)) with winter type seasonal pattern, scored ≧20 on the Structured Interview Guide for the Hamilton-Seasonal Affective Disorder (SIGH-SAD) with Hamilton Depression Rating Scale (HDRS) ≧10 and an atypical score ≧5, and reported that depression had developed during the fall or winter and had remitted the following spring for at least the two preceding winters. Further, the subjects were not suicidal and had not used or been treated with psychoactive drugs during the month preceding the study. the SIGH-SAD is a 29-item interview-based instrument that was used to assess depressive symptom severity. Twenty-one of the items are identical with items in the HDRS (which is a widely-used psychiatric instrument). In addition, the SIGH-SAD contains eight items which specifically assess symptoms characteristic of winter depression, such as carbohydrate craving, weight gain and hypersomnia. Scores greater than or equal to 20 indicated moderate to severe depression.

Figure 10:
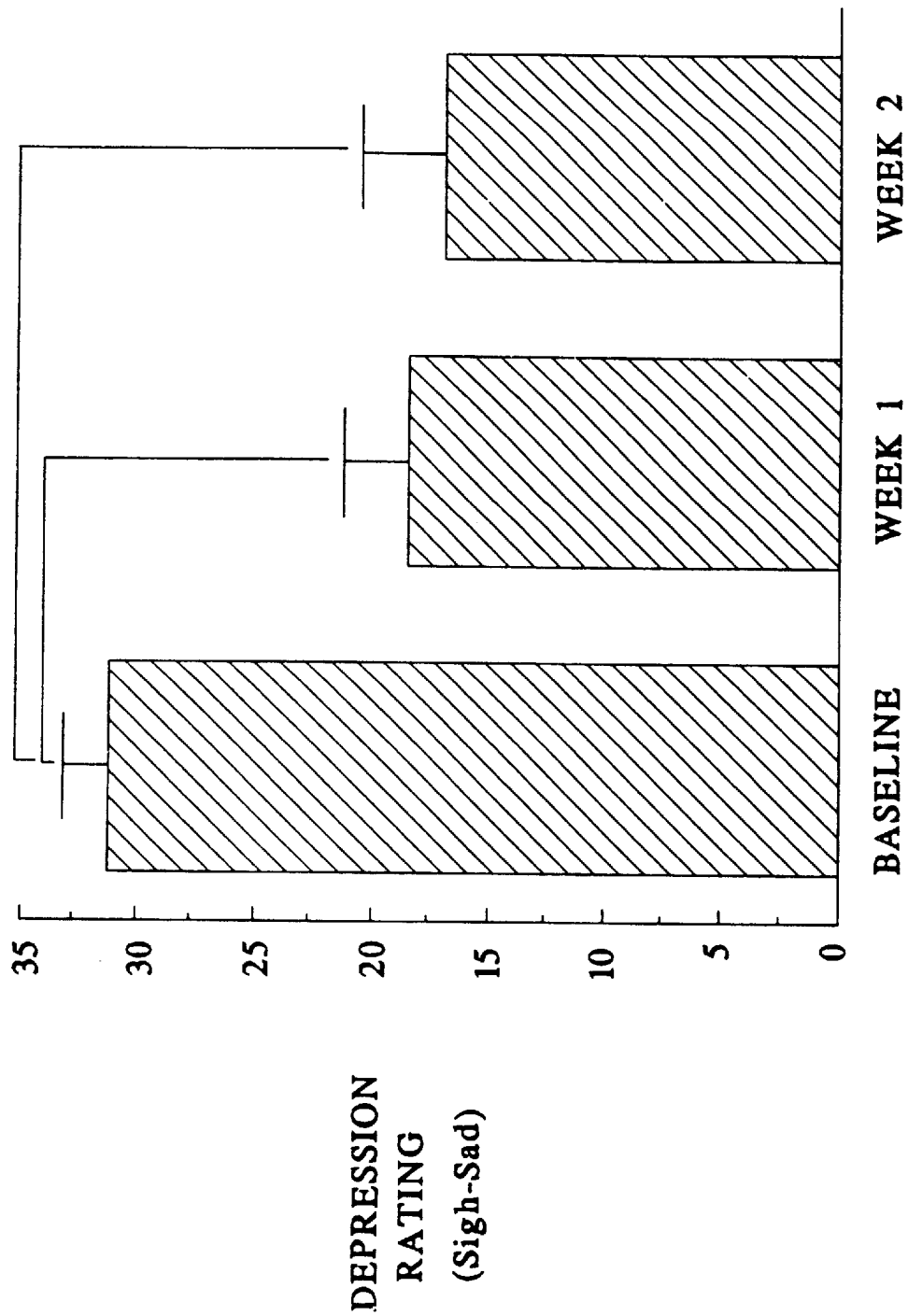
FIG. 10 shows the relationship between the degree of improvement in SIGH-SAD ratings in patients with winter depression and melatonin treatment as described in Example 6.

The first group of 4 subjects received 0.5 mg of melatonin in the afternoon capsule. All patients on melatonin improved when it was administered at a time to cause a phase-advance as predicted by the PRC. Three out of four individuals given 0.5 mg of melatonin recorded a significant phase shift. Three out of four of these individuals also showed a significant improvement in the SIGH-SAD rating after two weeks. These results are shown in FIG. 10. Statistically-significant decreases in the average depression ratings (SIGH-SAD) were seen for patients undergoing melatonin treatment as herein described. However, there were also complaints of early morning awakening and/or afternoon sleepiness following this treatment, which are disfavored because they could be mistaken by these already-depressed patient as signs of lingering winter depression. These data indicated that an individual's positive response to the phase-shifting effect of exogenous melatonin administration, i.e., improvement in SIGH-SAD rating, may be dependent on the direction of the specific shift, and that the magnitude of the phase shift may be important in influencing the therapeutic effectiveness of exogenous melatonin treatment.

Since the 0.5 mg dose was found to induce soporific side effects that a patient could confuse with lingering depression (thereby potentially exacerbating the depression), the study was repeated using a 0.25 mg dose of melatonin administered to four subjects essentially as described above. This dosage was less likely to result in an excessive degree of "phase-advance" which could also have created the soporific side effects observed using higher doses of melatonin. In these four subjects treated with 0.25 mg of melatonin in the afternoon, the anti-depressive response was remarkably better than the results obtained using 0.5 mg administrations, and there were fewer complaints of early morning awakening or afternoon sleepiness in these subjects. All of these individuals showed a shift in the PRC. On average, the magnitude of the phase advance was less than the phase advance found in individuals treated with 0.5 mg; these results were predicted by the PRC as shown in Example 3. The smaller degree of phase advance, and reduced soporific side-effects, found using 0.25 mg melatonin administration doses also resulted in significant improvements in the depression rating measured by the SIGH-SAD in these four individuals. One noteworthy result from this series of experiments was that the individual with the smallest amount of improvement in depression ratings was also the individual with the greatest phase shift.

Figure 11:
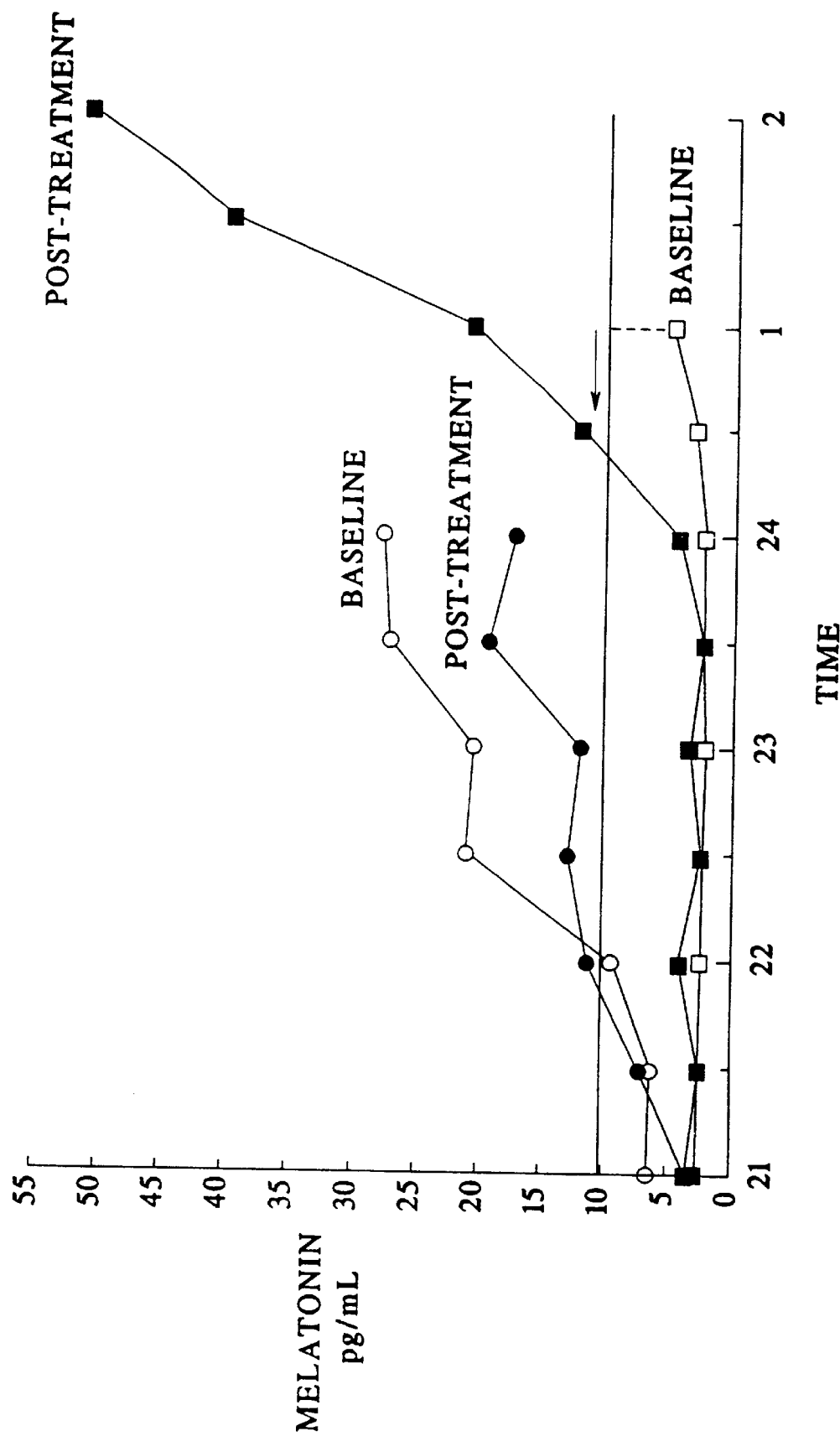
FIG. 11 depicts baseline and post-treatment DLMO times for two winter depressive patients treated with melatonin and atenolol.

Two other subjects were given 0.125 mg of melatonin in combination with 100 mg atenolol, a beta-adrenergic blocker that inhibits endogenous melatonin production without blocking the effect of exogenous melatonin binding. These subjects' winter depression ratings responded similarly to those subjects treated with the 0.25 mg dose protocol. These subjects also showed a slight phase advance similar in magnitude to the phase advance produced in those subjects treated with 0.25 mg melatonin alone. The results of this study are shown in FIG. 11, which shows the phase advance of one of the subjects' DLMO time after treatment as described (Subject MD (closed square), DLMO phase shift shown by the arrow) herein. These results were most readily explained as resulting from the combined reduction of endogenous melatonin production at the wrong time (i.e., the delay zone of the melatonin PRC), and the exogenous administration of melatonin at the correct time, thereby creating a phase shift almost equal in magnitude to the phase shift produced by administration of the higher dose. These data also indicated that smaller phase shifts resulted in greater improvement in the SIGH-SAD depression ratings. These results are tabulated in Table IV, which presents both the SIGH-SAD and DLMO data for the individual subjects.

Figure 12:
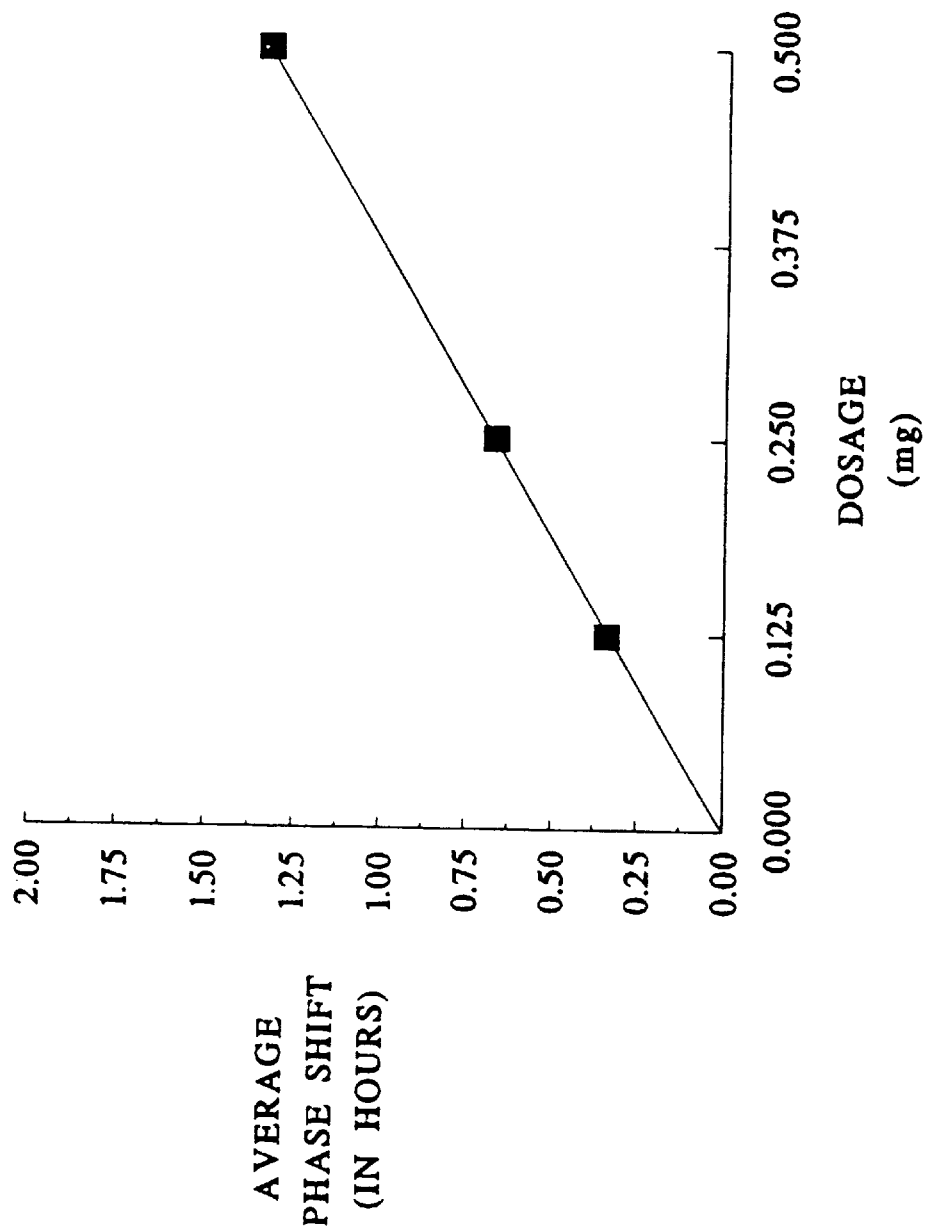
FIG. 12 illustrates the linear relationship between dose of melatonin and the amount of phase shift achieved in experiments using 0.125 mg melatonin+100 mg atenolol treatment and melatonin at dosages of 0.25 and 0.5 mg without atenolol.
Figure 13:
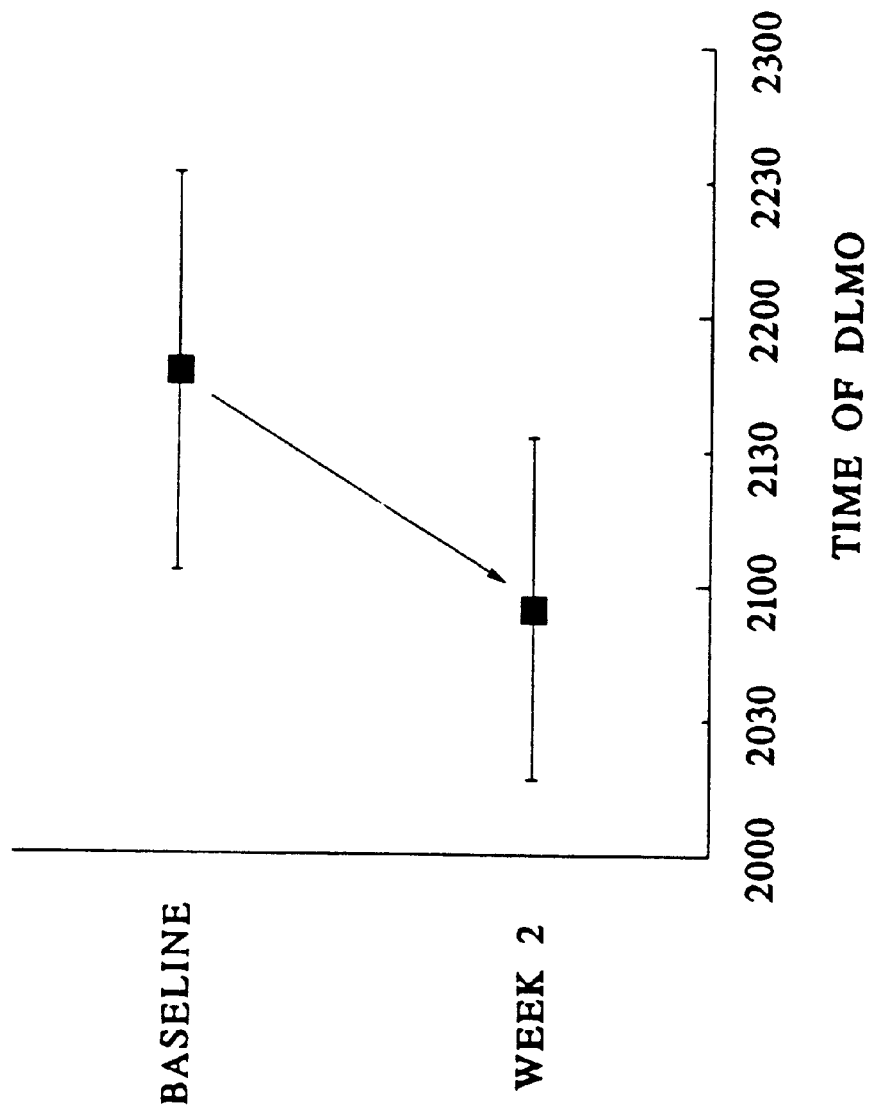
FIG. 13 shows the average phase shift in DLMO after 2 weeks of melatonin administration as described in Example 6.
Figure 14:
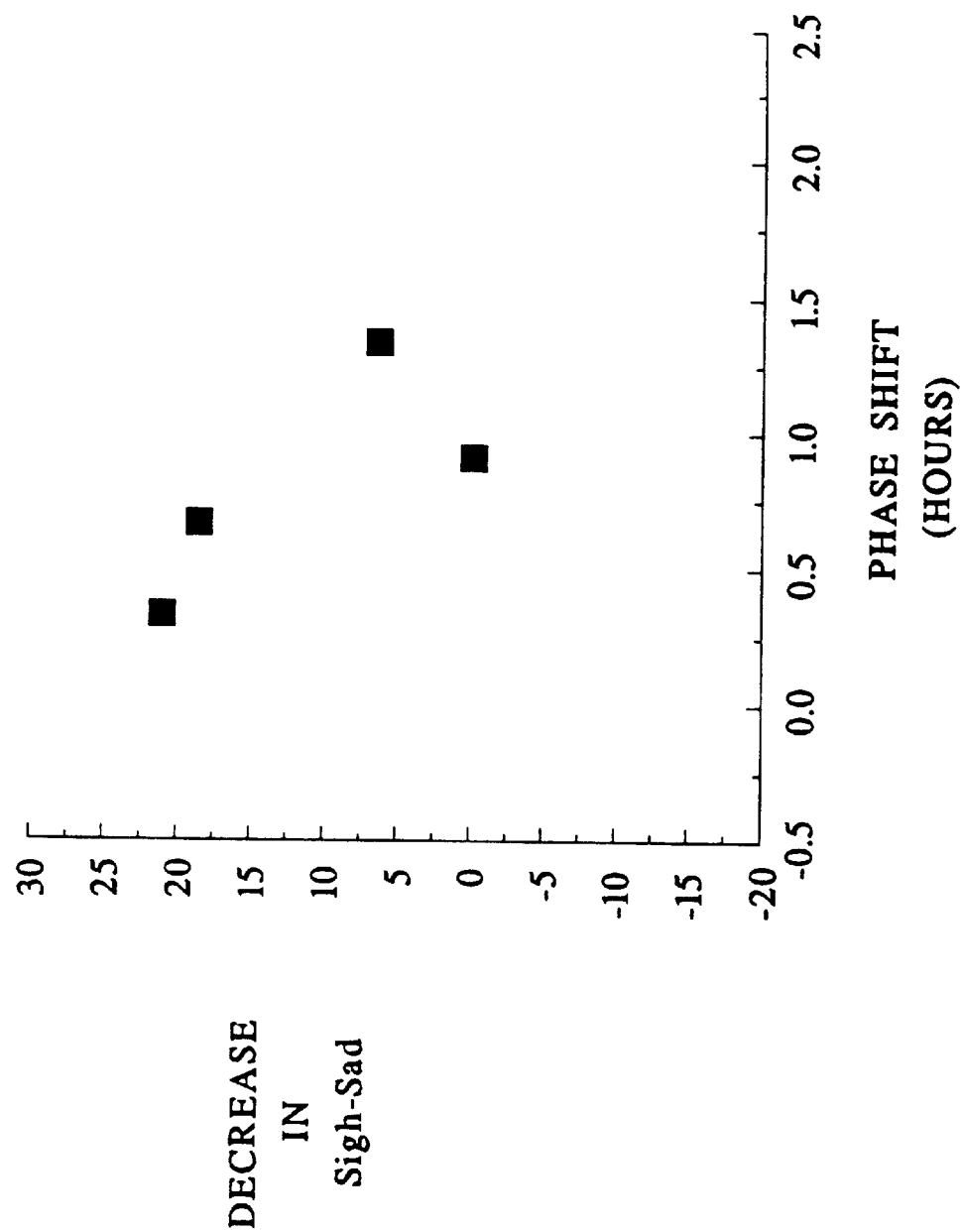
FIG. 14 relates the degree of phase shift caused by melatonin administration to changes in winter depression as measured by the SIGH-SAD criteria; wherein the amount of melatonin administered associated with each data point is as follows (from left to right): WD'93, 0.125 mg (n=2); WD'93, 0.25 mg (N=4); WD'90, 0.5 mg (n=7) and WD'93, 0.5 mg (n=4)
Figure 15:
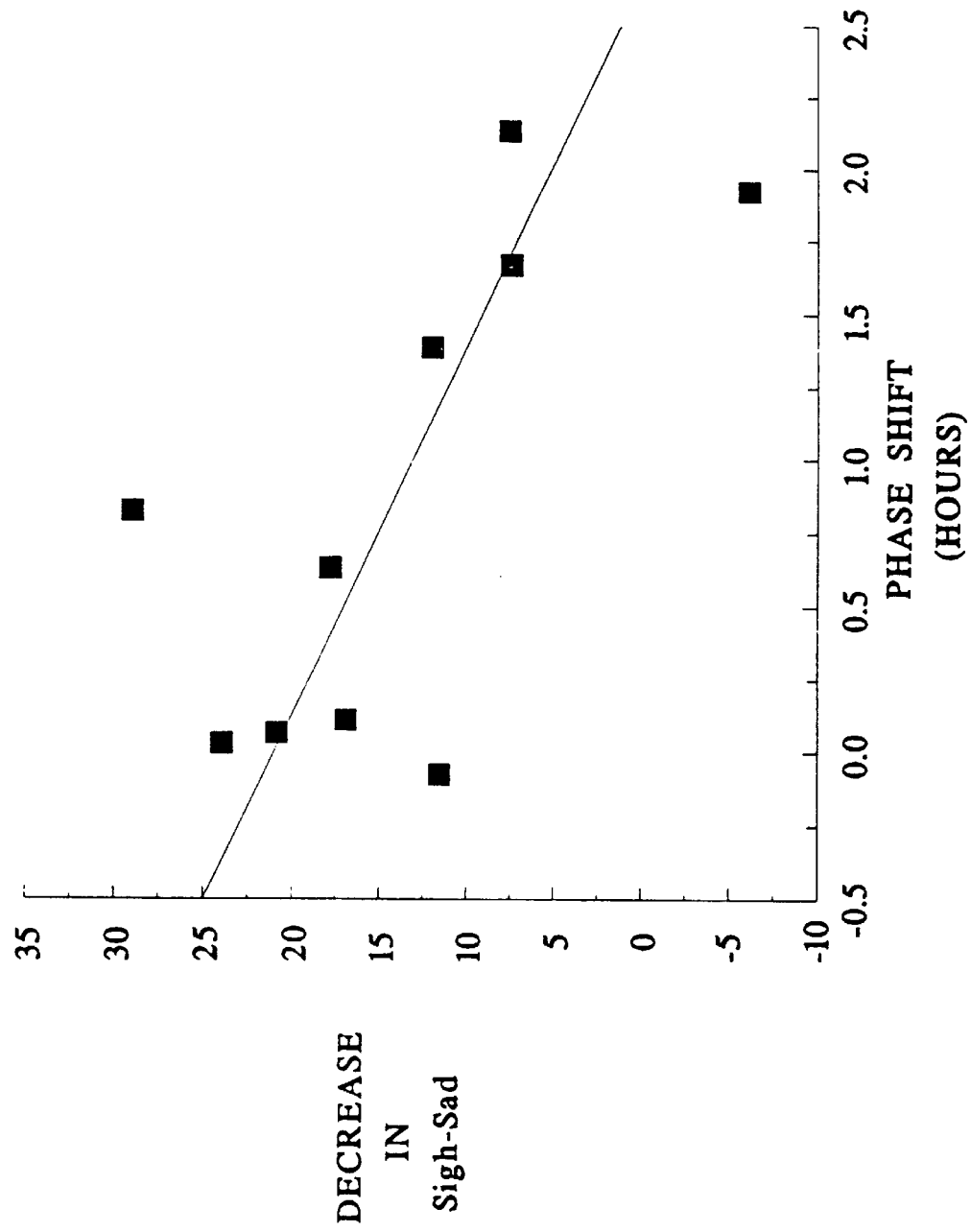
FIG. 15 illustrates the inverse relationship between the magnitude of the induced melatonin phase shift and improvement in the SIGH-SAD ratings in winter depressive patients.

These results are summarized in FIGS. 12–15. FIG. 12 illustrates the linear relationship between the administered dose of melatonin and the magnitude of the phase shift achieved in experiments using 0.125 mg melatonin+100 mg atenolol treatment and treatment with 0.25 and 0.5 mg dosages of melatonin alone. FIG. 13 shows that the average phase shift in DLMO after 2 weeks of melatonin administration is statistically significant. FIG. 14 relates the degree of phase shift achieved to changes in winter depression as measured by the SIGH-SAD criteria. Finally, the inverse relationship between the magnitude of the induced melatonin phase shift and improvement in the SIGH-SAD ratings is shown in FIG. 15. These results demonstrate that the optimal decrease in symptoms of winter depression in these patients (as measured by the SIGH-SAD ratings) occurred when the melatonin PRC was phase-shifted by a phase advance of about 0.5 h. Individuals who were shifted by nearly 1 h or more recorded much lower improvement in SIGH-SAD ratings.

The results indicate that to administration of melatonin at specific times relative to DLMO as predicted by the melatonin PRC caused the DLMO time to advance, and that the phase advance was related to alleviation of the symptoms of winter depression. The result of exogenous melatonin administration as described herein represents a controlled shift in the endogenous circadian pacemaker, resulting in amelioration of the symptoms of winter depression. Small shifts in the endogenous circadian pacemaker, as indicated by the shift of the DLMO time, were found to be effective in causing this amelioration of winter depressive symptoms. The optimal magnitude of phase advance was found to be a shift of about 0.5 hour in the DLMO time, which resulted in the greatest degree of improvement in patients' SIGH-SAD ratings. The instant results also showed that the time of melatonin administration resulting in greatest amount of improvement in winter depression symptoms was dependent on the baseline DLMO time of the individual, as well as idiosyncratic responses to the dosage of exogenously administered melatonin.

EXAMPLE 7

Melatonin Administration to Schedule-Related Circadian Phase Disturbances

Another application of the circadian rhythm phase-shifting methods provided by the present invention enables alleviation of circadian phase disturbances caused by changes in an individual's schedule or pattern of activity. One example of schedule-related circadian phase disturbances occurs in night-shift-workers. Workers who are assigned to the night shift face the problem of synchronizing their bodily rhythms (usually triggered by light/dark cycle cues) with their altered behavioral sleep pattern. Even though such workers can force a phase shift of 8–12 hours in their sleep pattern, their other circadian rhythms (which are coupled more tightly to the endogenous circadian pacemaker) may not shift. This state of internal desynchronization between sleep and other circadian rhythms may account for much of the difficulties encountered by night workers. The present example illustrates the use of melatonin treatment in conjunction with specific timing of melatonin administration in relation to the melatonin PRC for the resynchronization of internal circadian rhythms with the sleep cycle.

The subjects of this test were hospital shift workers (nurses and other paramedical personnel) who worked on a "7-70" rotating shift, consisting of seven consecutive 10-hour night shifts (9 PM–7 AM), alternating with seven days off-duty. Thus, these subjects made a 10–12 hour shift in their sleep cycle every week. During the study, blood samples were drawn weekly using a protocol of hourly blood draws under dim light (<50 lux) conditions for 24 hours. These blood samples were immediately centrifuged and frozen for later analysis of melatonin concentration.

Melatonin was measured using an RIA developed by Schumacher et al. (as described in Zimmerman et al., 1990, Fertil. Steril. 54: 612–618). The sensitivity of this assay is approximately 2.5 pg/ml; the coefficient of variability is 10.2% for concentrations of 15 pg/ml. A gas chromatographic mass spectrometric (GC-MS) assay was used to calibrate the RIA, and to validate critical samples. (The GC-MS assay has a lower limit of detection of approximately 0.5 pg/mi and a coefficient of variability of 2.7% for concentrations of 20 pg/mi.)

Figure 16A:
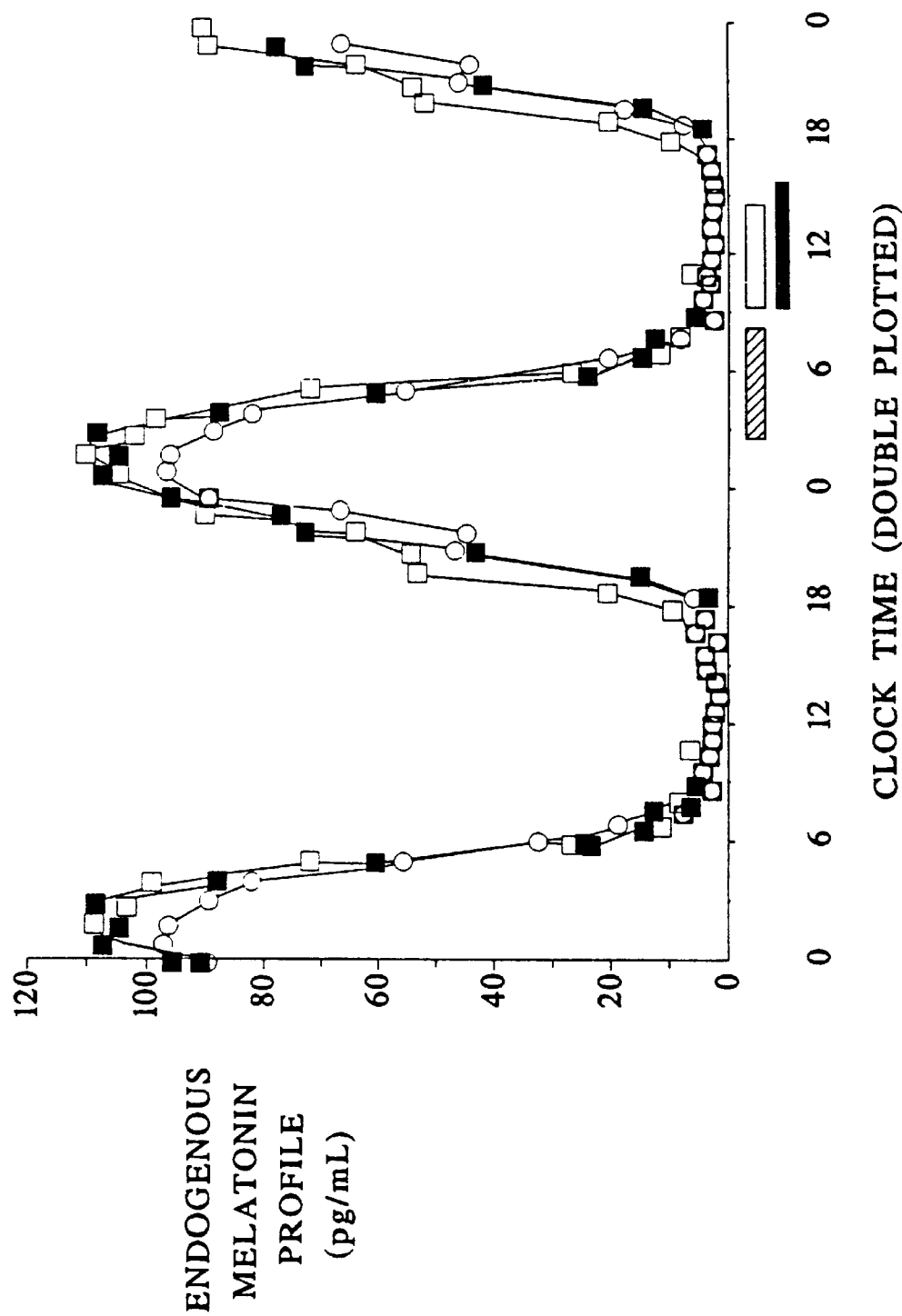
Figure 16C:
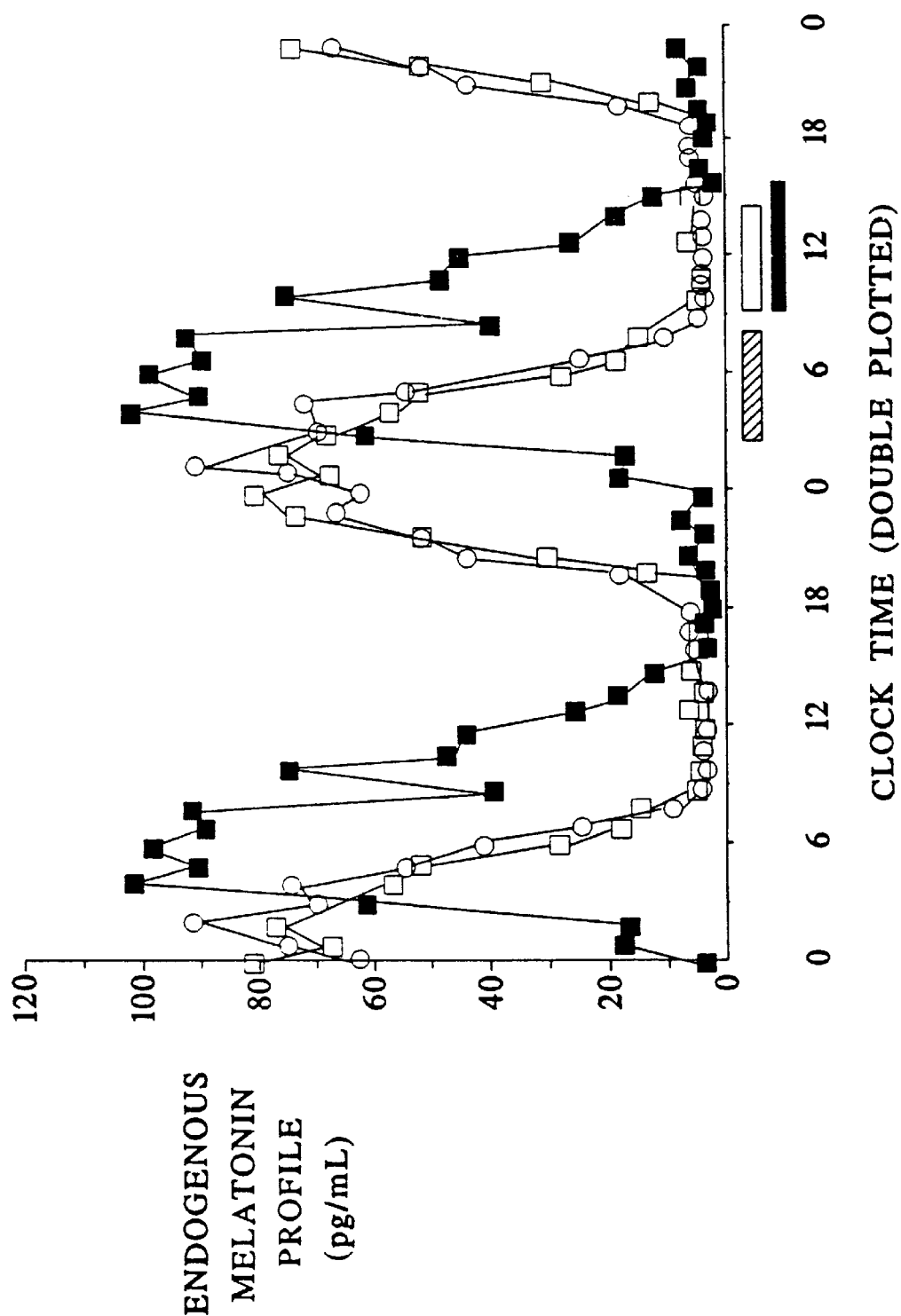
Figure 16D:
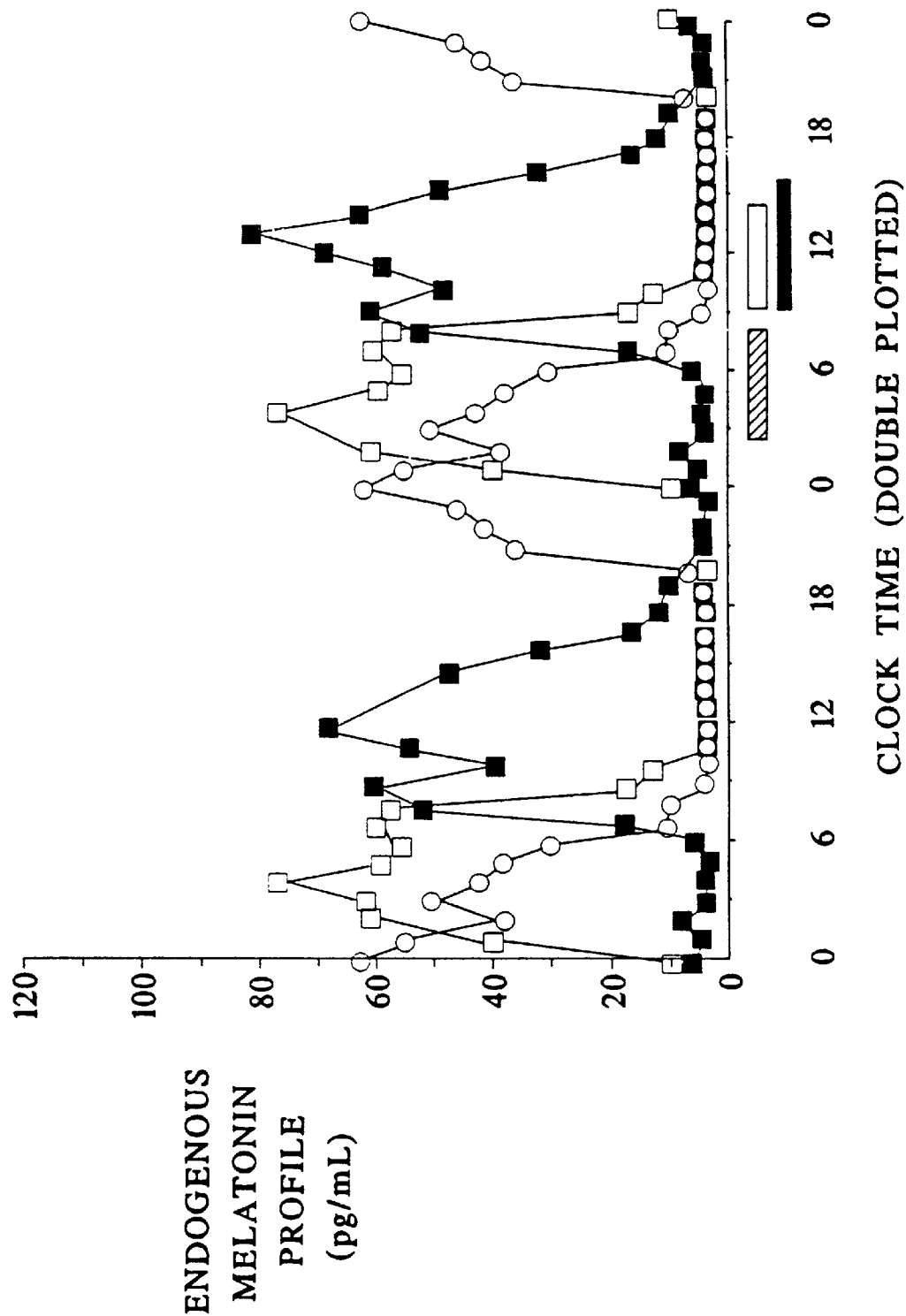
Figure 16E:
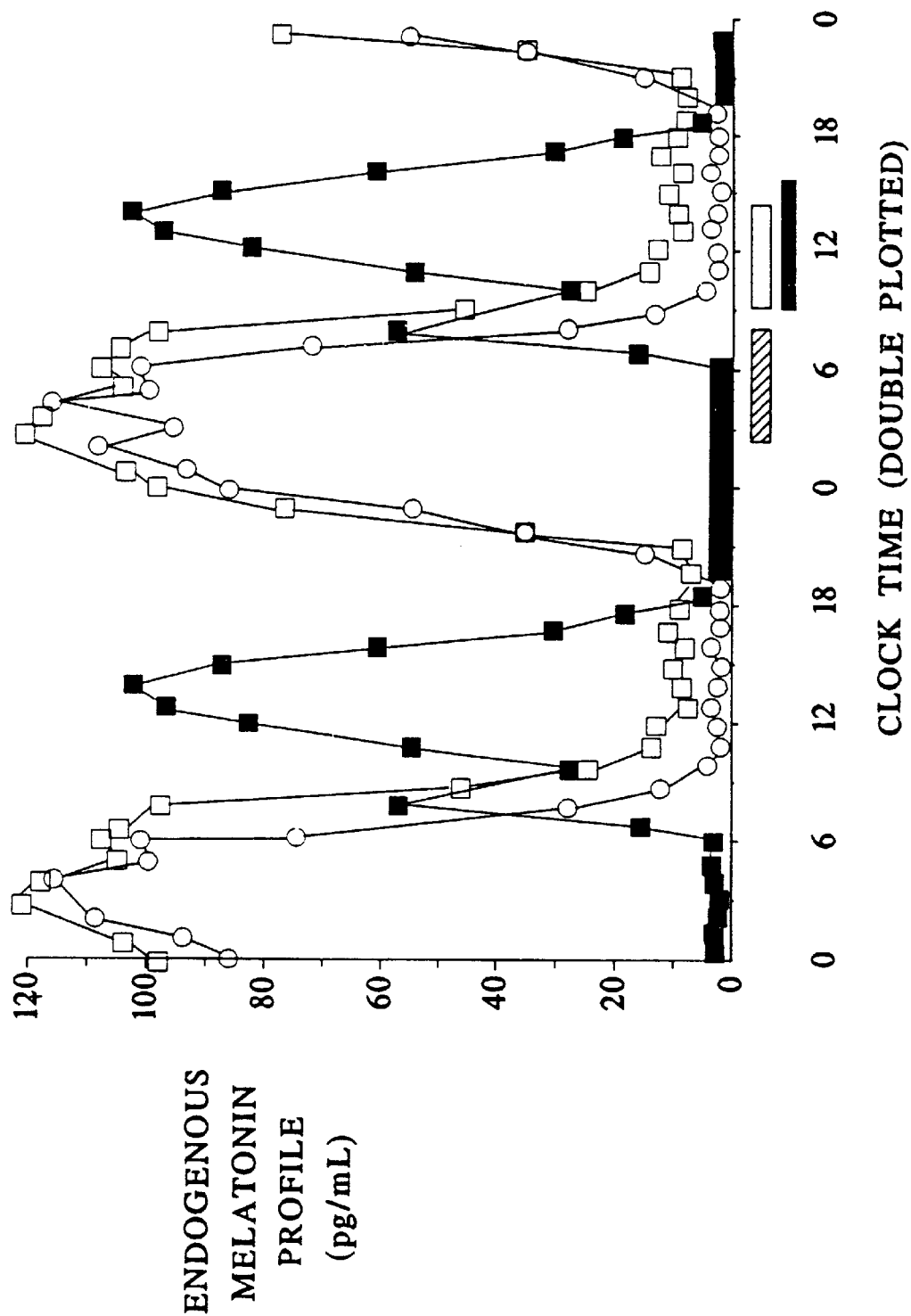
Figure 16F:
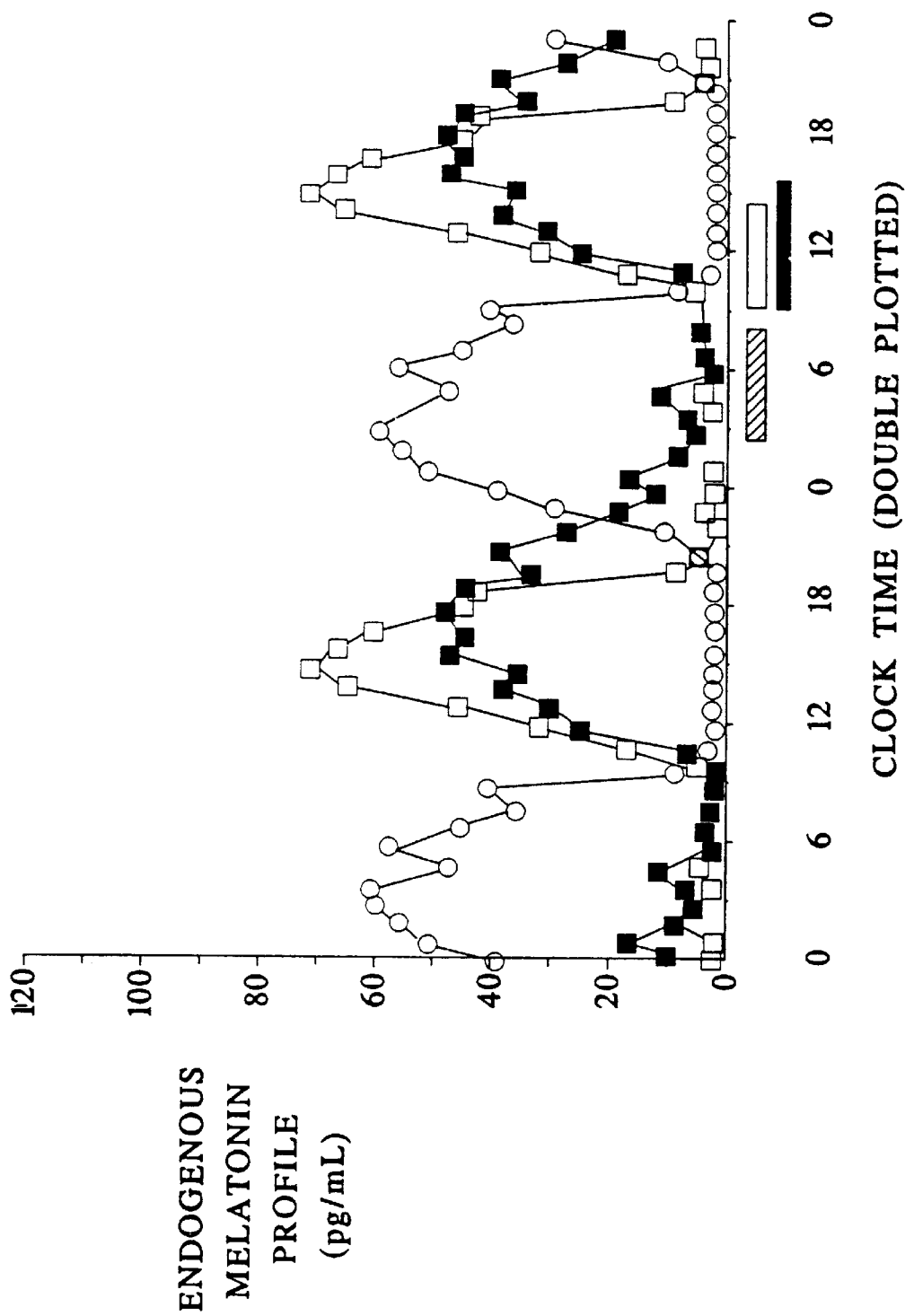

For plasma samples, circadian phase position was calculated by interpolating from the time that melatonin concentrations rose above a 10 pg/ml threshold (the DLMO time). To test the potential benefits of melatonin administration on phase resetting, for convenience subjects were given melatonin (0.5 mg) at bedtime for one two-week block, and placebo for the other two-week block, formulated in identical-looling cornstarch-filled gelatin capsules. Subjects did not know the identity of the treatment received (i.e., whether they were taking melatonin or placebo), and the order of treatment was randomized. To assess the ability of melatonin and placebo treatments to promote adaptation to a nocturnal schedule, the phase of the DLMO time was compared after each treatment with each subject's normal diurnal phase (see FIGS. 16A through 16 and 17). The results for subjects using placebo or no treatment showed that four of the six subjects had no substantial change in their DLMO times after a week of night work and daytime sleep (average shift for these four subjects was 0:34±1:09 hours). However, one subject shifted 12:30 hours and another subject shifted 3:54 hours, indicating considerable inter-individual variability in adaptation responses to melatonin administration. These data support the conclusion that even after seven night shifts, underlying circadian rhythms do not readily re-entrain to synchronize with the sleep-activity schedule.

Figure 17:
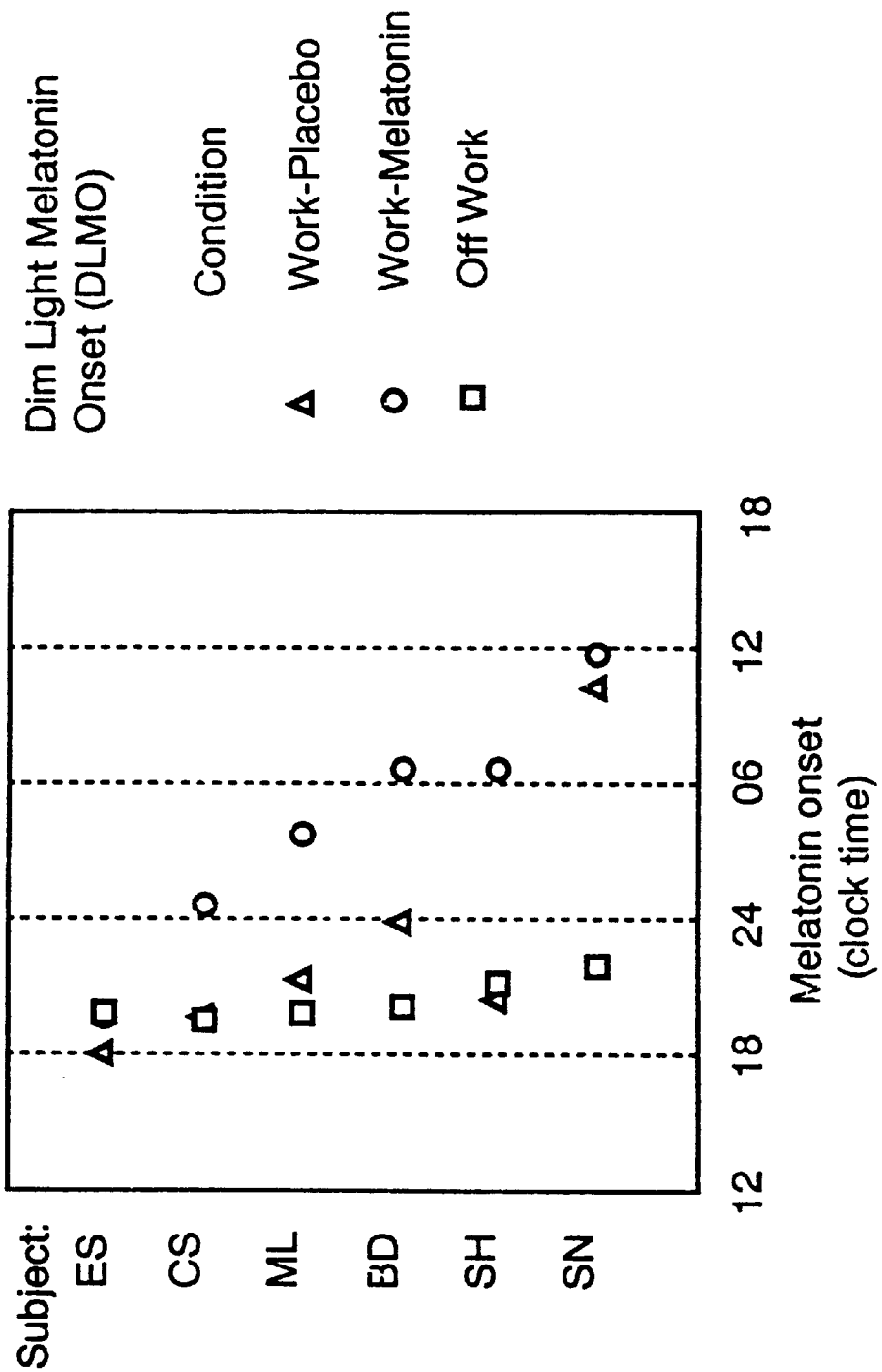
FIG. 17 provides a graphic summary of the data depicted in FIG. 15.

In contrast to the placebo results, melatonin treatment given during the week of nighttime work caused large phase shifts of the melatonin profile and improved adaptation to the nocturnal schedule (see FIGS. 16 and 17). All six subjects phase shifted with melatonin, the magnitude of the phase shifts ranging from 1:27 to 9:37 hours. The average phase difference between off work weeks and work weeks was 7:35±4:52 hours after melatonin treatment and 2:21±5:21 hours after placebo treatment ($p \leq 0.02$, paired t-test). Because one subject responded to neither treatment, and another subject completely adapted on both treatments, the subgroup of four remaining subjects was analyzed separately. The average phase difference between off work and work weeks was 7:58±2:37 hours after melatonin treatment, compared to 0:47±2:16 hour after placebo treatment ($p \leq 0.01$, paired t test).

Figure 18:
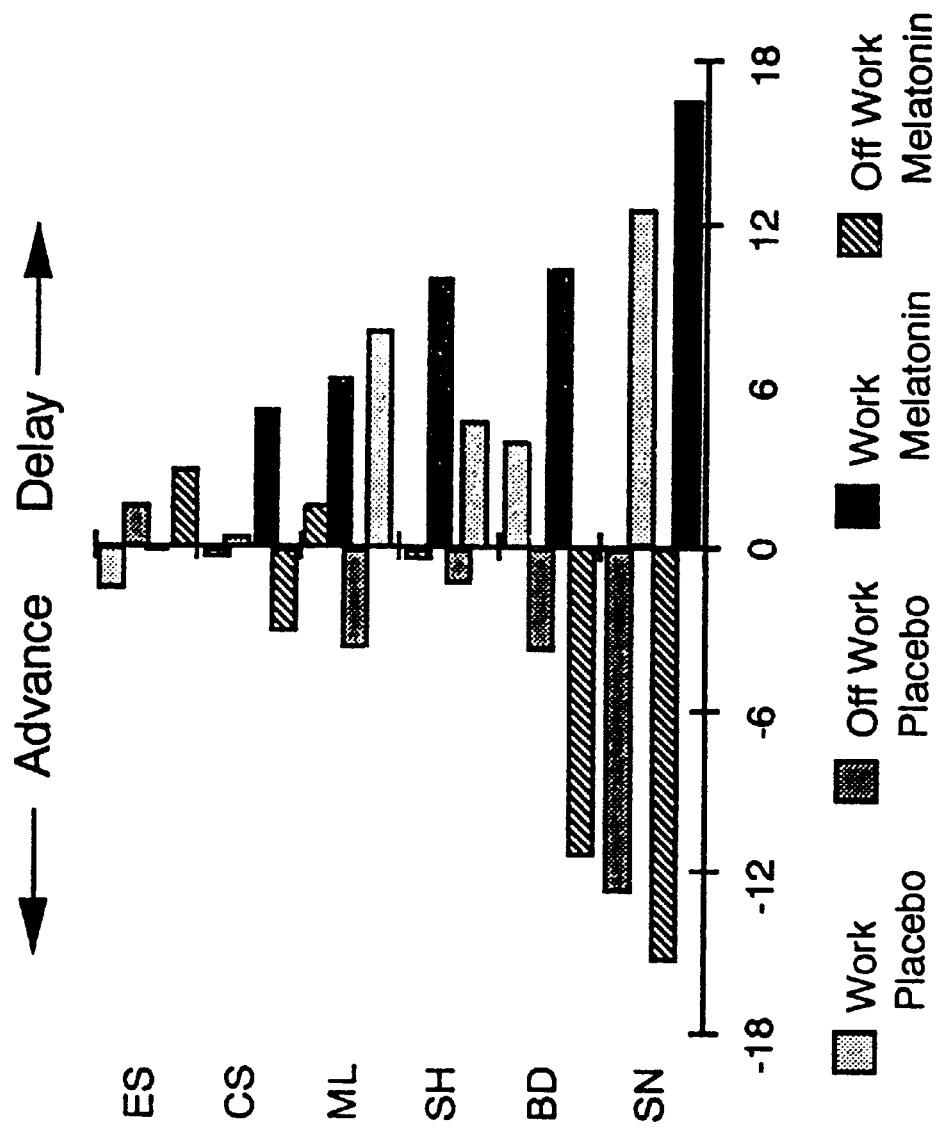
FIG. 18 shows phase shifts for six shift workers treated as described in Example 7.
Figure 19A:
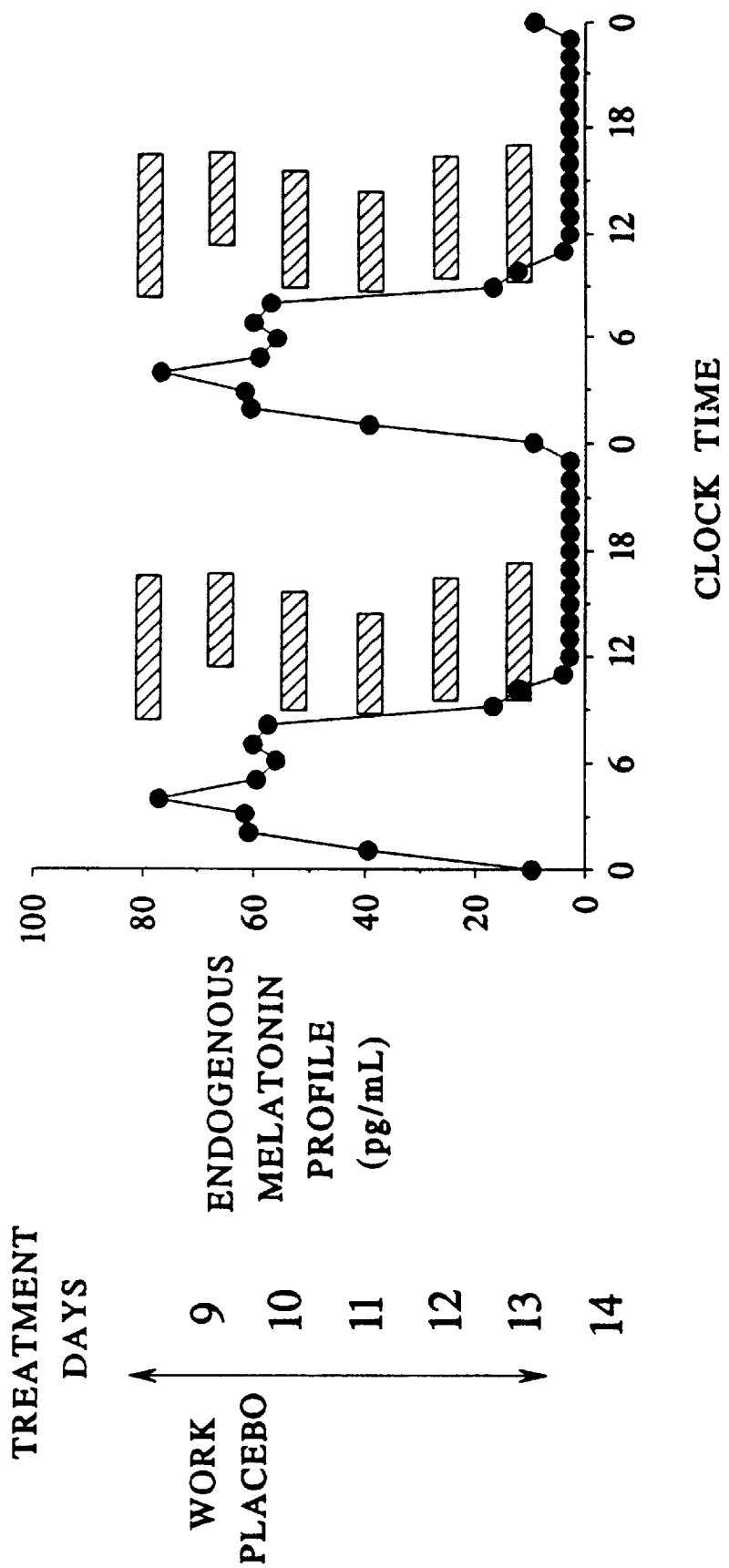
Figure 19B:
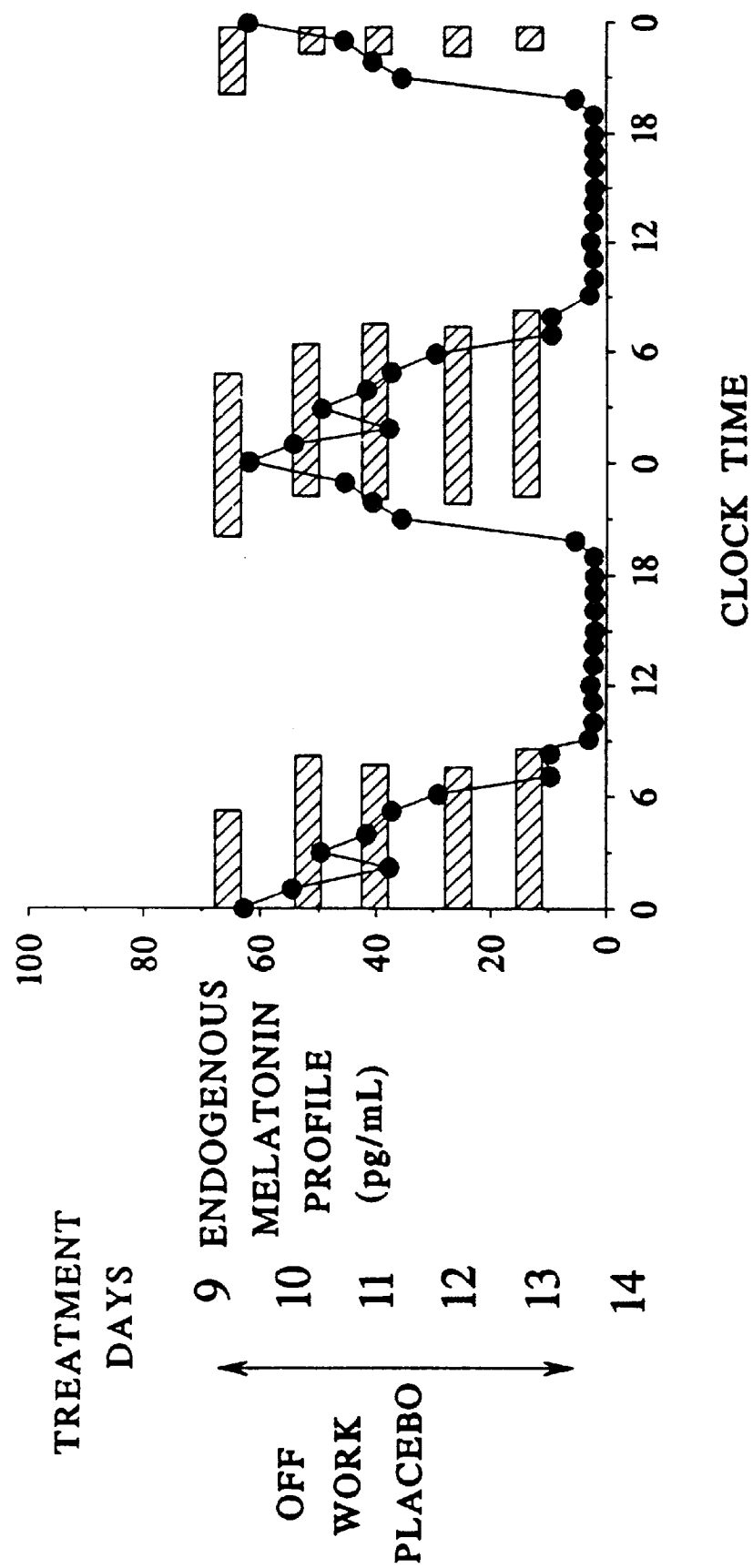
Figure 19D:
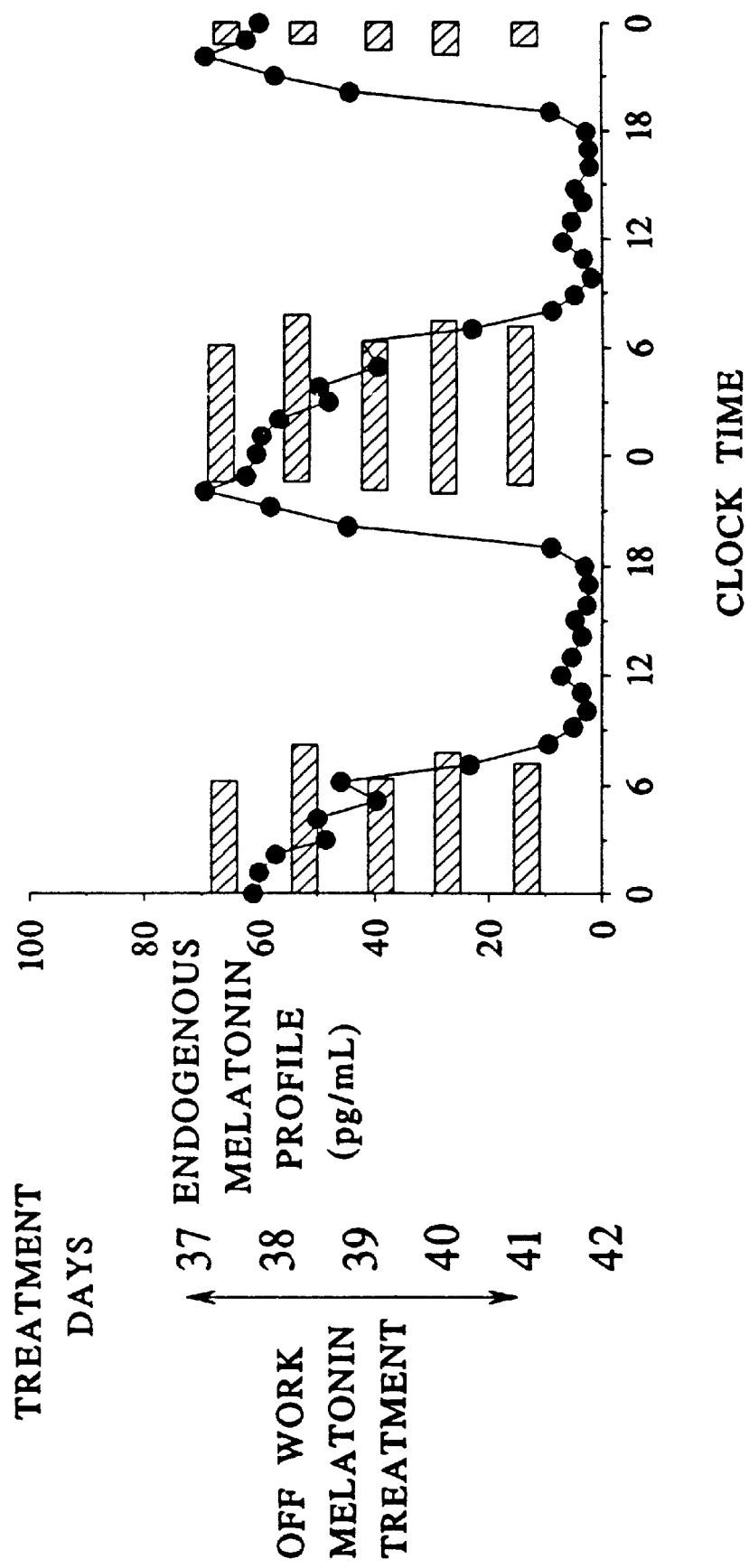
Figure 20A:
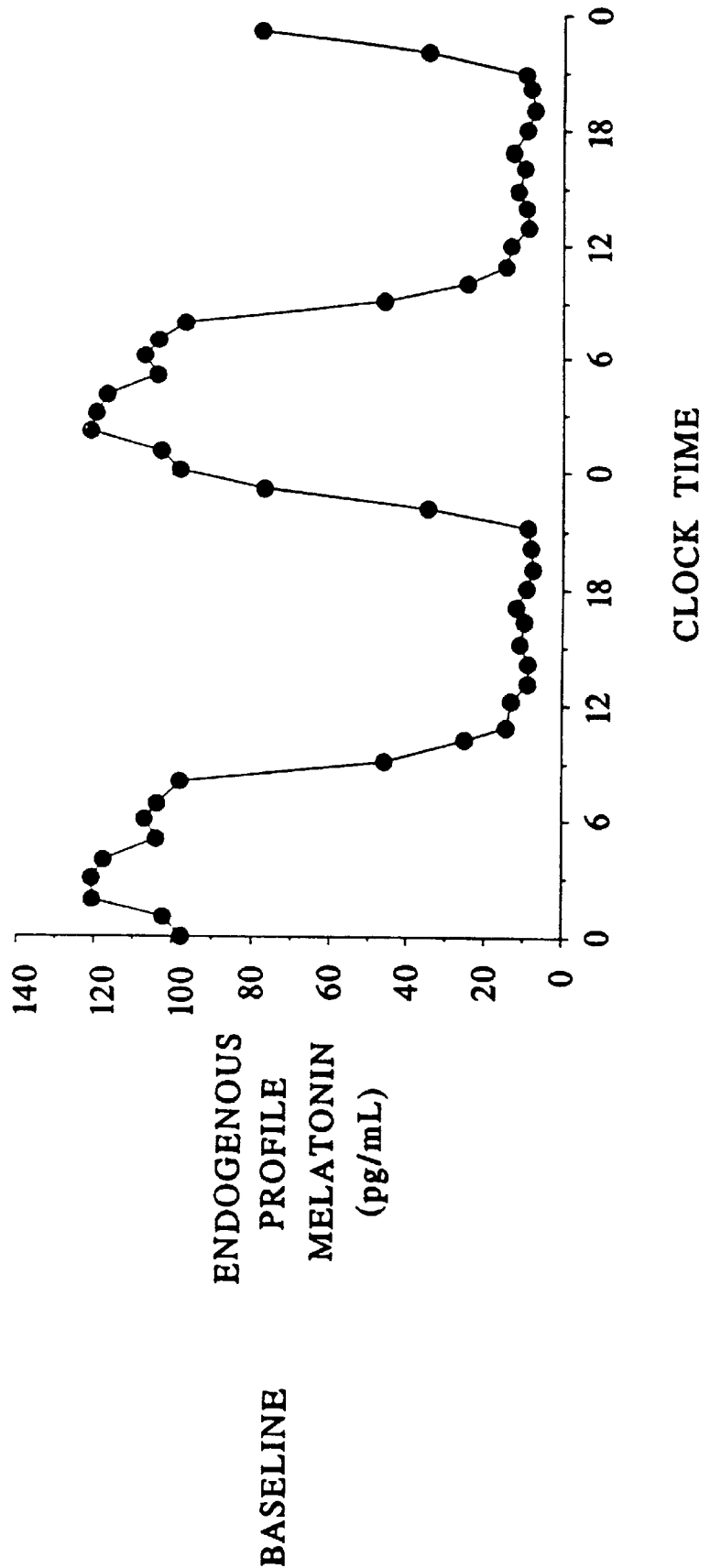
FIG. 20 shows plasma melatonin and sleep times for shift-worker SH; wherein crosshatched bars indicate sleep time and duration
Figure 20B:
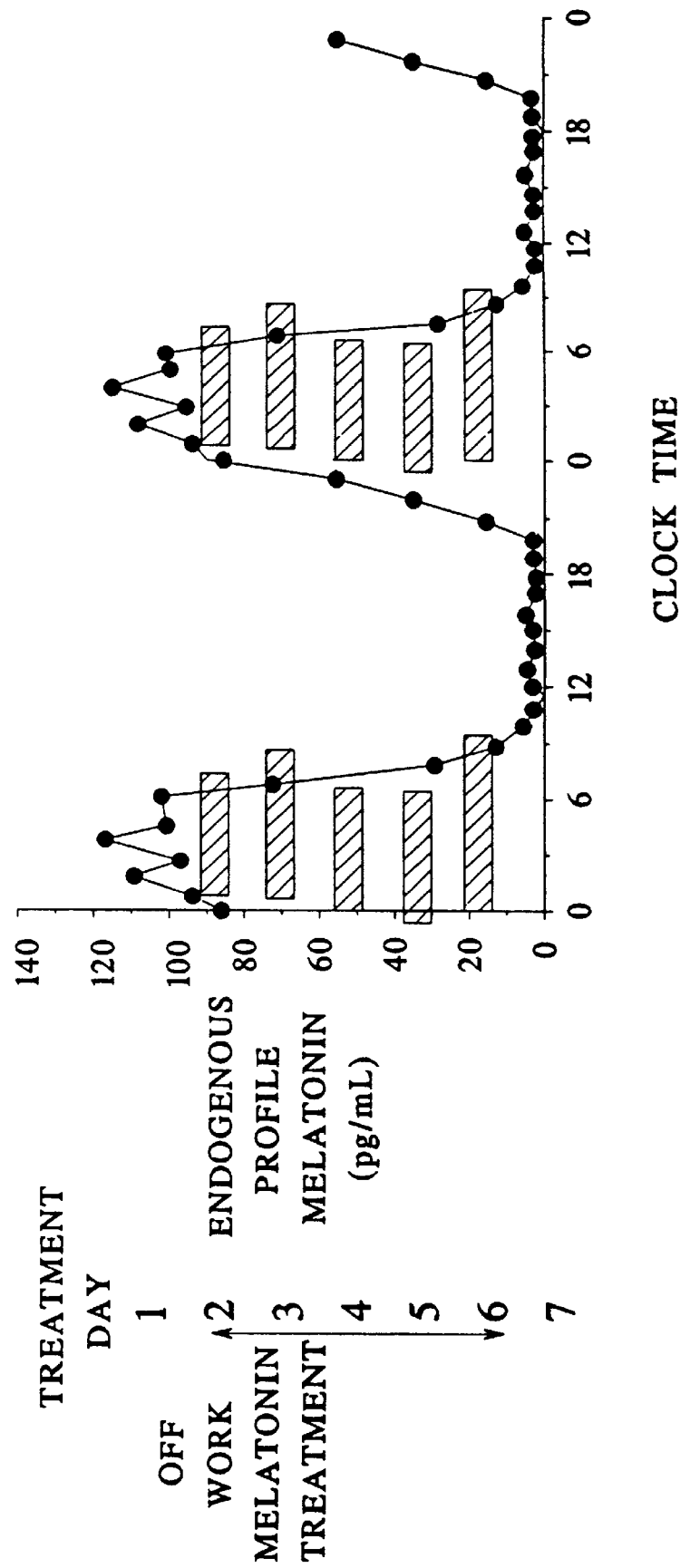
Figure 20C:
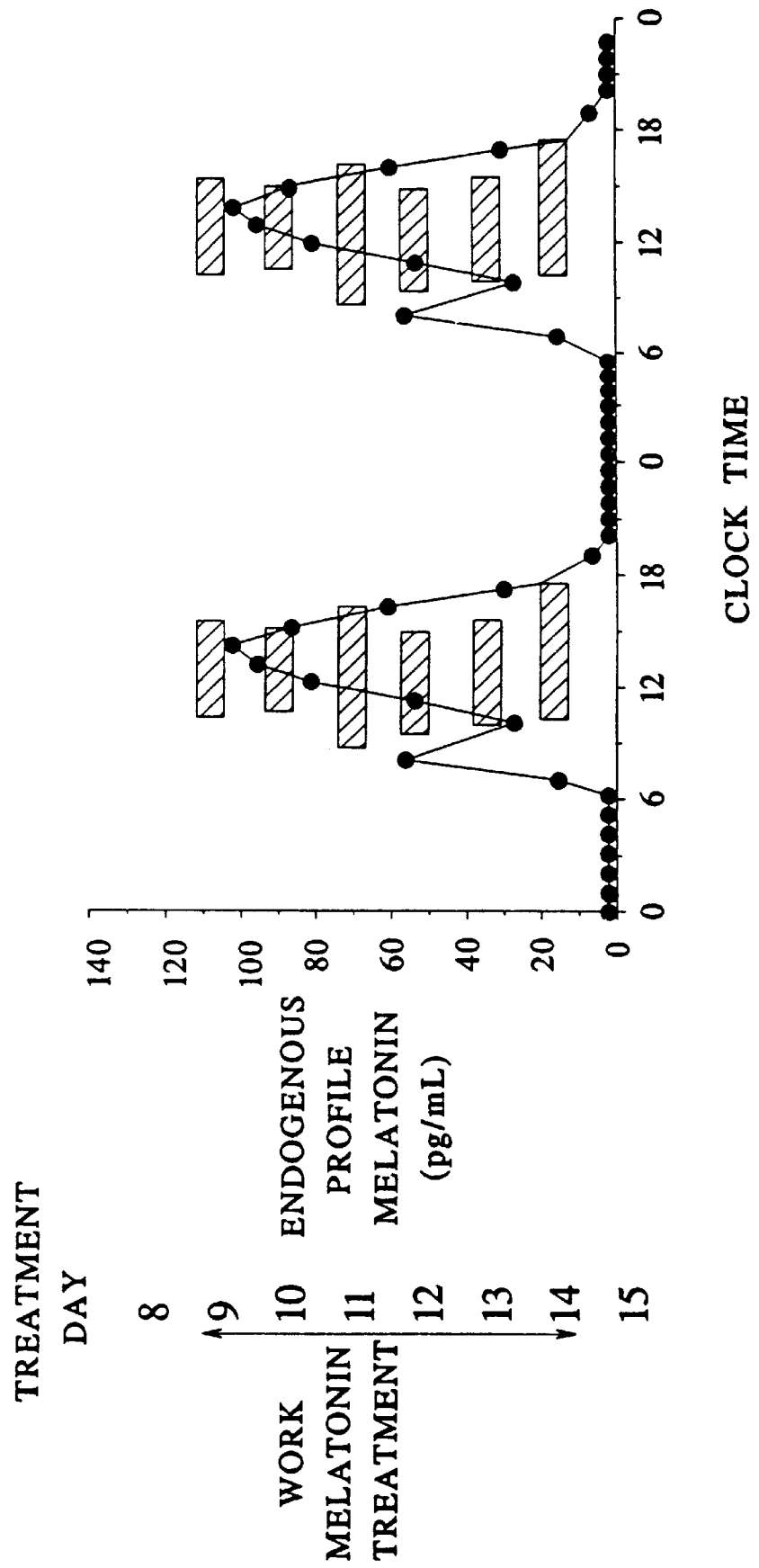
Figure 20D:
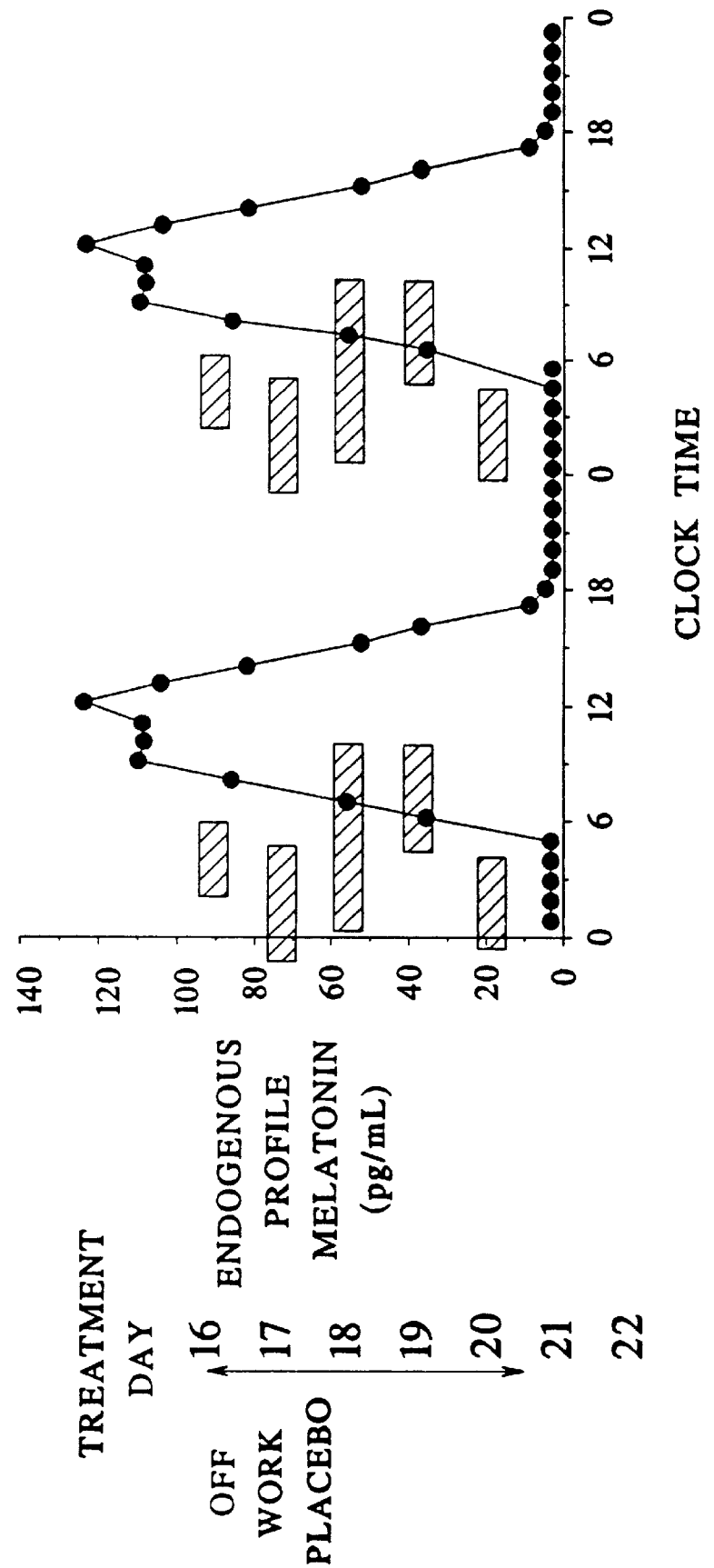
Figure 20E:
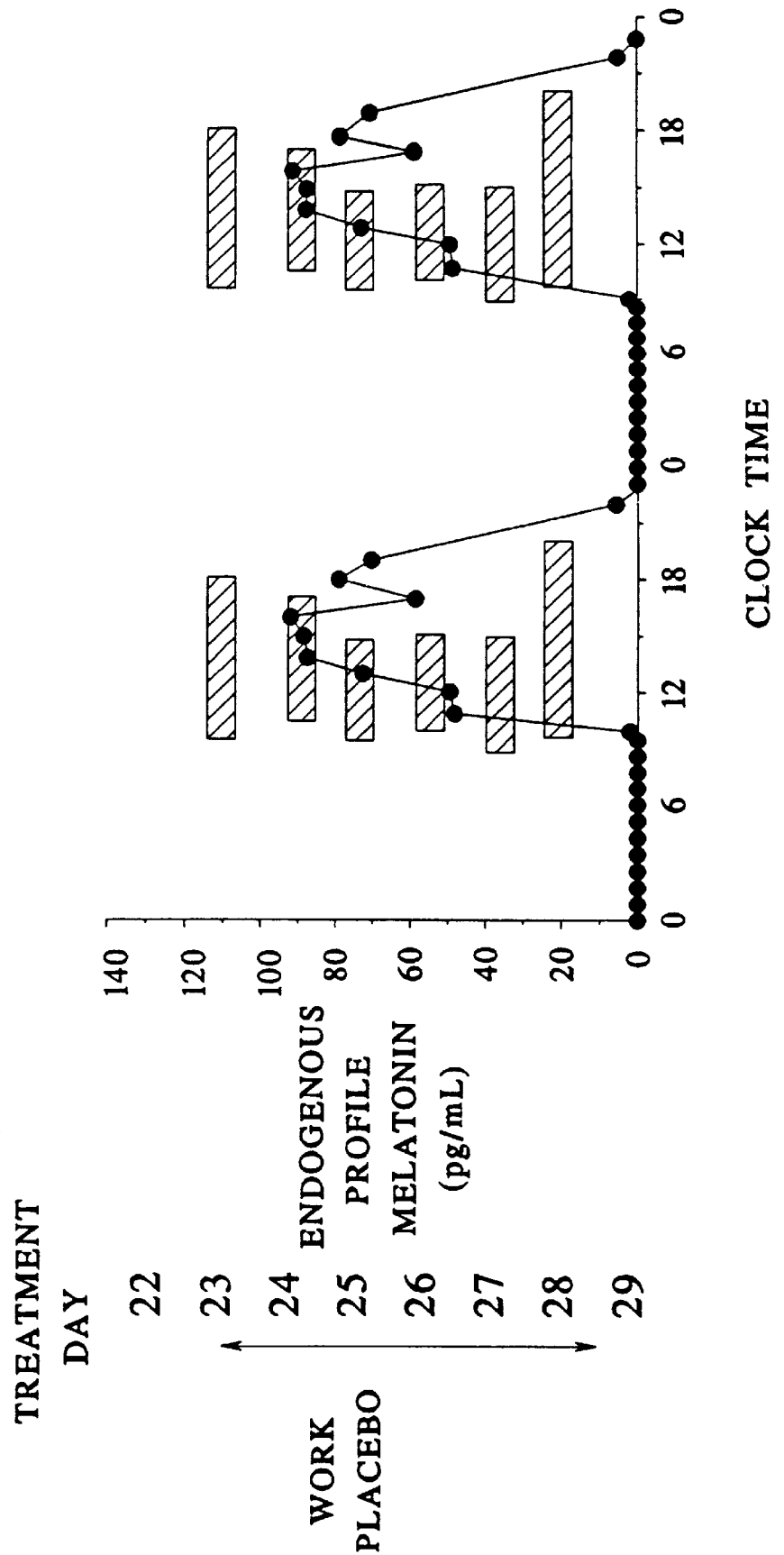

Because the results appeared to be influenced by an order effect, we also analyzed the data for phase shifts by subtracting the phase of the DLMO at the end of each week from the phase of the DLMO at the beginning of each week. In the four subjects who were treated with placebo the first two weeks, there were no baseline (pretreatment) data obtained at the beginning of the first week; for these data points, the DLMO times and melatonin PRC phase was assumed to be the same as the DLMO times and PRC phase after placebo treatment on a comparable schedule. In the two subjects who were treated with melatonin the first week, we obtained a baseline DLMO. For this analysis it was assumed that each subject delayed when adapting to a nocturnal schedule, and advanced when adapted to a diurnal schedule [although this may not have been the case in all subjects (as shown in FIG. 18)].

Subjects BD and SH each exemplify a different order of treatment. Subject BD received placebo treatments first, followed by melatonin (FIG. 19A through 19D). When first measured after a week of work taking placebo, the melatonin profile was delayed 3:54 hours compared with the subsequent off-work week but was still in a nighttime phase and out of synchrony with daytime sleep. On the second week, after seven days off work and receiving placebo, the melatonin rhythm was in normal phase (DLMO=20:07). After a two week hiatus, the subject returned to work and took melatonin. At the end of the week of treatment, the subject's DLMO time had shifted 10:22 hours and was synchronized to her daytime sleep pattern. After the fourth week, when the subject was off work and taking melatonin, the melatonin profile was back at the nighttime phase (DLMO=19:01).

Subject SH received the reverse order of treatment (FIG. 20A through 20E). A baseline profile after seven nights of work (but prior to any treatment) showed the melatonin rhythm in normal phase, indicating no adaptation to a nocturnal schedule (DLMO=21:03). Melatonin treatment given the next week (the off-work week) was administered during the dead zone of melatonin PRC and predictably caused a relatively small phase shift in the endogenous melatonin profile (DLMO=20:34). During the second week (while working at night), the subject took melatonin in the delay zone of the melatonin PRC, and the endogenous melatonin profile delayed about 10 hours (DLMO=06:34) so that it was aligned with her daytime sleep. On the next week (off-work week) she was crossed over to placebo: her melatonin profile remained relatively unchanged (DLMO= 05:13) and was significantly out of phase with her nighttime sleep. On the fourth week (placebo treatment) the subject returned to work on the night shift: the melatonin profile delayed a few hours (DLMO=10:00), remaining once again relatively in phase with daytime sleep.

Figure 21:
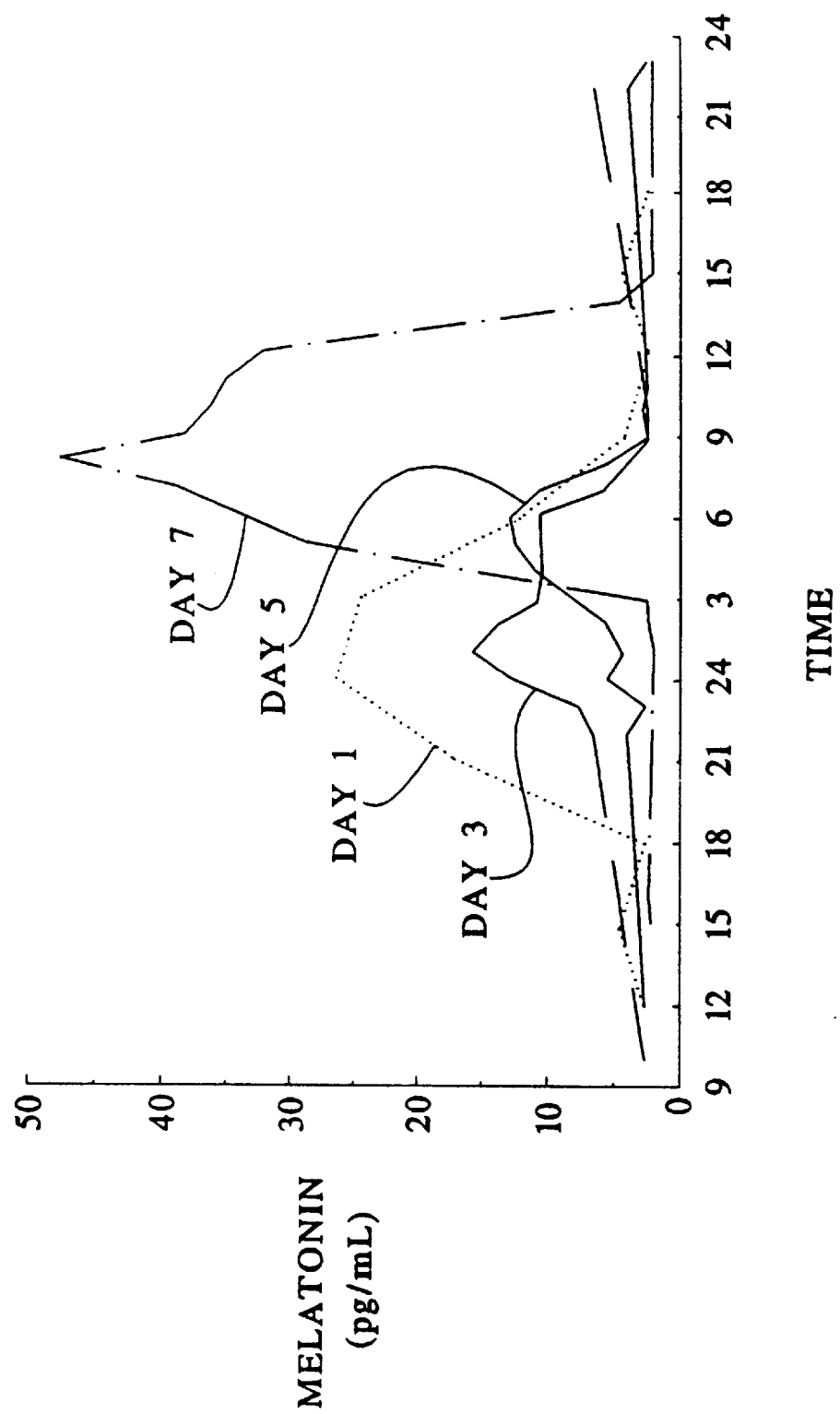
FIG. 21 shows plasma (grey curve); day 7 and salivary (black curves) days 1, 3 and 5 melatonin levels in a night-shift workers treated with 0.5 mg of melatonin taken at bedtime.
Figure 22:
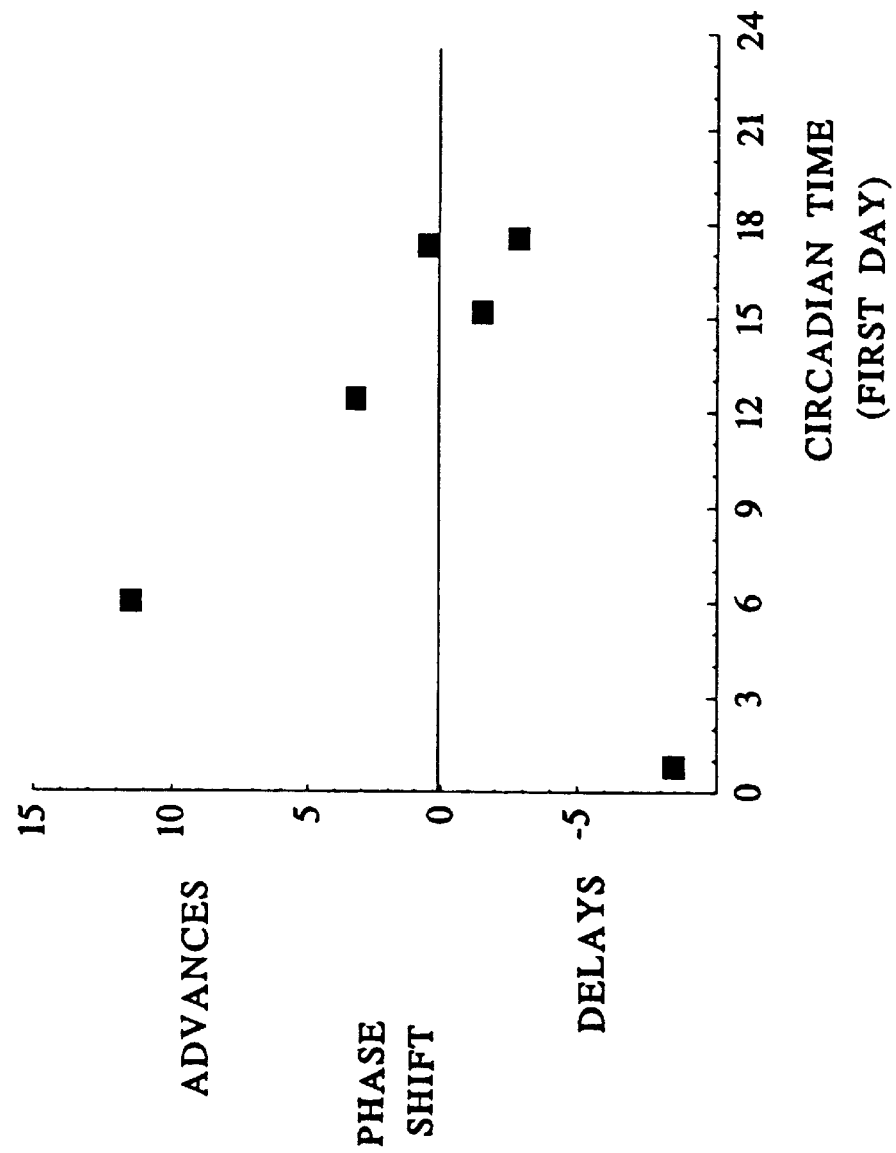
FIGS. 22–25 show the degree and direction of phase shifting achieved by treating night shift-workers using the protocol described in Example 7.
Figure 23:
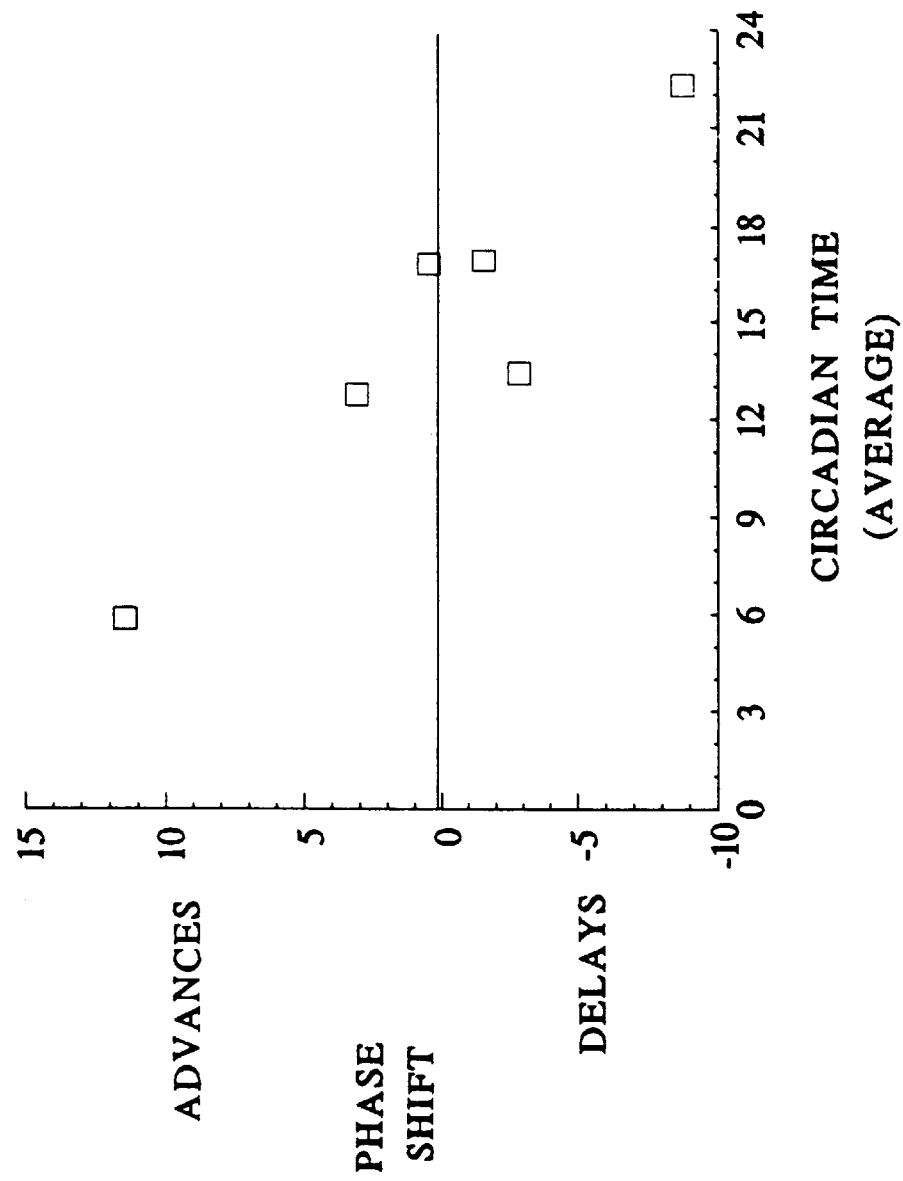
Figure 24:
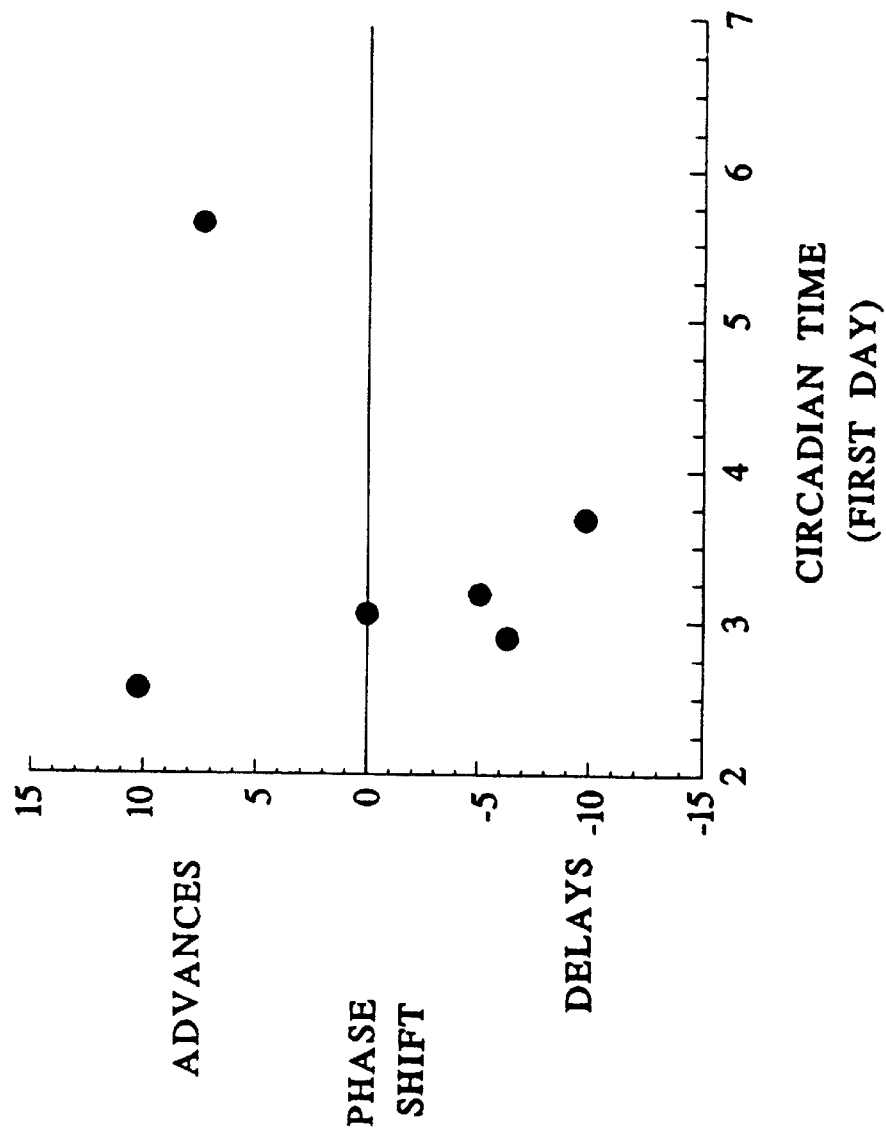
Figure 25:
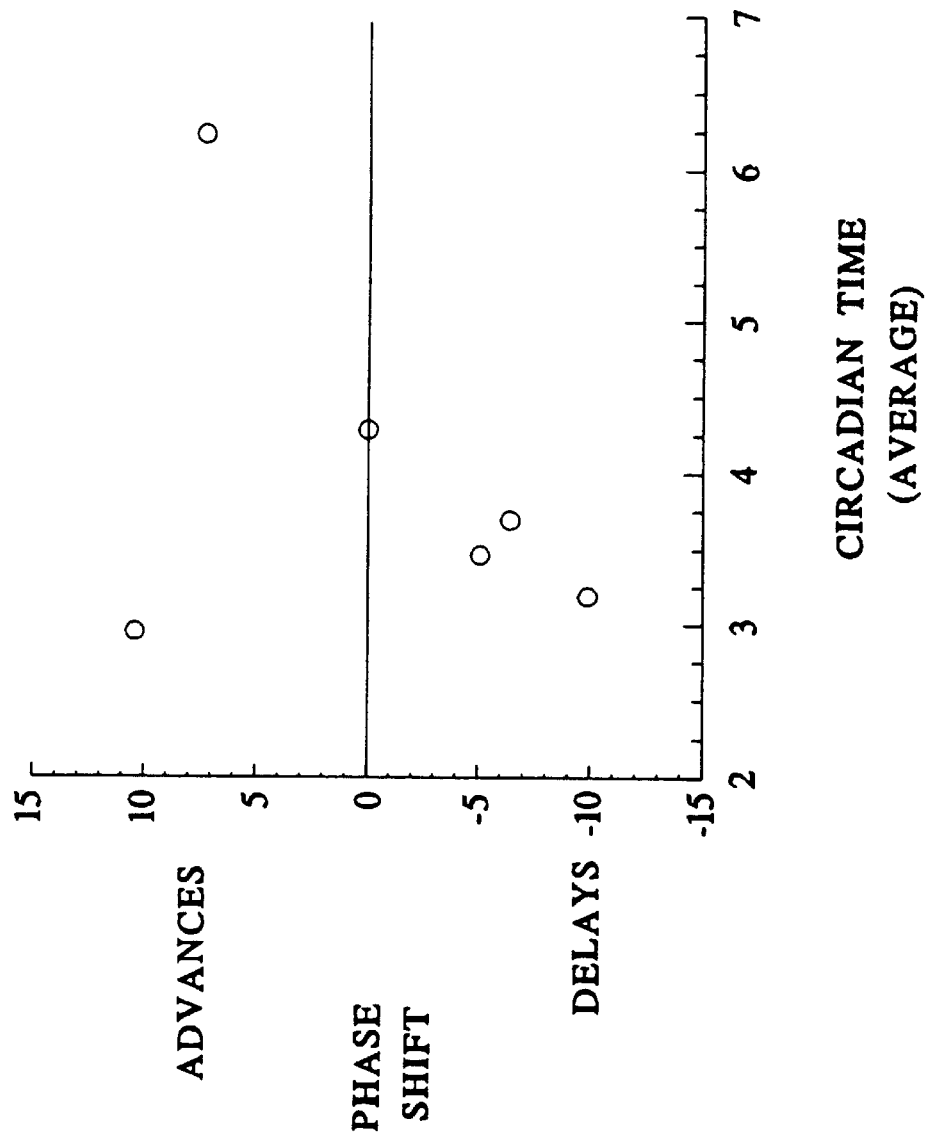

In these two subjects treated first with melatonin, the potency of the administration of melatonin is underscored by the carry-over effect observed in the subsequent placebo week. From the initial melatonin profile, it appeared that these two subjects did not shift their circadian rhythms after working at night (see FIG. 18). However, after melatonin administration, both subjects made shifts so large that they were unable to return to the baseline phase during the subsequent placebo week (FIG. 18). Salivary samples taken mid-week in one subject indicated larger phase shifts at the beginning and middle of the week than at the end of the week. As shown in FIG. 21, the amount of phase shift was greater at the beginning and middle of the week than at the end of the week. This suggests that the melatonin PRC is gradually delaying, moving the fixed administration time relatively earlier towards the zone of reduced responses.

In all subjects but one, melatonin treatment achieved significant shifts in the DLMO as predicted by the present invention. The failure of one subject to phase shift may be a function of the fact that for this person melatonin was administered during one of the cross-over points of the melatonin PRC, where reduced responses can occur. Indeed, the heterogeneous responses to melatonin in this study can be explained by each individual's circadian time of administration.

Retrospective analysis of these shift-work experiments leads to the conclusion that shiftworkers would be effectively phase-shifted by exogenous melatonin treatments conducted using a more rigorous determination of each shift-worker's DLMO time and administration times coordinated so as to keep the time of administration constant relative to the DLMO time. Phase-shifting results cast in terms of the worker's initial and average circadian time of administration (FIGS. 22–25) show that phase advances occurred at melatonin administration times corresponding to between about CT 6 and about CT 12, whereas phase delays occurred at melatonin administration times corresponding to between about CT 19 and about CT 2.

EXAMPLE 8

Utility of Dark Goggles Enhancing Circadian Phase Shifting in Humans

In order to accurately measure melatonin production, avoidance of bright light is important since melatonin production is suppressed or masked by exposure to bright light. In the past, welder's goggles or sunglasses capable of selectively filtering blue and green wavelengths of light (the segment of the spectrum most active in suppressing melatonin production) have been used (an example is Serengreti® Vermillion sunglasses). A study was performed on one subject using sunglasses to inhibit bright light suppression of melatonin production.

Serial blood samples were collected from this subject on a half-hourly schedule from 2300 hours to 0400 hours on three separate occasions. Samples were centrifuged and plasma separated and frozen immediately for analysis of melatonin content by radioimmunoassay (RIA) as described previously (Example 7). From 2300 to 0200 hours, the subject remained in dim light (less than 50 lux) or the subject was exposed to 250 lux or 2,500 lux while wearing Serengreti® sunglasses; following this, from 0200 to 0400 hours, the subject was exposed to light treatment without wearing sunglasses.

Figure 26:
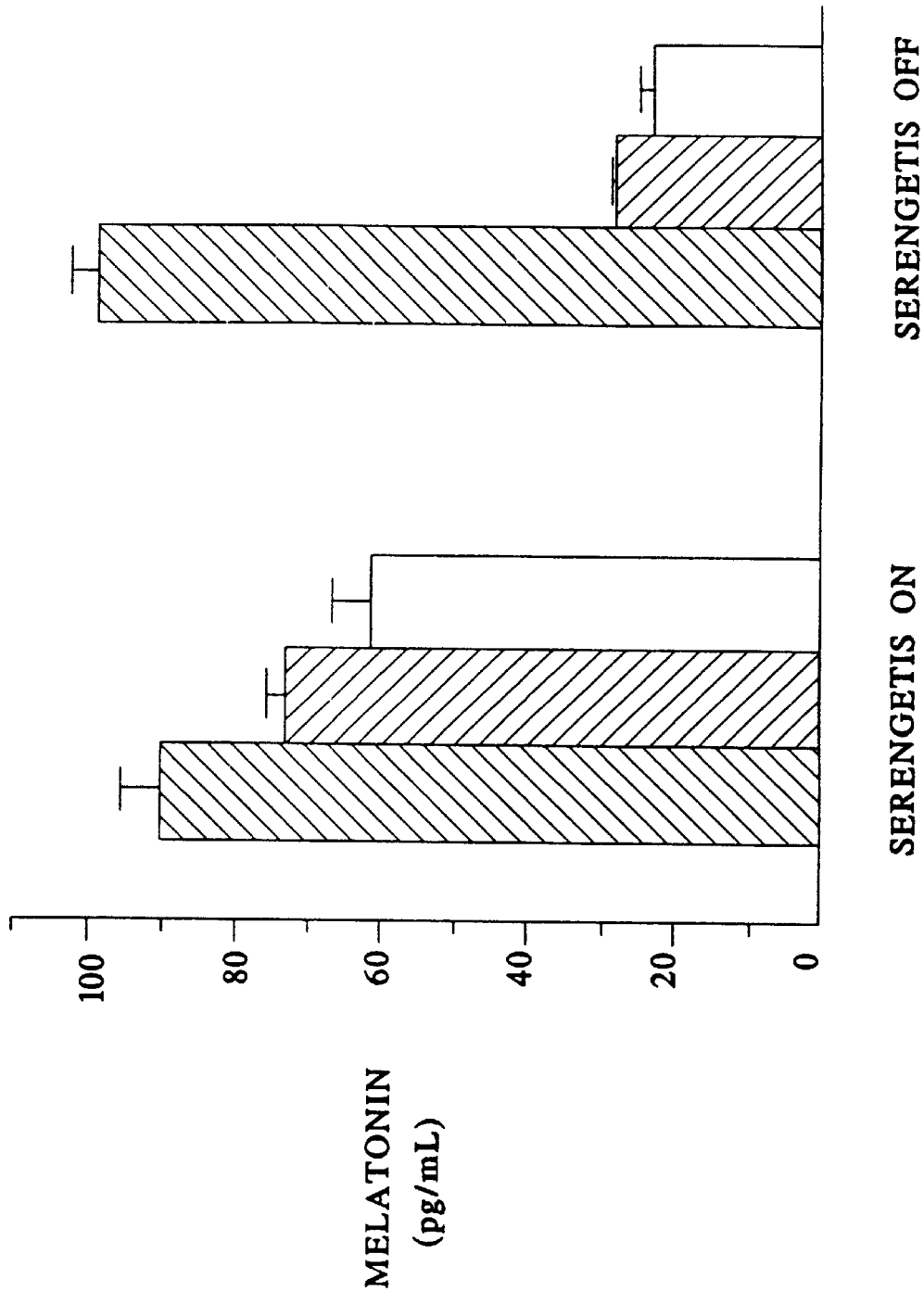
FIG. 26 illustrates the average (±standard error) amount of melatonin production (in pg) in a subject exposed to three different levels of light, with or without wearing sunglasses; (<50 lux shown by the crosshatched bars (////); 250 lux shown by the crosshatched bars (\\\\) and 2500 lux shown by the open bars and FIG. 27 shows the magnitude of phase delays (in minutes) achieved in a subject using a protocol of 0.5 mg melatonin taken for 4 days on two separate occasions, once while wearing sunglasses and once without wearing sunglasses.

The results depicted in FIG. 26 show the average (±standard error) melatonin levels found during two intervals for the three lighting conditions. During the first interval (when glasses were worn), melatonin levels were higher under dim light conditions; about 20% lower with exposure to 250 lux; and 30% lower upon exposure to 2,500 lux. When the sunglasses were removed, melatonin production fell to less than 30% of the levels measured under dim light. These results illustrate the effectiveness of eye wear that can filter out blue and green wavelengths of light for inhibiting bright lights suppression of endogenous melatonin production.

Using this information, the use of filtered eye wear (i.e., sunglasses or goggles) to enhance the treatment of individuals with melatonin was performed. A subject was monitored using serial blood assays as described above, and then treated using an exogenous melatonin administration protocol for six days. The first two capsules given to the subject were placebo capsules, and the last four contained 0.5 mg melatonin taken at 0900 hours. Analysis of the subject's DLMO at the end of this period showed that the DLMO time had been delayed by about 25 minutes compared to the reference baseline DLMO determined prior to the start of the experiment one week before.

In a second trial, the subject was given the same doses of melatonin administered at 0830 hours. During this trial, the subject was instructed to wear dark tinted (Serengreti®) goggles on days when the subject was taking melatonin. The subject wore the goggles for six hours (i.e., from the time the subject took the capsules until 1430 hours). At the end of the week, analysis of the subject's DLMO showed a phase delay of over 1 hour (abour 61 min) compared to the reference baseline DLMO one week earlier. [Note that these times of administration, i.e., 0900 or 0830 hours were nearly identical administration times for the subject relative to his circadian time (i.e., CT 1.26 versus CT 1.86, respectively).]

Figure 27:
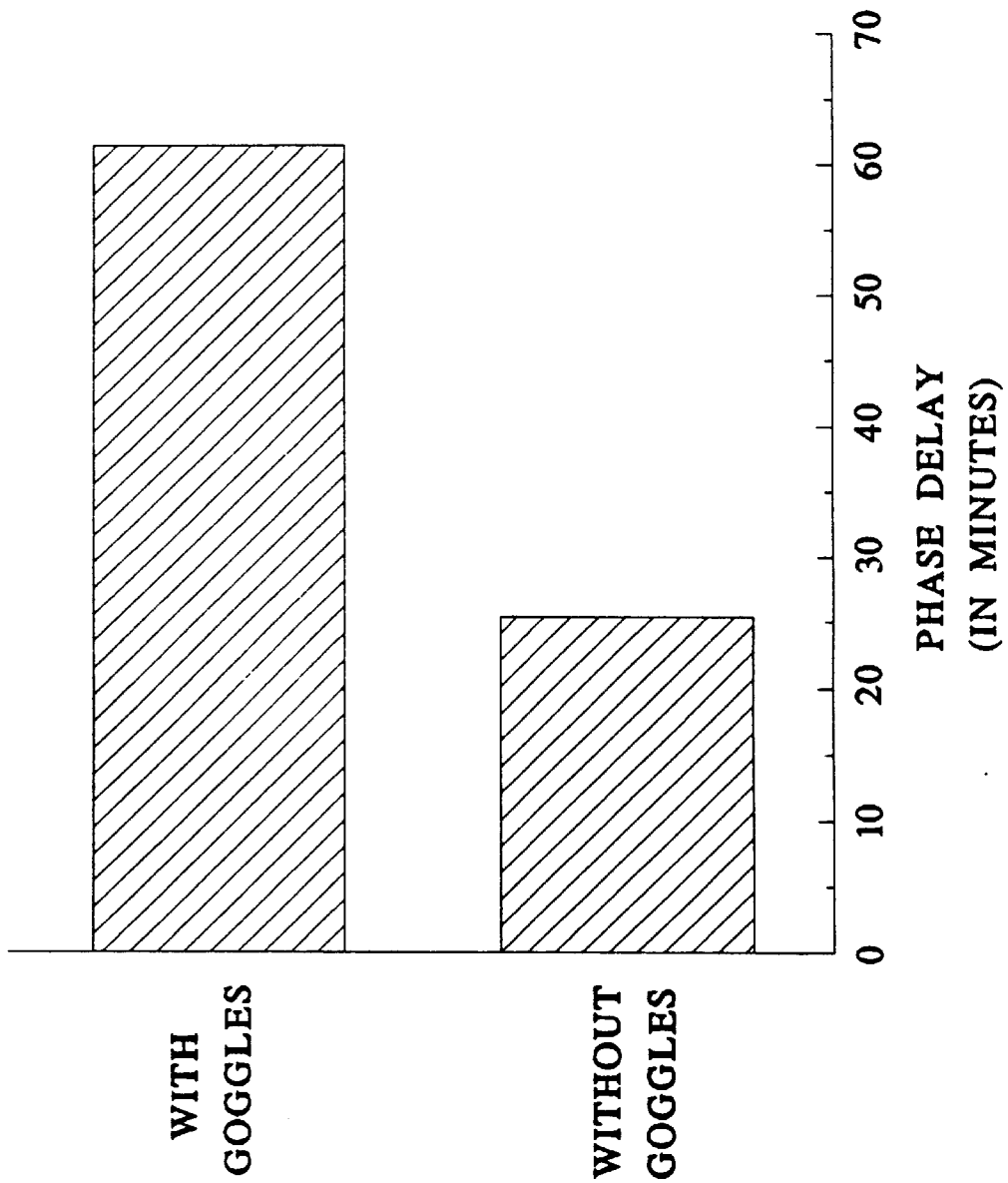

The results of these experiments are shown in FIG. 27. FIG. 27 illustrates the phase shift found in the two experiments (showing a 61.2 minute delay with goggles versus q 25.2 minute delay without goggles. From the results described above (see FIG. 26), these sunglasses had been established as being capable of avoiding bright light-induced suppression of endogenous melatonin in the subject. Taken together, these results demonstrated that the phase-shifting effect of exogenous melatonin treatment could be enhanced by the use of sunglasses, goggles or other means to create a concurrent "dark plus melatonin" signal indicating "nighttime darkness" to the subject's endogenous circadian pacemaker. This means that "darkness plus melatonin" administration during the day (even if the subject is not sleeping or avoiding morning bright light exposure) may convince the endogenous circadian pacemaker that it is, in fact, nighttime. This signal could possibly be made even more effective by suppressing endogenous melatonin production at night (either pharmacologically or with bright light exposure). Using bright light exposure and goggles to adjust the light/dark cycle could also be used in combination with the protocol for exogenous melatonin administration disclosed herein.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of administering melatonin to a human for treating insomnia, wherein melatonin is administered at a time from about CT4 to about CT6 or from about CT16 to about CT18 and wherein melatonin administration does not have a phase-shifting effect on the human.

2. A method of administering melatonin to a human for treating insomnia, wherein melatonin administration is administered at a time and for a physiological duration to produce a phase advance and a phase delay on the human's phase response curve of equal magnitudes, thereby having no phase shifting effect on the human.

3. A method according to claim 1, wherein melatonin is administered at a time from about circadian time 16 to about circadian time 18.

4. A method according to claim 1, wherein melatonin is administered at a time from about circadian time 4 to about circadian time 6.

* * * * *